US011505621B2

(12) United States Patent
Lunyak et al.

(10) Patent No.: US 11,505,621 B2
(45) Date of Patent: Nov. 22, 2022

(54) H1.0K180ME2 ANTIBODIES, METHODS OF MAKING AND USES THEREOF

(71) Applicant: Aelan Cell Technologies, Inc., San Francisco, CA (US)

(72) Inventors: Victoria V. Lunyak, San Anselmo, CA (US); James Robert Tollervey, San Rafael, CA (US)

(73) Assignee: AELAN CELL TECHNOLOGIES, INC., San Francisco, CA (US)

( * ) Notice: Subject to any disclaimer, the term of this patent is extended or adjusted under 35 U.S.C. 154(b) by 122 days.

(21) Appl. No.: 16/857,091

(22) Filed: Apr. 23, 2020

(65) Prior Publication Data

US 2020/0362056 A1    Nov. 19, 2020

Related U.S. Application Data

(63) Continuation of application No. PCT/US2018/057602, filed on Oct. 25, 2018.

(60) Provisional application No. 62/577,041, filed on Oct. 25, 2017.

(51) Int. Cl.
| | | |
|---|---|---|
| C07K 16/18 | (2006.01) | |
| C07K 16/44 | (2006.01) | |
| A61K 39/00 | (2006.01) | |

(52) U.S. Cl.
CPC ........ *C07K 16/44* (2013.01); *A61K 2039/505* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 8,981,066 B2 | 3/2015 | Lunyak | |
| 9,555,109 B2 | 1/2017 | Bogdanov et al. | |
| 2003/0092095 A1 | 5/2003 | Huang | |
| 2003/0200563 A1 | 10/2003 | Butler et al. | |
| 2007/0287166 A1 | 12/2007 | Kanai et al. | |
| 2008/0199964 A1 | 8/2008 | Shokat et al. | |
| 2009/0149343 A1 | 6/2009 | Nightingale | |
| 2010/0196941 A1 | 8/2010 | Braun et al. | |
| 2010/0305473 A1 | 12/2010 | Yuzhakov | |
| 2011/0201023 A1 | 8/2011 | Braulke et al. | |
| 2012/0121600 A1 | 5/2012 | Rau et al. | |
| 2013/0029998 A1 | 1/2013 | Mayanil et al. | |
| 2013/0065254 A1 | 3/2013 | Lunyak | |
| 2013/0230858 A1 | 9/2013 | Cantor et al. | |
| 2013/0345115 A1 | 12/2013 | An | |
| 2014/0093865 A1 | 4/2014 | Espinosa et al. | |
| 2014/0099305 A1 | 4/2014 | Epstein et al. | |
| 2014/0162904 A1 | 6/2014 | Yu | |
| 2015/0208985 A1 | 7/2015 | Huang | |
| 2015/0330996 A1 | 11/2015 | Bawden et al. | |
| 2019/0234948 A1 | 8/2019 | Lunyak et al. | |
| 2019/0322729 A1 | 10/2019 | Lunyak et al. | |
| 2021/0302429 A1* | 9/2021 | Lunyak | G01N 33/573 |

FOREIGN PATENT DOCUMENTS

| | | |
|---|---|---|
| WO | WO-2015/131836 A1 | 9/2015 |
| WO | WO-2017/049296 A1 | 3/2017 |
| WO | WO-2017/184873 A2 | 10/2017 |
| WO | WO-2017/184895 A2 | 10/2017 |
| WO | WO-2019/084332 A1 | 5/2019 |

OTHER PUBLICATIONS

Connor et al. "A simple method for improving the specificity of anti-methyl histone antibodies", Epigenetics, Jul. 1, 2010. 5:392-395.
Edwards, et al. "The remarkable flexibility of the human antibody repertoire; isolation of over one thousand different antibodies to a single protein, BLyS"; J Mol Biol.; 334(1):103-18. (Nov. 14, 2003).
Extended European Search Report dated Dec. 17, 2019 for EP Application No. 17786657.1, filed Apr. 20, 2017, 12 pages.
Fagan, T. J. "Letter: Nomogram for Bayes theorem", N. Engl. J. Med., Jul. 31, 1975. 293(5):257.
Horiuchi et al. "Assay Development for Histone Methyltransferases", Assay and drug development technologies. May 1, 2013; 11 (4):227-36.
International Search Report and Written Opinion for related International Application No. PCT/US2017/028653 dated Oct. 19, 2017, 17 pages.
International Search Report and Written Opinion for related International Application No. PCT/US2017/028686 dated Dec. 5, 2017, 26 pages.
International Search Report and Written Opinion for related International Application No. PCT/US2018/057602 filed dated Feb. 1, 2019, 18 pages.
Jenuwein, T. et al. "Translating the histone code", Science, Aug. 20, 2001. [retrieved from the internet Apr. 24, 2019], 293(5532):1074-80.
Kamakaka, R. T. et al. "Histone variants: deviants?", Genes. Dev. Feb. 2005. [retrieved from the internet Apr. 24, 2019], 1;19(3):295-310.
Kim, T. et al. "Dimethylation of H3K4 by Set1 recruits the Set3 histone deacetylase complex to 5' transcribed regions", Cell; 137(2): 259-272. (Apr. 17, 2009).
Lanning, D et al. Intestinal Microflora and Diversification of the Rabbit Antibody Repertoire. Journal of Immunology. Aug. 15, 2000, vol. 165, No. 4, pp. 2012-2019; Genbank supplement p. 1; 10 pages.
Lanning, DK et al., "Immunoglobulin heavy chain, partial [Oryctolagus cuniculus]: GenBank: AAB70644.1", National Center for Biotechnology Information. Genbank Entry. Aug. 13, 1997 [retrieved on Dec. 17, 2018], Retrieved from the internet: <URL: https://www.ncbi.nlm.nih.gov/protein/AAB70644.1?report=genbank&log$= protalign&blast_rank=1&RID= 1G1G3EYD015>; 1 page.

(Continued)

*Primary Examiner* — Daniel E Kolker
*Assistant Examiner* — Aditi Dutt
(74) *Attorney, Agent, or Firm* — Cooley LLP

(57) ABSTRACT

Provided herein are antibodies that specifically bind a protein comprising an H1.0K180me2 antigen or a peptide thereof, methods of making such antibodies, and methods of using such antibodies for therapeutics and diagnostics.

20 Claims, 30 Drawing Sheets

Specification includes a Sequence Listing.

(56) References Cited

OTHER PUBLICATIONS

Lunyak et al. "Epigenetic regulation of stem cell fate", Hum. Mol. Genet., 2008. [retrieved from the internet Apr. 24, 2019], 17(1), R28-36.

NCBI Blast, "histone H1.0 [*Homo sapiens*]: NCBI Reference Sequence: NP_005309.1 ", [database online], [retrieved on Apr. 24, 2019] Retrieved from the National Center for Biotechnology Information Search database using Internet <URL: https://www.ncbi.nlm.nih.gov/protein/NP_005309.1/>. 1 page.

Non-Final Office Action dated Feb. 18, 2020 for U.S. Appl. No. 16/164,701, filed Oct. 18, 2018, 14 pages.

Non-Final Office Action dated Jul. 9, 2020 for U.S. Appl. No. 16/164,676, filed Oct. 18, 2018, 20 pages.

Pogribny et al. "Fractionated Low-Dose Radiation Exposure Leads to Accumulation of DNA Damage and Profound Alterations in DNA and Histone Methylation in the Murine Thymus", Mol Cancer Res, Oct. 1, 2005. [retrieved from the internet Apr. 24, 2019], 3:553-61.

Prince, M. J. "Predicting the onset of Alzheimer's disease using Bayes' theorem", Am J Epidemiol. Feb. 1, 1996 [retrieved from the internet Apr. 24, 2019]; 143(3):301-8.

Sehgal, D. et al., Generation of Heterogeneous Rabbit Anti-DNP Antibodies by Gene Conversion and Hypermutation of Rearranged VL and VH Genes during Clonal Expansion of B cells in Splenic Germinal Centers. European Journal of Immunology. Dec. 2000, vol. 30, No. 12; pp. 3634-3644, 11 pages.

Tollervey, J. R. et al. "Epigenetics: judge, jury and executioner of stem cell fate", Epigenetics, Aug. 2012. 7(8):823-40.

Wan, L. B. et al. "Regulation of imprinting in clusters: noncoding RNAs versus insulators", Adv. Genet. 2008. 61:207-223.

Weiss, T. et al. "Histone H1 variant-specific lysine methylation by G9a/KMT1C and Glp1/KMT1D", Epigenetics & Chromatin, Mar. 24, 2010,3(7):1-13.

\* cited by examiner

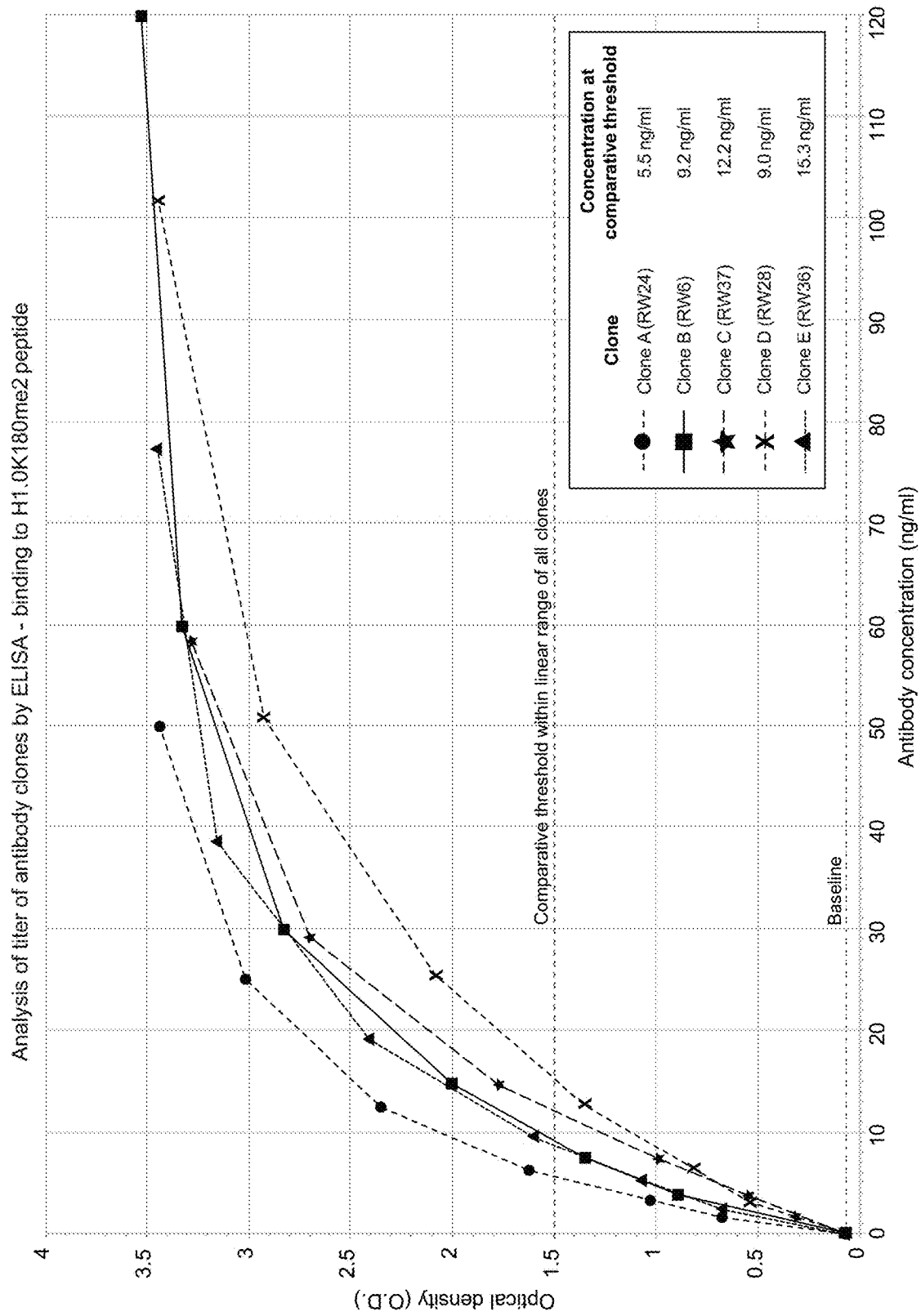

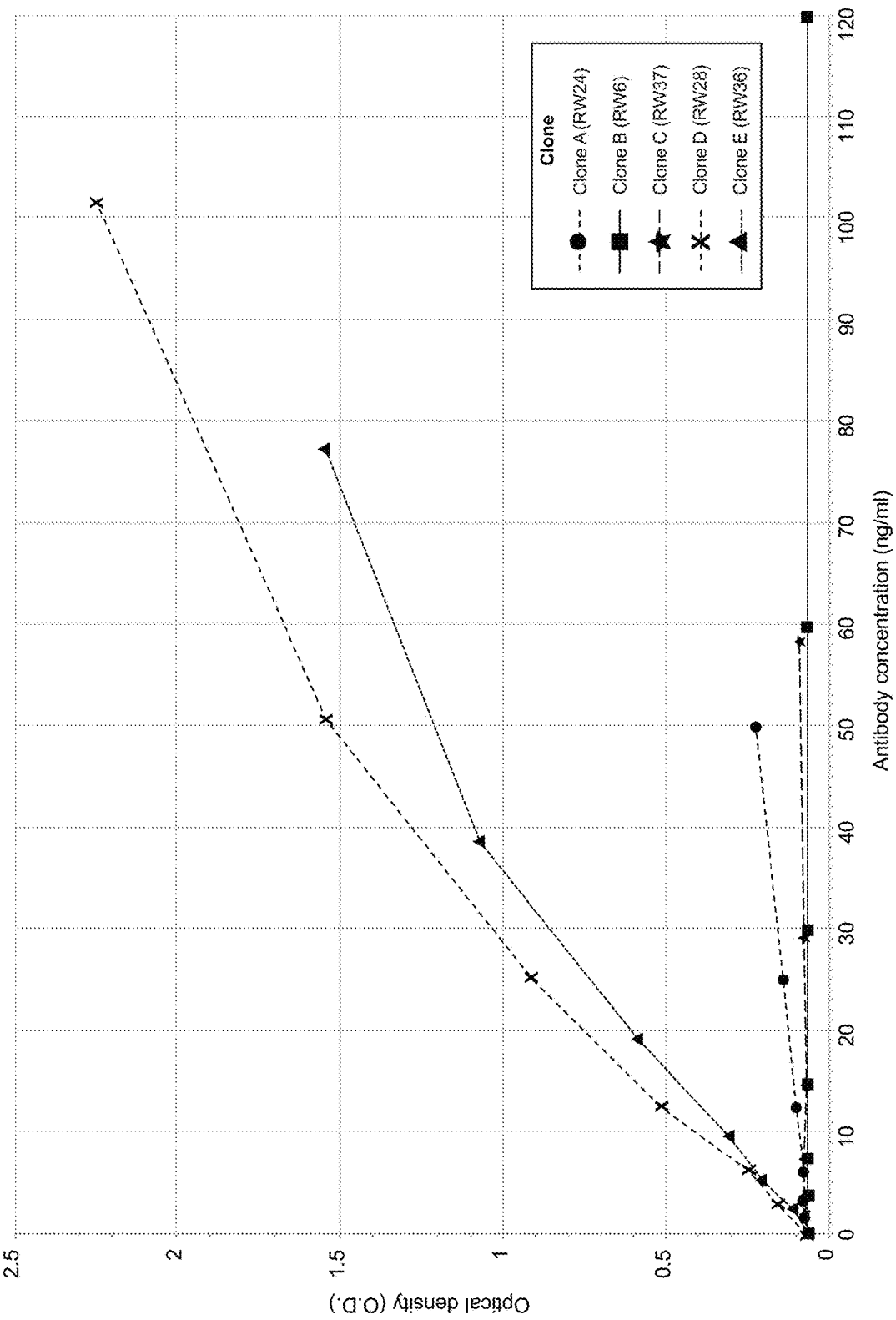

FIG. 2C

ELISA titration raw data for each clone

| Clone A (RW24) concentration (ng/ml) | 0.00 | 1.56 | 3.12 | 6.24 | 12.48 | 24.95 | 49.90 |
|---|---|---|---|---|---|---|---|
| H1.0K180me2 binding O.D. | 0.06 | 0.67 | 1.02 | 1.62 | 2.35 | 3.01 | 3.44 |
| Unmodified H1.0 binding O.D. | 0.06 | 0.07 | 0.07 | 0.08 | 0.10 | 0.14 | 0.23 |

| Clone B (RW6) concentration (ng/ml) | 0.00 | 3.74 | 7.49 | 14.98 | 29.95 | 59.90 | 119.80 |
|---|---|---|---|---|---|---|---|
| H1.0K180me2 binding O.D. | 0.06 | 0.90 | 1.34 | 2.01 | 2.83 | 3.33 | 3.53 |
| Unmodified H1.0 binding O.D. | 0.06 | 0.06 | 0.06 | 0.06 | 0.07 | 0.06 | 0.07 |

| Clone C (RW37) concentration (ng/ml) | 0.00 | 1.82 | 3.64 | 7.29 | 14.58 | 29.15 | 58.30 |
|---|---|---|---|---|---|---|---|
| H1.0K180me2 binding O.D. | 0.06 | 0.32 | 0.53 | 0.98 | 1.77 | 2.70 | 3.27 |
| Unmodified H1.0 binding O.D. | 0.06 | 0.07 | 0.07 | 0.07 | 0.07 | 0.08 | 0.09 |

| Clone D (RW28) concentration (ng/ml) | 0.00 | 3.18 | 6.36 | 12.73 | 25.45 | 50.90 | 101.80 |
|---|---|---|---|---|---|---|---|
| H1.0K180me2 binding O.D. | 0.06 | 0.54 | 0.82 | 1.35 | 2.08 | 2.92 | 3.45 |
| Unmodified H1.0 binding O.D. | 0.06 | 0.16 | 0.25 | 0.52 | 0.91 | 1.55 | 2.23 |

| Clone E (RW36) concentration (ng/ml) | 0.00 | 2.41 | 4.82 | 9.64 | 19.28 | 38.55 | 77.10 |
|---|---|---|---|---|---|---|---|
| H1.0K180me2 binding O.D. | 0.06 | 0.67 | 1.01 | 1.60 | 2.41 | 3.15 | 3.44 |
| Unmodified H1.0 binding O.D. | 0.06 | 0.11 | 0.20 | 0.31 | 0.59 | 1.07 | 1.54 |

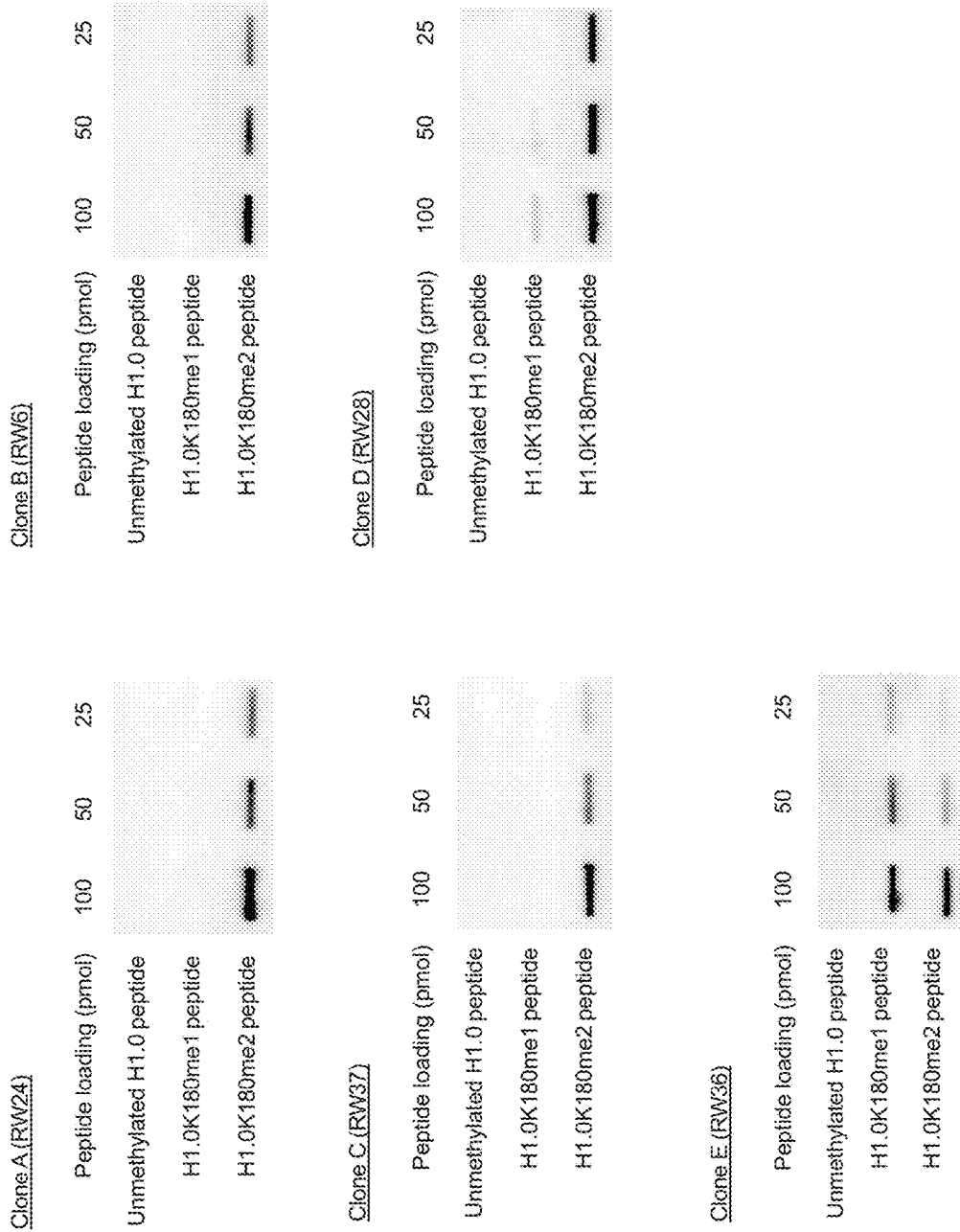

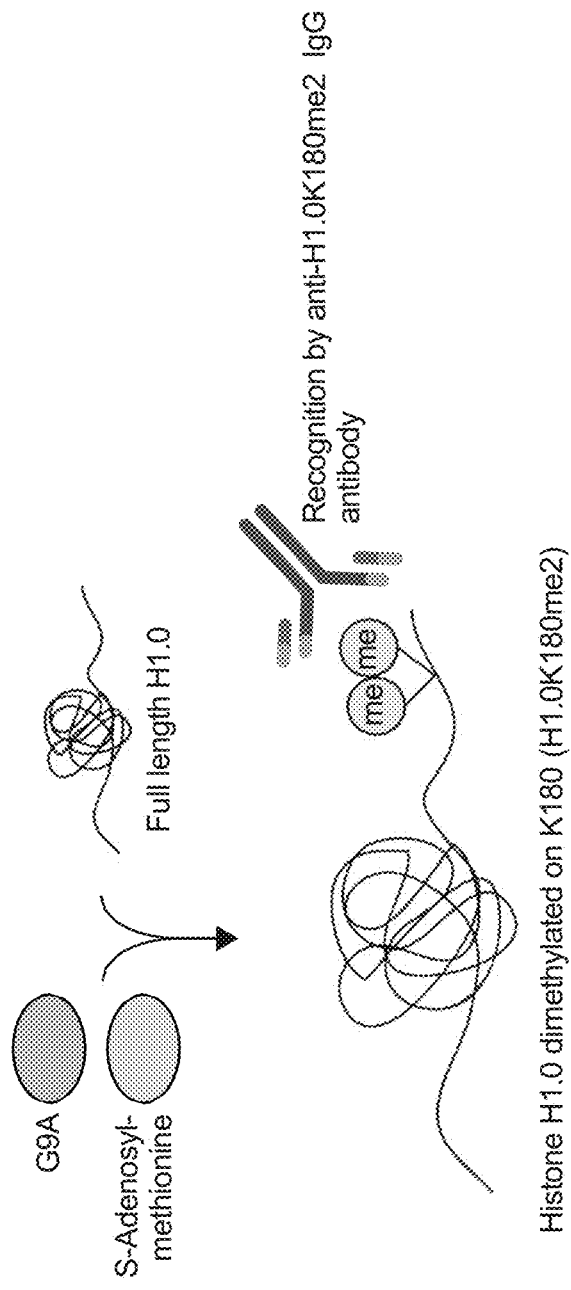

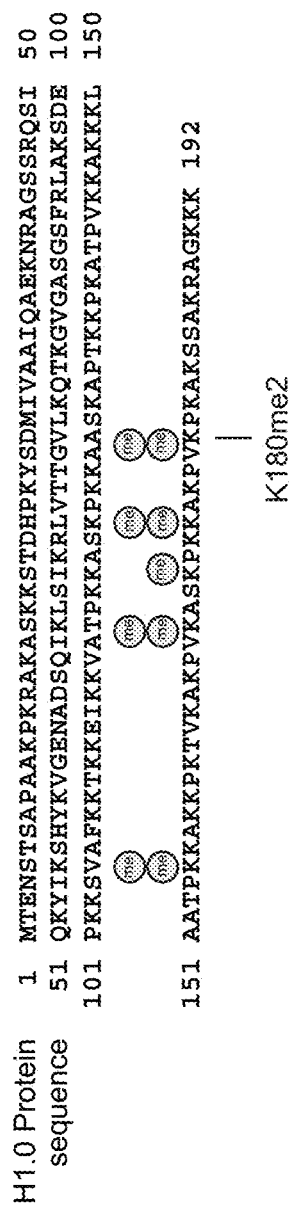
FIG. 4B Locations of G9A methylation along full-length H1.0 protein as determined by LC/MS

FIG. 5A

Heavy Chain (Isoform Gamma) Variable Domain Sequence Alignment

EMBOSS NEEDLE Pairwise Sequence Alignment
Matrix: EBLOSUM62
Gap_penalty: 10.0
Extend_penalty: 0.5

Length: 121
Identity:    74/121 (61.2%)
Similarity:  85/121 (70.2%)
Gaps:        18/121 (14.9%)
Score: 384.0

```
Clone A (RW24)    1 QSVEESGGRLVTPGTPLTLTCTVSGFSLNNYVMMWVRQAPGEGLEWIAAI    50
                    ||:::|||||||||||||||||||:||.|||::...:||||||:|||:..|
Clone B (RW6)     1 QSLEESGGRLVTPGTPLTLTCTASGFSLSDYYTTWVRQAPGQGLEYIGYI    50

Clone A (RW24)   51 TTGGTTYYANWAKGRFTISKTSTTVDLKIISPTTEDTATYFCARDLYGDT   100
                    :..|||:|||.:|||||||:|:|||:||||.|:..:|||||||||||:..
Clone B (RW6)    51 SGTGTPYYATWAKGRFTISRTSTTVGLKMTSLTTEDTATYFCARSYPGID   100

Clone A (RW24)  101 SDDIWDAFDPWGPGTLVTVSS   121
                    :::
Clone B (RW6)   101 ANN------------------   103
```

|   | Identical amino acids |
|:-:|---|
| : | Similar amino acids |
| . | Non-similar amino acids |

FIG. 5B

Light Chain (Isoform Kappa) Variable Domain Sequence Alignment

```
EMBOSS NEEDLE Pairwise Sequence Alignment
Matrix: EBLOSUM62
Gap_penalty: 10.0
Extend_penalty: 0.5

Length: 102
Identity:      85/102 (83.3%)
Similarity:    90/102 (88.2%)           |  : Identical amino acids
Gaps:           3/102 ( 2.9%)           :  : Similar amino acids
Score: 421.5                            .  : Non-similar amino acids Clone A (RW24)    1 DPVLTQTPSSVSAAVGGTVTISCQSSESVYKNNNLAWYQQKPGQPPKLLI     50
                     .||:|||||||||||||||||||:|||.|:|||.|.|:|||||||||||
Clone B (RW6)     1 AQVLTQTPSSVSAAVGGTVTISCQSSQSVYNNNYLGWYQQKPGQPPKLLI     50

Clone A (RW24)   51 YSASTLASGVPSRFKGSGSGTQFTLTISGVQCDDAATYYCLGVYSDIF--     98
                     |:||||||||||||||||||||||||||:.:||||||||:.:.:|::
Clone B (RW6)    51 YLASTLASGVPSRFKGSGSGTQFTLTISDLECDDAATYYCGGDY-DVYIA     99

Clone A (RW24)   99 AF 100
                    ||
Clone B (RW6)   100 AF 101
```

FIG. 5C

Clone A (RW24) Variable Domain DNA and Protein Sequences

Heavy chain – Isotype gamma (γ)

DNA sequence:
cagtcggtggaggagtccggggggtccgcctgtcacgcctgggacaccctgacactcacct-
gcacggtctctggattctccctcaataactatgtgatgatgtgggtccgccaggctccaggggaggggctggaatgg
atcgctgccattactactgcggtaccacatacagtccgacaaccgggctgaaaggccgattcaccatctccaaaacctc
gaccacggtggatctgaaaatcatcagtccgacaaccgaggacacggccacctattctgcgccagagatctttatg
gtgatactagtgatgatatttggatgcttttgatccctggggcccaggcaccctggtcaccgtctcctcag Protein sequence:
QSVEESGGRLVTPGTPLTLTCTVSGFSLNNYVMMWVRQAPGEGLEWIAAITTGGTTYYAN-
WAKGRFTISKTSTTVDLKIISPTTEDTATYFCARDLYGDTSDDIWDAFDPWGPGTLVTVSS Light chain – Isotype kappa (κ)

DNA sequence:
gaccctgtgctgaccagactccagtccgtcctgtctgcagctgtgggaggcacagtcac-
catcagttgccagtccagtgagagtgtttataagaataacaacttagcctgtatcagcagaaaccaggcagcctc
ccaagctcctgatctattctgcatcaactctggggtccccatcgcggttcaaaggcagtggatctgggaca
cagtcactctcaccatcagtggcgtgcagtgtgacgatgtgccacttactgtccttaggagtatatagtgatatt
tttgctttc Protein sequence:
DPVLTQTPSSVSAAVGGTVTISCQSSESVYKNNNLAWYQQKPGQPPKLLIYSAST-
LASGVPSRFKGSGSGTQFTLTISGVQCDDAATYYCLGVYSDIFAF

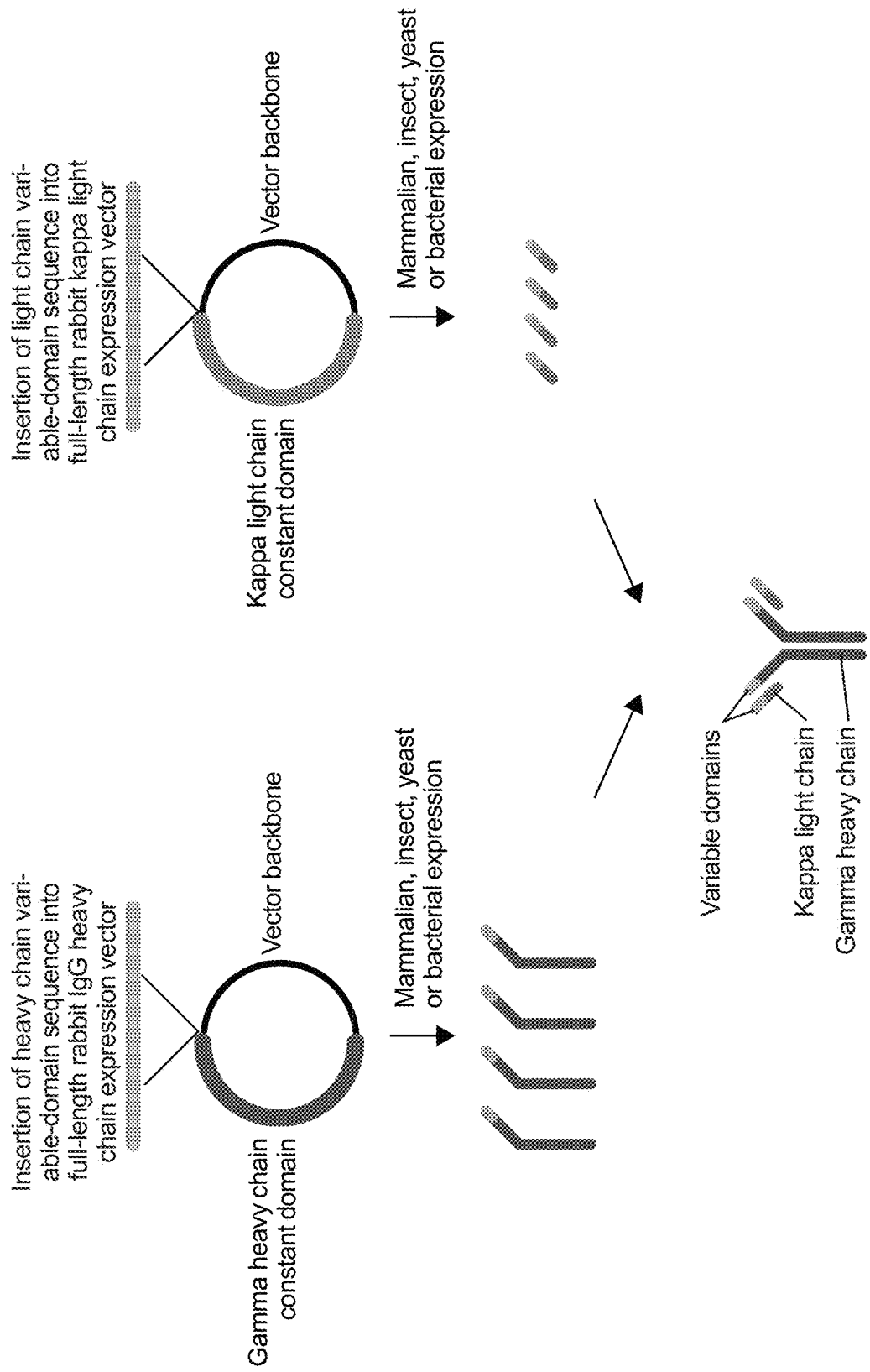

FIG. 7B

| Region | Definition | Sequence Fragment | Residues | Length |
|---|---|---|---|---|
| LFR1 | Chothia | DPVLTQTPSSVSAAVGGTVTISC------ | 1 - 23 | 23 |
| | AbM | DPVLTQTPSSVSAAVGGTVTISC------ | 1 - 23 | 23 |
| | Kabat | DPVLTQTPSSVSAAVGGTVTISC------ | 1 - 23 | 23 |
| | Contact | DPVLTQTPSSVSAAVGGTVTISCQSSESV | 1 - 29 | 29 |
| CDR-L1 | Chothia | QSSESVYKNNLA-- | 24 - 36 | 13 |
| | AbM | QSSESVYKNNLA-- | 24 - 36 | 13 |
| | Kabat | QSSESVYKNNLA-- | 24 - 36 | 13 |
| | Contact | ------YKNNLAWY | 30 - 38 | 9 |
| LFR2 | Chothia | WYQQKPGQPPKLLIY | 37 - 51 | 15 |
| | AbM | WYQQKPGQPPKLLIY | 37 - 51 | 15 |
| | Kabat | WYQQKPGQPPKLLIY | 37 - 51 | 15 |
| | Contact | ---QKPGQPPK---- | 39 - 47 | 9 |
| CDR-L2 | Chothia | -----SASTLAS | 52 - 58 | 7 |
| | AbM | -----SASTLAS | 52 - 58 | 7 |
| | Kabat | -----SASTLAS | 52 - 58 | 7 |
| | Contact | LLIYSASTLA- | 48 - 57 | 10 |
| LFR3 | Chothia | -GVPSRFKGSGSGTQFTLTISGVQCDDAATYYC | 59 - 90 | 32 |
| | AbM | -GVPSRFKGSGSGTQFTLTISGVQCDDAATYYC | 59 - 90 | 32 |
| | Kabat | -GVPSRFKGSGSGTQFTLTISGVQCDDAATYYC | 59 - 90 | 32 |
| | Contact | SGVPSRFKGSGSGTQFTLTISGVQCDDAATYYC | 58 - 90 | 33 |
| CDR-L3 | Chothia | LGVYSDIFAP | 91 - 100 | 10 |
| | AbM | LGVYSDIFAP | 91 - 100 | 10 |
| | Kabat | LGVYSDIFAP | 91 - 100 | 10 |
| | Contact | LGVYSDIFAP | 91 - 100 | 10 |
| LFR4 | Chothia | | - | - |
| | AbM | | - | - |
| | Kabat | | - | - |
| | Contact | | - | - |

FIG. 7C

| Region | Definition | Sequence Fragment | Residues | Length |
|---|---|---|---|---|
| HFR1 | Chothia | QSVEESGGRLVTPGTPLTLTCTVS------ | 1 - 24 | 24 |
|  | AbM | QSVEESGGRLVTPGTPLTLTCTVS------ | 1 - 24 | 24 |
|  | Kabat | QSVEESGGRLVTPGTPLTLTCTVSGFSLN | 1 - 29 | 29 |
|  | Contact | QSVEESGGRLVTPGTPLTLTCTVSGFSL- | 1 - 28 | 28 |
| CDR-H1 | Chothia | GFSLNNY--- | 25 - 31 | 7 |
|  | AbM | GFSLNNYVNN | 25 - 34 | 10 |
|  | Kabat | -----NYVNN | 30 - 34 | 5 |
|  | Contact | ----NNYVNN | 29 - 34 | 6 |
| HFR2 | Chothia | VNWVRQAPGSGLEWIAAI | 32 - 50 | 19 |
|  | AbM | ---WVRQAPGSGLEWIA-- | 35 - 48 | 14 |
|  | Kabat | ---WVRQAPGSGLEWIA-- | 35 - 48 | 14 |
|  | Contact | ---WVRQAPGSGLE----- | 35 - 45 | 11 |
| CDR-H2 | Chothia | -----TTGGT------ | 51 - 55 | 5 |
|  | AbM | -----AITGGTTY---- | 49 - 57 | 9 |
|  | Kabat | ---AITGGTTYANWAKG | 49 - 64 | 16 |
|  | Contact | NIAAITGGTTY------ | 46 - 57 | 12 |
| HFR3 | Chothia | TYYANWAKGRFTISRTSTTVDLKIISPTTEDTATYFCAR | 56 - 94 | 39 |
|  | AbM | --YANWAKGRFTISRTSTTVDLKIISPTTEDTATYFCAR | 58 - 94 | 37 |
|  | Kabat | -----------RFTISRTSTTVDLKIISPTTEDTATYFCAR | 65 - 94 | 30 |
|  | Contact | --YANWAKGRFTISRTSTTVDLKIISPTTEDTATYFC-- | 58 - 92 | 35 |
| CDR-H3 | Chothia | ---DLYGDTSDSINDAFDP | 95 - 110 | 16 |
|  | AbM | ---DLYGDTSDSINDAFDP | 95 - 110 | 16 |
|  | Kabat | ---DLYGDTSDSINDAFDP | 95 - 110 | 16 |
|  | Contact | ARDLYGDTSDSINDAFD-- | 93 - 109 | 17 |
| HFR4 | Chothia | -WGPGTLVTVSS | 111 - 121 | 11 |
|  | AbM | -WGPGTLVTVSS | 111 - 121 | 11 |
|  | Kabat | -WGPGTLVTVSS | 111 - 121 | 11 |
|  | Contact | PWGPGTLVTVSS | 110 - 121 | 12 |

FIG. 7D

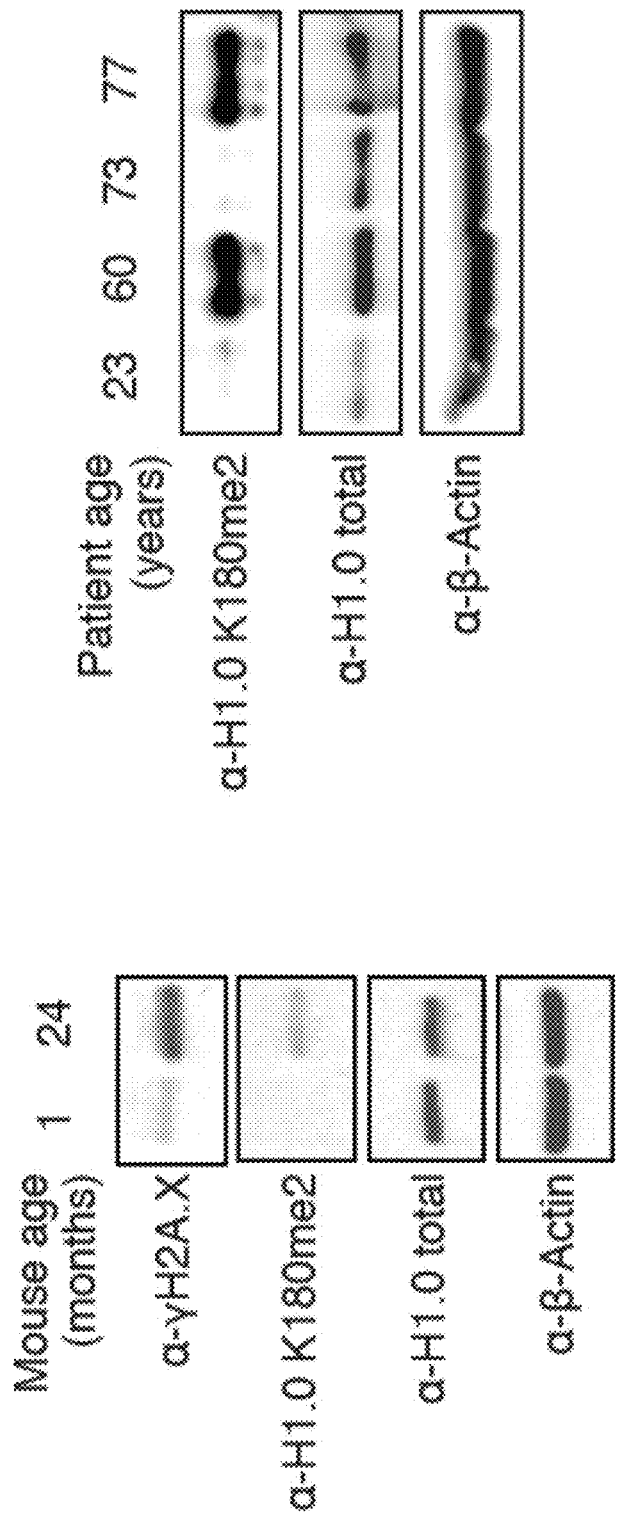
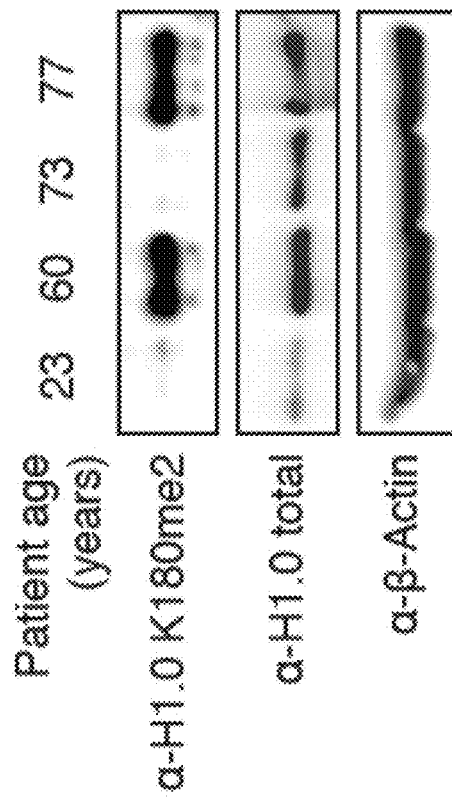
FIG. 9B
FIG. 9A

SEQUENCE LISTING

```
<160> NUMBER OF SEQ ID NOS: 74

<210> SEQ ID NO 1
<211> LENGTH: 192
<212> TYPE: PRT
<213> ORGANISM: Unknown
<220> FEATURE:
<223> OTHER INFORMATION: Histone H1.0 Protein

<400> SEQUENCE: 1

Met Thr Glu Asn Ser Thr Ser Ala Pro Ala Ala Lys Pro Lys Arg Ala
1               5                   10                  15

Lys Ala Ser Lys Lys Ser Thr Asp His Pro Lys Tyr Ser Asp Met Ile
            20                  25                  30

Val Ala Ala Ile Gln Ala Glu Lys Asn Arg Ala Gly Ser Ser Arg Gln
        35                  40                  45

Ser Ile Gln Lys Tyr Ile Lys Ser His Tyr Lys Val Gly Glu Asn Ala
    50                  55                  60

Asp Ser Gln Ile Lys Leu Ser Ile Lys Arg Leu Val Thr Thr Gly Val
65                  70                  75                  80

Leu Lys Gln Thr Lys Gly Val Gly Ala Ser Gly Ser Phe Arg Leu Ala
                85                  90                  95
```

```
Lys Ser Asp Glu Pro Lys Lys Ser Val Ala Phe Lys Lys Thr Lys Lys
                100                 105                 110

Glu Ile Lys Lys Val Ala Thr Pro Lys Lys Ala Ser Lys Pro Lys Lys
            115                 120                 125

Ala Ala Ser Lys Ala Pro Thr Lys Lys Pro Lys Ala Thr Pro Val Lys
        130                 135                 140

Lys Ala Lys Lys Leu Ala Ala Thr Pro Lys Lys Ala Lys Lys Pro
145                 150                 155                 160

Lys Thr Val Lys Pro Val Lys Ala Ser Lys Pro Lys Lys Ala Lys Pro
                165                 170                 175

Val Lys Pro Lys Ala Lys Ser Ser Ala Lys Arg Ala Gly Lys Lys Lys
            180                 185                 190

<210> SEQ ID NO 2
<211> LENGTH: 192
<212> TYPE: PRT
<213> ORGANISM: Unknown
<220> FEATURE:
<223> OTHER INFORMATION: Histone H1.0 Protein
<220> FEATURE:
<221> NAME/KEY: MISC_FEATURE
<222> LOCATION: (157)..(157)
<223> OTHER INFORMATION: Lys is dimethylated
<220> FEATURE:
<221> NAME/KEY: MISC_FEATURE
<222> LOCATION: (169)..(169)
<223> OTHER INFORMATION: Lys is dimethylated
<220> FEATURE:
<221> NAME/KEY: MISC_FEATURE
<222> LOCATION: (172)..(172)
<223> OTHER INFORMATION: Lys is methylated
<220> FEATURE:
<221> NAME/KEY: MISC_FEATURE
<222> LOCATION: (175)..(175)
<223> OTHER INFORMATION: Lys is dimethylated
<220> FEATURE:
<221> NAME/KEY: MISC_FEATURE
<222> LOCATION: (180)..(180)
<223> OTHER INFORMATION: Lys is dimethylated

<400> SEQUENCE: 2

Met Thr Glu Asn Ser Thr Ser Ala Pro Ala Ala Lys Pro Lys Arg Ala
1               5                   10                  15

Lys Ala Ser Lys Lys Ser Thr Asp His Pro Lys Tyr Ser Asp Met Ile
            20                  25                  30

Val Ala Ala Ile Gln Ala Glu Lys Asn Arg Ala Gly Ser Ser Arg Gln
        35                  40                  45

Ser Ile Gln Lys Tyr Ile Lys Ser His Tyr Lys Val Gly Glu Asn Ala
50                  55                  60

Asp Ser Gln Ile Lys Leu Ser Ile Lys Arg Leu Val Thr Thr Gly Val
65                  70                  75                  80

Leu Lys Gln Thr Lys Gly Val Gly Ala Ser Gly Ser Phe Arg Leu Ala
                85                  90                  95

Lys Ser Asp Glu Pro Lys Lys Ser Val Ala Phe Lys Lys Thr Lys Lys
                100                 105                 110

Glu Ile Lys Lys Val Ala Thr Pro Lys Lys Ala Ser Lys Pro Lys Lys
            115                 120                 125

Ala Ala Ser Lys Ala Pro Thr Lys Lys Pro Lys Ala Thr Pro Val Lys
        130                 135                 140

Lys Ala Lys Lys Leu Ala Ala Thr Pro Lys Lys Ala Lys Lys Pro
145                 150                 155                 160
```

Lys Thr Val Lys Pro Val Lys Ala Ser Lys Pro Lys Lys Ala Lys Pro
            165                 170                 175

Val Lys Pro Lys Ala Lys Ser Ser Ala Lys Arg Ala Gly Lys Lys Lys
        180                 185                 190

<210> SEQ ID NO 3
<211> LENGTH: 19
<212> TYPE: PRT
<213> ORGANISM: Unknown
<220> FEATURE:
<223> OTHER INFORMATION: peptide antigen
<220> FEATURE:
<221> NAME/KEY: MISC_FEATURE
<222> LOCATION: (17)..(17)
<223> OTHER INFORMATION: Lys is dimethylated

<400> SEQUENCE: 3

Cys Ala Lys Pro Val Lys Ala Ser Lys Pro Lys Lys Ala Lys Pro Val
1               5                   10                  15

Lys Pro Lys

<210> SEQ ID NO 4
<211> LENGTH: 364
<212> TYPE: DNA
<213> ORGANISM: Unknown
<220> FEATURE:
<223> OTHER INFORMATION: Clone A heavy chain variable domain -
      nucleotide

<400> SEQUENCE: 4
cagtcggtgg aggagtccgg gggtcgcctg gtcacgcctg ggacacccct gacactcacc      60
tgcacggtct ctggattctc cctcaataac tatgtgatga tgtgggtccg ccaggctcca     120
ggggaggggc tggaatggat cgctgccatt actactggcg gtaccacata ctacgcgaac     180
tgggcgaaag gccgattcac catctccaaa acctcgacca cggtggatct gaaaatcatc     240
agtccgacaa ccgaggacac ggccacctat ttctgcgcca gagatctta tggtgatact     300 agtgatgata tttgggatgc ttttgatccc tggggcccag gcaccctggt caccgtctcc     360
tcag                                                                  364

<210> SEQ ID NO 5
<211> LENGTH: 299
<212> TYPE: DNA
<213> ORGANISM: Unknown
<220> FEATURE:
<223> OTHER INFORMATION: Clone A light chain variable domain -
      nucleotide

<400> SEQUENCE: 5
gaccctgtgc tgacccagac tccatcgtcc gtgtctgcag ctgtgggagg cacagtcacc      60
atcagttgcc agtccagtga gagtgtttat aagaataaca acttagcctg gtatcagcag     120
aaaccagggc agcctcccaa gctcctgatc tattctgcat ccactctggc atctggggtc     180
ccatcgcggt tcaaaggcag tggatctggg acacagtcac tctcaccatc agtggcgtgc     240
agtgtgacga tgctgccact tactactgtc taggagtata tagtgatatt tttgctttc      299

<210> SEQ ID NO 6
<211> LENGTH: 121
<212> TYPE: PRT
<213> ORGANISM: Unknown
<220> FEATURE:
<223> OTHER INFORMATION: Clone A heavy chain variable domain

```
<400> SEQUENCE: 6

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Asn Tyr Val
            20                  25                  30

Met Met Trp Val Arg Gln Ala Pro Gly Glu Gly Leu Glu Trp Ile Ala
            35                  40                  45

Ala Ile Thr Thr Gly Gly Thr Thr Tyr Tyr Ala Asn Trp Ala Lys Gly
50                  55                  60

Arg Phe Thr Ile Ser Lys Thr Ser Thr Thr Val Asp Leu Lys Ile Ile
65                  70                  75                  80

Ser Pro Thr Thr Glu Asp Thr Ala Thr Tyr Phe Cys Ala Arg Asp Leu
            85                  90                  95

Tyr Gly Asp Thr Ser Asp Asp Ile Trp Asp Ala Phe Asp Pro Trp Gly
            100                 105                 110

Pro Gly Thr Leu Val Thr Val Ser Ser
            115                 120

<210> SEQ ID NO 7
<211> LENGTH: 103
<212> TYPE: PRT
<213> ORGANISM: Unknown
<220> FEATURE:
<223> OTHER INFORMATION: Clone B heavy chain variable domain

<400> SEQUENCE: 7

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asp Tyr Tyr
            20                  25                  30

Thr Thr Trp Val Arg Gln Ala Pro Gly Gln Gly Leu Glu Tyr Ile Gly
            35                  40                  45

Tyr Ile Ser Gly Thr Gly Thr Pro Tyr Tyr Ala Thr Trp Ala Lys Gly
50                  55                  60

Arg Phe Thr Ile Ser Arg Thr Ser Thr Thr Val Gly Leu Lys Met Thr
65                  70                  75                  80

Ser Leu Thr Thr Glu Asp Thr Ala Thr Tyr Phe Cys Ala Arg Ser Tyr
            85                  90                  95

Pro Gly Ile Asp Ala Asn Asn
            100

<210> SEQ ID NO 8
<211> LENGTH: 100
<212> TYPE: PRT
<213> ORGANISM: Unknown
<220> FEATURE:
<223> OTHER INFORMATION: Clone A light chain variable domain

<400> SEQUENCE: 8

Asp Pro Val Leu Thr Gln Thr Pro Ser Ser Val Ser Ala Ala Val Gly
1               5                   10                  15

Gly Thr Val Thr Ile Ser Cys Gln Ser Ser Glu Ser Val Tyr Lys Asn
            20                  25                  30

Asn Asn Leu Ala Trp Tyr Gln Gln Lys Pro Gly Gln Pro Pro Lys Leu
            35                  40                  45

Leu Ile Tyr Ser Ala Ser Thr Leu Ala Ser Gly Val Pro Ser Arg Phe
50                  55                  60
```

```
Lys Gly Ser Gly Ser Gly Thr Gln Phe Thr Leu Thr Ile Ser Gly Val
 65                  70                  75                  80

Gln Cys Asp Asp Ala Ala Thr Tyr Tyr Cys Leu Gly Val Tyr Ser Asp
                 85                  90                  95

Ile Phe Ala Phe
            100

<210> SEQ ID NO 9
<211> LENGTH: 101
<212> TYPE: PRT
<213> ORGANISM: Unknown
<220> FEATURE:
<223> OTHER INFORMATION: Clone B light chain variable domain

<400> SEQUENCE: 9

Ala Gln Val Leu Thr Gln Thr Pro Ser Ser Val Ser Ala Ala Val Gly
  1               5                  10                  15

Gly Thr Val Thr Ile Ser Cys Gln Ser Ser Gln Ser Val Tyr Asn Asn
                 20                  25                  30

Asn Tyr Leu Gly Trp Tyr Gln Gln Lys Pro Gly Gln Pro Pro Lys Leu
             35                  40                  45

Leu Ile Tyr Leu Ala Ser Thr Leu Ala Ser Gly Val Pro Ser Arg Phe
 50                  55                  60

Lys Gly Ser Gly Ser Gly Thr Gln Phe Thr Leu Thr Ile Ser Asp Leu
 65                  70                  75                  80

Glu Cys Asp Asp Ala Ala Thr Tyr Tyr Cys Gly Gly Asp Tyr Asp Val
                 85                  90                  95

Tyr Ile Ala Ala Phe
            100

<210> SEQ ID NO 10
<211> LENGTH: 13
<212> TYPE: PRT
<213> ORGANISM: Unknown
<220> FEATURE:
<223> OTHER INFORMATION: clone A CDR-L1

<400> SEQUENCE: 10

Gln Ser Ser Glu Ser Val Tyr Lys Asn Asn Asn Leu Ala
  1               5                  10

<210> SEQ ID NO 11
<211> LENGTH: 9
<212> TYPE: PRT
<213> ORGANISM: Unknown
<220> FEATURE:
<223> OTHER INFORMATION: clone A CDR-L1

<400> SEQUENCE: 11

Tyr Lys Asn Asn Asn Leu Ala Trp Tyr
  1               5

<210> SEQ ID NO 12
<211> LENGTH: 13
<212> TYPE: PRT
<213> ORGANISM: Unknown
<220> FEATURE:
<223> OTHER INFORMATION: clone B CDR-L1

<400> SEQUENCE: 12

Gln Ser Ser Gln Ser Val Tyr Asn Asn Asn Tyr Leu Gly
  1               5                  10
```

```
<210> SEQ ID NO 13
<211> LENGTH: 9
<212> TYPE: PRT
<213> ORGANISM: Unknown
<220> FEATURE:
<223> OTHER INFORMATION: clone B CDR-L1

<400> SEQUENCE: 13

Tyr Asn Asn Asn Tyr Leu Gly Trp Tyr
1               5

<210> SEQ ID NO 14
<211> LENGTH: 7
<212> TYPE: PRT
<213> ORGANISM: Unknown
<220> FEATURE:
<223> OTHER INFORMATION: clone A CDR-L2

<400> SEQUENCE: 14

Ser Ala Ser Thr Leu Ala Ser
1               5

<210> SEQ ID NO 15
<211> LENGTH: 10
<212> TYPE: PRT
<213> ORGANISM: Unknown
<220> FEATURE:
<223> OTHER INFORMATION: clone A CDR-L2

<400> SEQUENCE: 15

Leu Leu Ile Tyr Ser Ala Ser Thr Leu Ala
1               5                   10

<210> SEQ ID NO 16
<211> LENGTH: 7
<212> TYPE: PRT
<213> ORGANISM: Unknown
<220> FEATURE:
<223> OTHER INFORMATION: clone B CDR-L2

<400> SEQUENCE: 16

Leu Ala Ser Thr Leu Ala Ser
1               5

<210> SEQ ID NO 17
<211> LENGTH: 10
<212> TYPE: PRT
<213> ORGANISM: Unknown
<220> FEATURE:
<223> OTHER INFORMATION: clone B CDR-L2

<400> SEQUENCE: 17

Leu Leu Ile Tyr Leu Ala Ser Thr Leu Ala
1               5                   10

<210> SEQ ID NO 18
<211> LENGTH: 10
<212> TYPE: PRT
<213> ORGANISM: Unknown
<220> FEATURE:
<223> OTHER INFORMATION: clone A CDR-L3

<400> SEQUENCE: 18

Leu Gly Val Tyr Ser Asp Ile Phe Ala Phe
1               5                   10
```

```
<210> SEQ ID NO 19
<211> LENGTH: 10
<212> TYPE: PRT
<213> ORGANISM: Unknown
<220> FEATURE:
<223> OTHER INFORMATION: clone B CDR-L3

<400> SEQUENCE: 19

Gly Gly Asp Tyr Asp Val Tyr Ile Ala Ala
1               5                   10

<210> SEQ ID NO 20
<211> LENGTH: 7
<212> TYPE: PRT
<213> ORGANISM: Unknown
<220> FEATURE:
<223> OTHER INFORMATION: clone A CDR-H1

<400> SEQUENCE: 20

Gly Phe Ser Leu Asn Asn Tyr
1               5

<210> SEQ ID NO 21
<211> LENGTH: 10
<212> TYPE: PRT
<213> ORGANISM: Unknown
<220> FEATURE:
<223> OTHER INFORMATION: clone A CDR-H1

<400> SEQUENCE: 21

Gly Phe Ser Leu Asn Asn Tyr Val Met Met
1               5                   10

<210> SEQ ID NO 22
<211> LENGTH: 5
<212> TYPE: PRT
<213> ORGANISM: Unknown
<220> FEATURE:
<223> OTHER INFORMATION: clone A CDR-H1

<400> SEQUENCE: 22

Asn Tyr Val Met Met
1               5

<210> SEQ ID NO 23
<211> LENGTH: 6
<212> TYPE: PRT
<213> ORGANISM: Unknown
<220> FEATURE:
<223> OTHER INFORMATION: clone A CDR-H1

<400> SEQUENCE: 23

Asn Asn Tyr Val Met Met
1               5

<210> SEQ ID NO 24
<211> LENGTH: 7
<212> TYPE: PRT
<213> ORGANISM: Unknown
<220> FEATURE:
<223> OTHER INFORMATION: clone B CDR-H1

<400> SEQUENCE: 24

Gly Phe Ser Leu Ser Asp Tyr
1               5

<210> SEQ ID NO 25
```

```
<211> LENGTH: 10
<212> TYPE: PRT
<213> ORGANISM: Unknown
<220> FEATURE:
<223> OTHER INFORMATION: clone B CDR-H1

<400> SEQUENCE: 25

Gly Phe Ser Leu Ser Asp Tyr Tyr Thr Thr
1               5                   10

<210> SEQ ID NO 26
<211> LENGTH: 5
<212> TYPE: PRT
<213> ORGANISM: Unknown
<220> FEATURE:
<223> OTHER INFORMATION: clone B CDR-H1

<400> SEQUENCE: 26

Asp Tyr Tyr Thr Thr
1               5

<210> SEQ ID NO 27
<211> LENGTH: 6
<212> TYPE: PRT
<213> ORGANISM: Unknown
<220> FEATURE:
<223> OTHER INFORMATION: clone B CDR-H1

<400> SEQUENCE: 27

Ser Asp Tyr Tyr Thr Thr
1               5

<210> SEQ ID NO 28
<211> LENGTH: 5
<212> TYPE: PRT
<213> ORGANISM: Unknown
<220> FEATURE:
<223> OTHER INFORMATION: clone A CDR-H2

<400> SEQUENCE: 28

Thr Thr Gly Gly Thr
1               5

<210> SEQ ID NO 29
<211> LENGTH: 9
<212> TYPE: PRT
<213> ORGANISM: Unknown
<220> FEATURE:
<223> OTHER INFORMATION: clone A CDR-H2

<400> SEQUENCE: 29

Ala Ile Thr Thr Gly Gly Thr Thr Tyr
1               5

<210> SEQ ID NO 30
<211> LENGTH: 16
<212> TYPE: PRT
<213> ORGANISM: Unknown
<220> FEATURE:
<223> OTHER INFORMATION: clone A CDR-H2

<400> SEQUENCE: 30

Ala Ile Thr Thr Gly Gly Thr Thr Tyr Tyr Ala Asn Trp Ala Lys Gly
1               5                   10                  15

<210> SEQ ID NO 31
<211> LENGTH: 12
```

```
<212> TYPE: PRT
<213> ORGANISM: Unknown
<220> FEATURE:
<223> OTHER INFORMATION: clone A CDR-H2

<400> SEQUENCE: 31

Trp Ile Ala Ala Ile Thr Thr Gly Gly Thr Thr Tyr
1               5                   10

<210> SEQ ID NO 32
<211> LENGTH: 5
<212> TYPE: PRT
<213> ORGANISM: Unknown
<220> FEATURE:
<223> OTHER INFORMATION: clone B CDR-H2

<400> SEQUENCE: 32

Ser Gly Thr Gly Thr
1               5

<210> SEQ ID NO 33
<211> LENGTH: 9
<212> TYPE: PRT
<213> ORGANISM: Unknown
<220> FEATURE:
<223> OTHER INFORMATION: clone B CDR-H2

<400> SEQUENCE: 33

Tyr Ile Ser Gly Thr Gly Thr Pro Tyr
1               5

<210> SEQ ID NO 34
<211> LENGTH: 16
<212> TYPE: PRT
<213> ORGANISM: Unknown
<220> FEATURE:
<223> OTHER INFORMATION: clone B CDR-H2

<400> SEQUENCE: 34

Tyr Ile Ser Gly Thr Gly Thr Pro Tyr Tyr Ala Thr Trp Ala Lys Gly
1               5                   10                  15

<210> SEQ ID NO 35
<211> LENGTH: 12
<212> TYPE: PRT
<213> ORGANISM: Unknown
<220> FEATURE:
<223> OTHER INFORMATION: clone B CDR-H2

<400> SEQUENCE: 35

Tyr Ile Gly Tyr Ile Ser Gly Thr Gly Thr Pro Tyr
1               5                   10

<210> SEQ ID NO 36
<211> LENGTH: 16
<212> TYPE: PRT
<213> ORGANISM: Unknown
<220> FEATURE:
<223> OTHER INFORMATION: clone A CDR-H3

<400> SEQUENCE: 36

Asp Leu Tyr Gly Asp Thr Ser Asp Asp Ile Trp Asp Ala Phe Asp Pro
1               5                   10                  15

<210> SEQ ID NO 37
<211> LENGTH: 18
<212> TYPE: PRT
```

```
<213> ORGANISM: Unknown
<220> FEATURE:
<223> OTHER INFORMATION: clone A CDR-H3

<400> SEQUENCE: 37

Ala Arg Asp Leu Tyr Gly Asp Thr Ser Asp Ile Trp Asp Ala Phe
1               5                   10                  15

Asp Pro

<210> SEQ ID NO 38
<211> LENGTH: 23
<212> TYPE: PRT
<213> ORGANISM: Unknown
<220> FEATURE:
<223> OTHER INFORMATION: clone A LFR1

<400> SEQUENCE: 38

Asp Pro Val Leu Thr Gln Thr Pro Ser Ser Val Ser Ala Ala Val Gly
1               5                   10                  15

Gly Thr Val Thr Ile Ser Cys
            20

<210> SEQ ID NO 39
<211> LENGTH: 29
<212> TYPE: PRT
<213> ORGANISM: Unknown
<220> FEATURE:
<223> OTHER INFORMATION: clone A LFR1

<400> SEQUENCE: 39

Asp Pro Val Leu Thr Gln Thr Pro Ser Ser Val Ser Ala Ala Val Gly
1               5                   10                  15

Gly Thr Val Thr Ile Ser Cys Gln Ser Ser Glu Ser Val
            20                  25

<210> SEQ ID NO 40
<211> LENGTH: 15
<212> TYPE: PRT
<213> ORGANISM: Unknown
<220> FEATURE:
<223> OTHER INFORMATION: clone A LFR2

<400> SEQUENCE: 40

Trp Tyr Gln Gln Lys Pro Gly Gln Pro Pro Lys Leu Leu Ile Tyr
1               5                   10                  15

<210> SEQ ID NO 41
<211> LENGTH: 9
<212> TYPE: PRT
<213> ORGANISM: Unknown
<220> FEATURE:
<223> OTHER INFORMATION: clone A LFR2

<400> SEQUENCE: 41

Gln Gln Lys Pro Gly Gln Pro Pro Lys
1               5

<210> SEQ ID NO 42
<211> LENGTH: 32
<212> TYPE: PRT
<213> ORGANISM: Unknown
<220> FEATURE:
<223> OTHER INFORMATION: clone A LFR3

<400> SEQUENCE: 42
```

Gly Val Pro Ser Arg Phe Lys Gly Ser Gly Ser Gly Thr Gln Phe Thr
1               5                   10                  15

Leu Thr Ile Ser Gly Val Gln Cys Asp Asp Ala Ala Thr Tyr Tyr Cys
            20                  25                  30

<210> SEQ ID NO 43
<211> LENGTH: 33
<212> TYPE: PRT
<213> ORGANISM: Unknown
<220> FEATURE:
<223> OTHER INFORMATION: clone A LFR3

<400> SEQUENCE: 43

Ser Gly Val Pro Ser Arg Phe Lys Gly Ser Gly Ser Gly Thr Gln Phe
1               5                   10                  15

Thr Leu Thr Ile Ser Gly Val Gln Cys Asp Asp Ala Ala Thr Tyr Tyr
            20                  25                  30

Cys

<210> SEQ ID NO 44
<211> LENGTH: 24
<212> TYPE: PRT
<213> ORGANISM: Unknown
<220> FEATURE:
<223> OTHER INFORMATION: clone A HFR1

<400> SEQUENCE: 44

Gln Ser Val Glu Glu Ser Gly Gly Arg Leu Val Thr Pro Gly Thr Pro
1               5                   10                  15

Leu Thr Leu Thr Cys Thr Val Ser
            20

<210> SEQ ID NO 45
<211> LENGTH: 29
<212> TYPE: PRT
<213> ORGANISM: Unknown
<220> FEATURE:
<223> OTHER INFORMATION: clone A HFR1

<400> SEQUENCE: 45

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn
            20                  25

<210> SEQ ID NO 46
<211> LENGTH: 28
<212> TYPE: PRT
<213> ORGANISM: Unknown
<220> FEATURE:
<223> OTHER INFORMATION: clone A HFR1

<400> SEQUENCE: 46

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu
            20                  25

<210> SEQ ID NO 47
<211> LENGTH: 19
<212> TYPE: PRT
<213> ORGANISM: Unknown
<220> FEATURE:
<223> OTHER INFORMATION: clone A HFR2

<400> SEQUENCE: 47

Val Met Met Trp Val Arg Gln Ala Pro Gly Glu Gly Leu Glu Trp Ile
1               5                   10                  15

Ala Ala Ile

<210> SEQ ID NO 48
<211> LENGTH: 14
<212> TYPE: PRT
<213> ORGANISM: Unknown
<220> FEATURE:
<223> OTHER INFORMATION: clone A HFR2

<400> SEQUENCE: 48

Trp Val Arg Gln Ala Pro Gly Glu Gly Leu Glu Trp Ile Ala
1               5                   10

<210> SEQ ID NO 49
<211> LENGTH: 11
<212> TYPE: PRT
<213> ORGANISM: Unknown
<220> FEATURE:
<223> OTHER INFORMATION: clone A HFR2

<400> SEQUENCE: 49

Trp Val Arg Gln Ala Pro Gly Glu Gly Leu Glu
1               5                   10

<210> SEQ ID NO 50
<211> LENGTH: 39
<212> TYPE: PRT
<213> ORGANISM: Unknown
<220> FEATURE:
<223> OTHER INFORMATION: clone A HFR3

<400> SEQUENCE: 50

Thr Tyr Tyr Ala Asn Trp Ala Lys Gly Arg Phe Thr Ile Ser Lys Thr
1               5                   10                  15

Ser Thr Thr Val Asp Leu Lys Ile Ile Ser Pro Thr Thr Glu Asp Thr
            20                  25                  30

Ala Thr Tyr Phe Cys Ala Arg
        35

<210> SEQ ID NO 51
<211> LENGTH: 37
<212> TYPE: PRT
<213> ORGANISM: Unknown
<220> FEATURE:
<223> OTHER INFORMATION: clone A HFR3

<400> SEQUENCE: 51

Tyr Ala Asn Trp Ala Lys Gly Arg Phe Thr Ile Ser Lys Thr Ser Thr
1               5                   10                  15

Thr Val Asp Leu Lys Ile Ile Ser Pro Thr Thr Glu Asp Thr Ala Thr
            20                  25                  30

Tyr Phe Cys Ala Arg
        35

<210> SEQ ID NO 52
<211> LENGTH: 30
<212> TYPE: PRT
<213> ORGANISM: Unknown
<220> FEATURE:
<223> OTHER INFORMATION: clone A HFR3

<400> SEQUENCE: 52

Arg Phe Thr Ile Ser Lys Thr Ser Thr Val Asp Leu Lys Ile Ile
1               5                   10                  15

Ser Pro Thr Thr Glu Asp Thr Ala Thr Tyr Phe Cys Ala Arg
            20                  25                  30

<210> SEQ ID NO 53
<211> LENGTH: 35
<212> TYPE: PRT
<213> ORGANISM: Unknown
<220> FEATURE:
<223> OTHER INFORMATION: clone A HFR3

<400> SEQUENCE: 53

Tyr Ala Asn Trp Ala Lys Gly Arg Phe Thr Ile Ser Lys Thr Ser Thr
1               5                   10                  15

Thr Val Asp Leu Lys Ile Ile Ser Pro Thr Thr Glu Asp Thr Ala Thr
            20                  25                  30

Tyr Phe Cys
        35

<210> SEQ ID NO 54
<211> LENGTH: 11
<212> TYPE: PRT
<213> ORGANISM: Unknown
<220> FEATURE:
<223> OTHER INFORMATION: clone A HFR4

<400> SEQUENCE: 54

Trp Gly Pro Gly Thr Leu Val Thr Val Ser Ser
1               5                   10

<210> SEQ ID NO 55
<211> LENGTH: 12
<212> TYPE: PRT
<213> ORGANISM: Unknown
<220> FEATURE:
<223> OTHER INFORMATION: clone A HFR4

<400> SEQUENCE: 55

Pro Trp Gly Pro Gly Thr Leu Val Thr Val Ser Ser
1               5                   10

<210> SEQ ID NO 56
<211> LENGTH: 23
<212> TYPE: PRT
<213> ORGANISM: Unknown
<220> FEATURE:
<223> OTHER INFORMATION: clone B LFR1

<400> SEQUENCE: 56

Ala Gln Val Leu Thr Gln Thr Pro Ser Ser Val Ser Ala Ala Val Gly
1               5                   10                  15

Gly Thr Val Thr Ile Ser Cys
            20

<210> SEQ ID NO 57
<211> LENGTH: 29
<212> TYPE: PRT
<213> ORGANISM: Unknown
<220> FEATURE:
<223> OTHER INFORMATION: clone B LFR1

<400> SEQUENCE: 57

Ala Gln Val Leu Thr Gln Thr Pro Ser Ser Val Ser Ala Val Gly
1               5                   10                  15

Gly Thr Val Thr Ile Ser Cys Gln Ser Ser Gln Ser Val
            20                  25

<210> SEQ ID NO 58
<211> LENGTH: 15
<212> TYPE: PRT
<213> ORGANISM: Unknown
<220> FEATURE:
<223> OTHER INFORMATION: clone B LFR2

<400> SEQUENCE: 58

Trp Tyr Gln Gln Lys Pro Gly Gln Pro Pro Lys Leu Leu Ile Tyr
1               5                   10                  15

<210> SEQ ID NO 59
<211> LENGTH: 9
<212> TYPE: PRT
<213> ORGANISM: Unknown
<220> FEATURE:
<223> OTHER INFORMATION: clone B LFR2

<400> SEQUENCE: 59

Gln Gln Lys Pro Gly Gln Pro Pro Lys
1               5

<210> SEQ ID NO 60
<211> LENGTH: 32
<212> TYPE: PRT
<213> ORGANISM: Unknown
<220> FEATURE:
<223> OTHER INFORMATION: clone B LFR3

<400> SEQUENCE: 60

Gly Val Pro Ser Arg Phe Lys Gly Ser Gly Ser Gly Thr Gln Phe Thr
1               5                   10                  15

Leu Thr Ile Ser Asp Leu Glu Cys Asp Asp Ala Ala Thr Tyr Tyr Cys
            20                  25                  30

<210> SEQ ID NO 61
<211> LENGTH: 33
<212> TYPE: PRT
<213> ORGANISM: Unknown
<220> FEATURE:
<223> OTHER INFORMATION: clone B LFR3

<400> SEQUENCE: 61

Ser Gly Val Pro Ser Arg Phe Lys Gly Ser Gly Ser Gly Thr Gln Phe
1               5                   10                  15

Thr Leu Thr Ile Ser Asp Leu Glu Cys Asp Asp Ala Ala Thr Tyr Tyr
            20                  25                  30

Cys

<210> SEQ ID NO 62
<211> LENGTH: 24
<212> TYPE: PRT
<213> ORGANISM: Unknown
<220> FEATURE:
<223> OTHER INFORMATION: clone B HFR1

<400> SEQUENCE: 62

Gln Ser Leu Glu Glu Ser Gly Gly Arg Leu Val Thr Pro Gly Thr Pro
1               5                   10                  15

```
Leu Thr Leu Thr Cys Thr Ala Ser
            20

<210> SEQ ID NO 63
<211> LENGTH: 29
<212> TYPE: PRT
<213> ORGANISM: Unknown
<220> FEATURE:
<223> OTHER INFORMATION: clone B HFR1

<400> SEQUENCE: 63

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser
            20                  25

<210> SEQ ID NO 64
<211> LENGTH: 28
<212> TYPE: PRT
<213> ORGANISM: Unknown
<220> FEATURE:
<223> OTHER INFORMATION: clone B HFR1

<400> SEQUENCE: 64

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu
            20                  25

<210> SEQ ID NO 65
<211> LENGTH: 19
<212> TYPE: PRT
<213> ORGANISM: Unknown
<220> FEATURE:
<223> OTHER INFORMATION: clone B HFR2

<400> SEQUENCE: 65

Tyr Thr Thr Trp Val Arg Gln Ala Pro Gly Gln Gly Leu Glu Tyr Ile
1               5                   10                  15

Gly Tyr Ile

<210> SEQ ID NO 66
<211> LENGTH: 14
<212> TYPE: PRT
<213> ORGANISM: Unknown
<220> FEATURE:
<223> OTHER INFORMATION: clone B HFR2

<400> SEQUENCE: 66

Trp Val Arg Gln Ala Pro Gly Gln Gly Leu Glu Tyr Ile Gly
1               5                   10

<210> SEQ ID NO 67
<211> LENGTH: 11
<212> TYPE: PRT
<213> ORGANISM: Unknown
<220> FEATURE:
<223> OTHER INFORMATION: clone B HFR2

<400> SEQUENCE: 67

Trp Val Arg Gln Ala Pro Gly Gln Gly Leu Glu
1               5                   10

<210> SEQ ID NO 68
```

```
<211> LENGTH: 39
<212> TYPE: PRT
<213> ORGANISM: Unknown
<220> FEATURE:
<223> OTHER INFORMATION: clone B HFR3

<400> SEQUENCE: 68

Pro Tyr Tyr Ala Thr Trp Ala Lys Gly Arg Phe Thr Ile Ser Arg Thr
1               5                   10                  15

Ser Thr Thr Val Gly Leu Lys Met Thr Ser Leu Thr Thr Glu Asp Thr
            20                  25                  30

Ala Thr Tyr Phe Cys Ala Arg
        35

<210> SEQ ID NO 69
<211> LENGTH: 37
<212> TYPE: PRT
<213> ORGANISM: Unknown
<220> FEATURE:
<223> OTHER INFORMATION: clone B HFR3

<400> SEQUENCE: 69

Tyr Ala Thr Trp Ala Lys Gly Arg Phe Thr Ile Ser Arg Thr Ser Thr
1               5                   10                  15

Thr Val Gly Leu Lys Met Thr Ser Leu Thr Thr Glu Asp Thr Ala Thr
            20                  25                  30

Tyr Phe Cys Ala Arg
        35

<210> SEQ ID NO 70
<211> LENGTH: 30
<212> TYPE: PRT
<213> ORGANISM: Unknown
<220> FEATURE:
<223> OTHER INFORMATION: clone B HFR3

<400> SEQUENCE: 70

Arg Phe Thr Ile Ser Arg Thr Ser Thr Thr Val Gly Leu Lys Met Thr
1               5                   10                  15

Ser Leu Thr Thr Glu Asp Thr Ala Thr Tyr Phe Cys Ala Arg
            20                  25                  30

<210> SEQ ID NO 71
<211> LENGTH: 35
<212> TYPE: PRT
<213> ORGANISM: Unknown
<220> FEATURE:
<223> OTHER INFORMATION: clone B HFR3

<400> SEQUENCE: 71

Tyr Ala Thr Trp Ala Lys Gly Arg Phe Thr Ile Ser Arg Thr Ser Thr
1               5                   10                  15

Thr Val Gly Leu Lys Met Thr Ser Leu Thr Thr Glu Asp Thr Ala Thr
            20                  25                  30

Tyr Phe Cys
        35

<210> SEQ ID NO 72
<211> LENGTH: 19
<212> TYPE: PRT
<213> ORGANISM: Unknown
<220> FEATURE:
<223> OTHER INFORMATION: Keyhole Limpet Hemocyanin (KLH)-conjugated
      H1.0K180me2 peptide
```

```
<220> FEATURE:
<221> NAME/KEY: MISC_FEATURE
<222> LOCATION: (1)..(1)
<223> OTHER INFORMATION: conjugated to Keyhole Limpet Hemocyanin
<220> FEATURE:
<221> NAME/KEY: MISC_FEATURE
<222> LOCATION: (17)..(17)
<223> OTHER INFORMATION: Lys is dimethylated

<400> SEQUENCE: 72

Cys Ala Lys Pro Val Lys Ala Ser Lys Pro Lys Lys Ala Lys Pro Val
1               5                   10                  15

Lys Pro Lys

<210> SEQ ID NO 73
<211> LENGTH: 19
<212> TYPE: PRT
<213> ORGANISM: Unknown
<220> FEATURE:
<223> OTHER INFORMATION: biotin-conjugated H1.0K180me2 peptide
<220> FEATURE:
<221> NAME/KEY: MISC_FEATURE
<222> LOCATION: (1)..(1)
<223> OTHER INFORMATION: conjugated to a biotin moiety
<220> FEATURE:
<221> NAME/KEY: MISC_FEATURE
<222> LOCATION: (17)..(17)
<223> OTHER INFORMATION: Lys is dimethylated

<400> SEQUENCE: 73

Cys Ala Lys Pro Val Lys Ala Ser Lys Pro Lys Lys Ala Lys Pro Val
1               5                   10                  15

Lys Pro Lys

<210> SEQ ID NO 74
<211> LENGTH: 19
<212> TYPE: PRT
<213> ORGANISM: Unknown
<220> FEATURE:
<223> OTHER INFORMATION: biotin-conjugated unmethylated H1.0 peptide
<220> FEATURE:
<221> NAME/KEY: MISC_FEATURE
<222> LOCATION: (1)..(1)
<223> OTHER INFORMATION: conjugated to a biotin moiety

<400> SEQUENCE: 74

Cys Ala Lys Pro Val Lys Ala Ser Lys Pro Lys Lys Ala Lys Pro Val
1               5                   10                  15

Lys Pro Lys
```

H1.0K180ME2 ANTIBODIES, METHODS OF MAKING AND USES THEREOF

CROSS-REFERENCE TO RELATED APPLICATIONS

This application is a continuation of International Patent Application No. PCT/US2018/057602, filed on Oct. 25, 2018, which claims priority to U.S. Provisional Application Ser. No. 62/577,041, filed on Oct. 25, 2017, the contents of each of which is incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ALNC_010_01US_SeqList_ST25.txt, date recorded: Apr. 23, 2020, file size 27 kilobytes).

BACKGROUND

Cellular chromatin is a dynamic polymer, capable of many configurations, and prone to remodeling and restructuring as it receives physiologically relevant input. Histone proteins are the main protein components of chromatin and double-stranded DNA is wound around histone proteins. Changes in histone proteins can differentially alter access of the transcriptional machinery to some genes while leaving access to other genes intact. Differential chromatin condensation achieved by histone posttranslational modifications (PTMs) underlies packaging of chromatin (Lunyak and Rosenfeld 92008) *Hum. Mol. Genet.*, 17: R28-36; Jenuwein and Allis (2001) *Science,* 293: 1074-1080). Histone PTMs, for example methylation, can act as an epigenetic code and play critical roles in many aspects of the cellular responses tightly linked to development, injury, disease and aging.

Five major families of histones exist: H1, H2A, H2B, H3 and H4. Histones H2A, H2B, H3 and H4 are known as the core histones, while histones H1 and H5 are known as the linker histones. The large number of H1.0-binding proteins identified by multiple studies in recent years point to an important role for protein—protein interactions of H1.0 and suggests a new paradigm for H1.0 structure and function that extends beyond its effects on chromatin architecture.

There is a need to detect H1.0 methylation in various cellular contexts; and sensitive assays are needed to differentiate among the various types of cellular contexts, as they relate to the development of disease, response to injury, and response to therapeutic regimens. There is also a need to therapeutically address methylated H1.0-related diseases and conditions. Provided herein are methods and compositions for this purpose.

SUMMARY

Provided herein are antibodies that bind a protein comprising an H1.0K180me2 antigen, or a peptide thereof, wherein the antibodies are useful for therapeutics and diagnostics. Also provided are methods of making such antibodies.

Accordingly, in one aspect, provided herein is an antibody that specifically binds a protein comprising an H1.0K180me2 antigen or a peptide thereof, wherein the antigen-binding domain of the antibody comprises:

(a) any one of the CDR-L1 amino acid sequences of Table 4;
(b) any one of the CDR-L2 amino acid sequences of Table 5; and
(c) any one of the CDR-L3 amino acid sequences of Table 6.

In another aspect, provided herein is an antibody that specifically binds a protein comprising an H1.0K180me2 antigen or a peptide thereof, wherein the antigen-binding domain of the antibody comprises:

(a) any one of the CDR-H1 amino acid sequences of Table 7;
(b) any one of the CDR-H2 amino acid sequences of Table 8; and
(c) any one of the CDR-H3 amino acid sequences of Table 9.

In another aspect, provided herein is an antibody that specifically binds a protein comprising an H1.0K180me2 antigen or a peptide thereof, wherein the antigen-binding domain of the antibody comprises any one of the CDR-L amino acid sequences of Tables 4, 5, and 6, and comprises any one of the CDR-H amino acid sequences of Tables 7, 8, and 9.

In another aspect, provided herein is an antibody that specifically binds a protein comprising an H1.0K180me2 antigen or a peptide thereof, wherein the antigen-binding domain of the H1.0K180me2 antibody comprises:

(a) a CDR-L1 comprising the amino acid sequence of SEQ ID NO: 10 or SEQ ID NO: 11;
(b) a CDR-L2 comprising the amino acid sequence of SEQ ID NO: 14 or SEQ ID NO: 15; and
(c) a CDR-L3 comprising the amino acid sequence of SEQ ID NO: 18.

In another aspect, provided herein is an antibody that specifically binds a protein comprising an H1.0K180me2 antigen or a peptide thereof, wherein the antigen-binding domain of the H1.0K180me2 antibody comprises:

(a) a CDR-H1 comprising the amino acid sequence of SEQ ID NO: 20, SEQ ID NO: 21, SEQ ID NO: 22 or SEQ ID NO: 23;
(b) a CDR-H2 comprising the amino acid sequence of SEQ ID NO: 28, SEQ ID NO: 29, SEQ ID NO: 30 or SEQ ID NO: 31; and
(c) a CDR-H3 comprising the amino acid sequence of SEQ ID NO: 36 or SEQ ID NO: 37.

In another aspect, provided herein is an antibody that specifically binds a protein comprising an H1.0K180me2 antigen or a peptide thereof, wherein the light chain variable domain of the antibody comprises the amino acid sequence of SEQ ID NO: 8 or SEQ ID NO: 9.

In another aspect, provided herein is an antibody that specifically binds a protein comprising an H1.0K180me2 antigen or a peptide thereof, wherein the heavy chain variable domain of the antibody comprises the amino acid sequence of SEQ ID NO: 6 or SEQ ID NO: 7.

In another aspect, provided herein is an antibody that specifically binds a protein comprising an H1.0K180me2 antigen or a peptide thereof, wherein the heavy chain variable domain of the antibody comprises the amino acid sequence of SEQ ID NO: 6 or SEQ ID NO: 7 and the light chain variable domain of the antibody comprises the amino acid sequence of SEQ ID NO: 8 or SEQ ID NO: 9.

In another aspect, provided herein is an antibody that specifically binds a protein comprising an H1.0K180me2 antigen or a peptide thereof, wherein the heavy chain variable domain of the antibody comprises the amino acid sequence of SEQ ID NO: 6 and the light chain variable domain of the antibody comprises the amino acid sequence of SEQ ID NO: 8.

In another aspect, provided herein is an antibody that specifically binds a protein comprising an H1.0K180me2 antigen or a peptide thereof, wherein the heavy chain variable domain of the antibody comprises the amino acid sequence of SEQ ID NO: 7 and the light chain variable domain of the antibody comprises the amino acid sequence of SEQ ID NO: 9.

In some embodiments, the antibody is chimeric or humanized. In some embodiments, the antibody is a monoclonal antibody. In some embodiments, the antibody is an antigen-binding fragment.

In some embodiments, the antibody exhibits reduced binding to the H1.0K180me2 protein or peptide, if the protein or peptide comprises residues other than K180 that are methylated. In some embodiments, the antibody does not bind, or only minimally binds, if the H1.0K180me2 protein or peptide comprises methylated lysine residues at lysine residues corresponding to K166, K172, K174, K175, and/or K177 of a human histone H1.0 protein.

In some embodiments, the antibody is conjugated to a label. In some embodiments, the antibody is attached to solid surface. In some embodiments, the antibody attached a bead, column, resin, or a microplate. In some embodiments, the antibody is conjugated to an agent. In some embodiments, the agent is selected from the group consisting of a radionuclide, a cytotoxin, a chemotherapeutic agent, a drug, a pro-drug, a toxin, an enzyme, an immunomodulator, a pro-apoptotic agent, a cytokine, a hormone, an oligonucleotide, an antisense molecule, a siRNA, and a second antibody.

In another aspect, provided herein is a vector encoding any one of the antibodies provided herein. In some embodiments, the vector comprises the nucleic acid of SEQ ID NO: 4 or the nucleic acid of SEQ ID NO: 5. In a related aspect, provided herein is a cell comprising one or more of these vectors.

In another aspect, provided herein is a method of determining whether an individual has, or is at risk of, developing, Alzheimer's disease, comprising:
(a) contacting a biological sample from the individual with the any one of the antibodies described herein; and
(b) determining the concentration of the protein comprising an H1.0K180me2 antigen or a peptide thereof in the sample that binds the antibody, wherein a decrease in the concentration relative to a control indicates that the individual has, or is at risk of developing, Alzheimer's disease. In some embodiments, the method further comprises treating the individual with an Alzheimer's disease drug or regimen if it is determined that the individual has, or is at risk of developing, Alzheimer's disease.

In another aspect, provided herein is a method of determining whether an individual diagnosed with Alzheimer's disease and receiving treatment for the Alzheimer's disease, will benefit from the treatment or will continue to benefit from the treatment, the method comprising:
(a) contacting a biological sample from the individual with the any one of the antibodies described herein; and
(b) determining the concentration of the protein comprising an H1.0K180me2 antigen or a peptide thereof in the sample that binds the antibody; and
(c) determining that the individual will benefit from the treatment or will continue to benefit from the treatment if there is an increase in the concentration, relative to a control. In some embodiments, the method further comprises treating the individual with an Alzheimer's disease drug or regimen if it is determined that the individual will benefit or continue to benefit from the treatment.

In another aspect, provided herein is a method of determining whether an individual diagnosed with Alzheimer's disease will benefit from a candidate treatment, wherein the individual has not yet started the treatment, the method comprising:
(a) administering to the individual a candidate treatment;
(b) contacting a biological sample from the individual after administration of the candidate treatment with the any one of the antibodies described herein; and
(c) determining the concentration and/or subcellular localization of the protein comprising an H1.0K180me2 antigen or a peptide thereof in the sample that binds the antibody; and
(d) determining that the individual will benefit from the candidate treatment if there is an increase in the concentration or an decrease in cytoplasmic subcellular localization, relative to a control. In some embodiments, the treatment is selected from the group consisting of APP synthesis Inhibitors, beta-secretase inhibitors, gamma-secretase inhibitors and modulators, AB aggregation inhibitors, AB immunotherapy, Cholesterol-lowering drugs, Anti-tau drugs, cholinesterase inhibitors, N-methyl D-aspartate (NMDA) antagonists, atypical antipsychotics, blockers of protein S-nitrosylation, glucagon-like peptide-1 receptor agonists, rapamycin, rapalogues, endocannabinoids, cannabionoids, neuroprotectors, molecules controlling calcium influx, antioxidants, anti-inflammatory drugs, drugs controlling control of glutamate homeostasis, autophagy inducers, hormones, hormonal regulators, statins, insulin, insulin carriers, multifunctional nanocarriers, vitamins, nutritional supplements, small RNA molecules, peptides, and ultrasound therapy.

In another aspect, provided herein is a method of determining whether an individual diagnosed with Alzheimer's disease will benefit from a candidate treatment, the method comprising:
(a) providing a biological sample obtained from the individual after administration of the candidate treatment;
(b) contacting the biological sample from the individual with the any one of the antibodies described herein; and
(c) determining the concentration and/or subcellular localization of the protein comprising an H1.0K180me2 antigen or a peptide thereof in the sample that binds the antibody; and
(d) determining that the individual will benefit from the candidate treatment if there is an increase in the concentration or an decrease in cytoplasmic subcellular localization, relative to a control. In some embodiments, the treatment is selected from the group consisting of APP synthesis Inhibitors, beta-secretase inhibitors, gamma-secretase inhibitors and modulators, AB aggregation inhibitors, AB immunotherapy, Cholesterol-lowering drugs, Anti-tau drugs, cholinesterase inhibitors, N-methyl D-aspartate (NMDA) antagonists, atypical antipsychotics, blockers of protein S-nitrosylation, glucagon-like peptide-1 receptor agonists, rapamycin, rapalogues, endocannabinoids, cannabionoids, neuroprotectors, molecules controlling calcium influx, antioxidants, anti-inflammatory drugs, drugs controlling control of glutamate homeostasis, autophagy inducers, hormones, hormonal regulators, statins, insulin, insulin carriers, multifunctional nanocarriers, vitamins, nutritional supplements, small RNA molecules, peptides, and ultrasound therapy.

In another aspect, provided herein is a method of determining whether an individual diagnosed with Alzheimer's disease will benefit from a candidate treatment, wherein the individual has not yet started the treatment, the method comprising:

(a) contacting a biological sample from the individual with a candidate treatment;

(b) contacting a biological sample from the individual with the any one of the antibodies described herein;

(c) determining the concentration and/or subcellular localization of the protein comprising an H1.0K180me2 antigen or a peptide thereof in the sample that binds the antibody; and (d) determining that the individual will benefit from the candidate treatment if there is an increase in the concentration relative to a control or an decrease in cytoplasmic subcellular localization, relative to a control. In some embodiments, the treatment is selected from the group consisting of APP synthesis Inhibitors, beta-secretase inhibitors, gamma-secretase inhibitors and modulators, AB aggregation inhibitors, AB immunotherapy, Cholesterol-lowering drugs, Anti-tau drugs, cholinesterase inhibitors, N-methyl D-aspartate (NMDA) antagonists, atypical antipsychotics, blockers of protein S-nitrosylation, glucagon-like peptide-1 receptor agonists, rapamycin, rapalogues, endocannabinoids, cannabionoids, neuroprotectors, molecules controlling calcium influx, antioxidants, anti-inflammatory drugs, drugs controlling control of glutamate homeostasis, autophagy inducers, hormones, hormonal regulators, statins, insulin, insulin carriers, multifunctional nanocarriers, vitamins, nutritional supplements, small RNA molecules, peptides, and ultrasound therapy.

In another aspect, provided herein is a method of determining whether an individual has been exposed to a DNA damaging agent, comprising:

(a) contacting a biological sample from the individual with the any one of the antibodies described herein; and (b) determining the concentration of the protein comprising an H1.0K180me2 antigen or a peptide thereof in the sample that binds the antibody, wherein an increase in the concentration relative to a control indicates that the individual has been exposed to a DNA damaging agent. In some embodiments, the DNA damaging agent is radiation.

In another aspect, provided herein is a method of determining whether an individual receiving treatment with a rapalogue is responsive to such treatment, comprising:

(a) contacting a biological sample from the individual with the any one of the antibodies described herein;

(b) determining the concentration of the protein comprising an H1.0K180me2 antigen or a peptide thereof in the sample that binds the antibody; and (c) determining whether the individual is responsive to treatment, wherein a decrease in the concentration relative to a control indicates that the individual is responsive.

In some embodiments, the rapalogue is selected from the group consisting of Rapamycin, Sirolimus, Rapamune, Everolimus, RA 001, Afinitor, Zortress, Temsirolimus, CCI-779, Torisel, Ridaforolimus, AP23573, MK-8669, Deforolimus, Zotarolimus, ABT-578, AZD8055, AZD2014, OSI-027, MLN0128, WYE-132, Torin1, PI-103, P7170, PF-04691502, PF-05212384, PKI-587, GNE477, PKI-180, WJD008, XL765, SAR245409, NVP-BEZ235, BGT226, SF1126, GSK2126458, Ku-0063794, WYE-354, NVP-BEZ235, PF-05212384, XL765, Torin 2, WYE-125132, and OSI-027.

In some embodiments of any one of the diagnostic methods provided herein, the increase or decrease in the concentration is above or below a threshold established by a Receiver Operating Characteristic curve analysis for optimal specificity and sensitivity. In some embodiments, the biological sample is selected from the group consisting of whole blood, plasma, serum, saliva, urine, synovial fluid, cerebrospinal fluid, bronchial lavage, ascites fluid, bone marrow aspirate, pleural effusion, tissue, cells, a biopsy, interstitial fluid, and lymphatic fluid.

In another aspect, provided herein is a method of treating a methylated H1.0-related disease or condition in an individual comprising administering to the individual a therapeutically effective amount of any one of the antibodies described herein. In some embodiments, the disease or condition is selected from the group consisting of Alzheimer's disease, radiation exposure, exposure to a genotoxic stressor, a disease or condition comprising the accumulation of senescent cells, and a disease or condition accompanied by elevated levels of H1.0K180me2 proteins or peptides.

In another aspect, provided herein is a method of clearing H1.0K180me2 in an individual comprising administering to the individual a therapeutically effective amount of any one of the antibodies described herein. In some embodiments, the individual suffers from a disease or condition selected from the group consisting of Alzheimer's disease, radiation exposure, exposure to a genotoxin, exposure to a DNA damaging agent, and a condition comprising the accumulation of senescent cells.

In another aspect, provided herein is a transdermal patch for measuring a concentration of a hypodermal target molecule, comprising:

(a) a substrate comprising the any one of the antibodies described herein; and (b) a plurality of microneedles.

In some embodiments, the patch is a transdermal microneedle array patch. In some embodiments, the substrate is elastically stretchable.

In another aspect, provided herein is a portable unit for determining whether an individual has been exposed to radiation or a DNA-damaging agent, comprising:

(a) a sample collection unit;

(b) a reader;

(c) an assay module comprising any one of the antibodies described herein; and (d) a plurality of microneedles.

In another aspect, provided herein is a test strip suitable for a lateral flow assay of an analyte, comprising a sample receiving zone, wherein the sample receiving zone comprises any one of the antibodies described herein.

In another aspect, provided herein is a pharmaceutical composition comprising any of the antibodies provided herein. The pharmaceutical composition may further comprise a pharmaceutically acceptable excipient.

In another aspect, provided herein is a kit comprising a therapeutically effective amount of any one of the antibodies provided herein.

In another aspect, provided herein is an article of manufacture comprising any one of antibodies or compositions provided herein.

In another aspect, provided herein is any one of antibodies or compositions provided herein, for use as a medicament.

In another aspect, provided herein is any one of antibodies or compositions provided herein, for use in the treatment of a methylated H1.0-related disease or condition; optionally wherein the disease or condition is selected from the group consisting of Alzheimer's disease, radiation exposure, exposure to a genotoxic stressor, a disease or condition comprising the accumulation of senescent cells, and a disease or condition accompanied by elevated levels of H1.0K180me2 proteins or peptides.

In another aspect, provided herein is any one of antibodies or compositions provided herein, for use in a method of treatment, wherein the method comprises clearing H1.0K180me2 in an individual; optionally wherein the individual suffers from a disease or condition selected from the group consisting of Alzheimer's disease, radiation exposure, exposure to a genotoxin, exposure to a DNA damaging agent, and a condition comprising the accumulation of senescent cells.

BRIEF DESCRIPTION OF THE DRAWINGS

FIG. 2A demonstrates binding efficiency of antibody clones to a H1.0Kme2 peptide (methylated at the residue corresponding to K180 of the human H1.0 protein). FIG. 2B demonstrates the binding efficiency of antibody clones to an unmodified H1.0 peptide (not methylated). FIG. 2C provides raw data for the binding of antibody clones to H1.0Kme2 or H1.0 peptide.

FIG. 3 shows specificity of antibody clones to H1.0 peptides with κ, 1, or 2 methyl modifications on K180.

FIG. 4A illustrates specific in vitro H1.0K180 methylation by G9A methyltransferase. FIG. 4B shows methylation sites on H1.0 by G9A determined by LC/MS.

FIG. 5A shows a protein sequence alignment between the antibody heavy chains of Clone A (SEQ ID NO: 6) and Clone B (SEQ ID NO: 7). FIG. 5B shows a protein sequence alignment between the antibody light chains of Clone A (SEQ ID NO: 8) and Clone B (SEQ ID NO: 9). FIG. 5C shows the DNA (SEQ ID NOs: 4 and 5) and protein sequences (SEQ ID NOs: 6 and 8) for antibody Clone A. FIG. 5D illustrates an exemplary method for recombinant expression of an antibody.

FIG. 7B depicts the sequence of antibody clone A light chain (SEQ ID NO: 8) and is annotated with structural information. FIG. 7C depicts the predicted light chain complementary determining regions (CDR) and framework (FW) regions for antibody Clone A (SEQ ID NOs: 10, 11, 14, 15, 18 and 38-43). FIG. 7D depicts the predicted heavy chain CDR and FW regions for antibody Clone A (SEQ ID NOs: 20-23, 28-31, 36, 37 and 44-56).

FIGS. 9A-9C show age-related accumulation of circulating H1.0K180me2 in the brain tissue and blood serum. Shown are western blot analyses of H1.0K180me2 in mouse (FIG. 9A) and human (FIG. 9B) brain tissue, revealing that its abundance increases with organismal age. FIG. 9C shows H1.0K180me2 levels in human serum samples normalized by total IgG serum levels. The symbol "a" represents an antibody, in this figure and throughout.

FIG. 10A shows that serum H1.0K180me2 is decreased in individuals with Alzheimer's disease, when compared to age-matched controls (normalized by serum volume). FIG. 10B shows that serum H1.0K180me2 is decreased in individuals with Alzheimer's disease, when compared to age-matched controls (normalized by total serum IgG levels). FIG. 10C shows that serum H1.0K180me2 is decreased in individuals with Alzheimer's disease, when compared to age-matched controls (normalized by total serum protein concentration).

FIG. 13A shows that exposure to ionizing radiation induces increased levels of circulating H1.0 K180me2 in mouse serum. FIG. 13A and FIG. 13B show a slot blot analysis of the presence (FIG. 13A) and quantification (FIG. 13B) of H1.0K180me2, using antibodies specific for the H1.0K180me2 epitope in the serum. FIG. 13C shows a western blot analysis of presence of H1.0K180me2 epitope levels, using antibodies specific for the H1.0K180me2 epitope, in mouse serum after X-ray irradiation (7 Gy).

DETAILED DESCRIPTION

Figure 1:
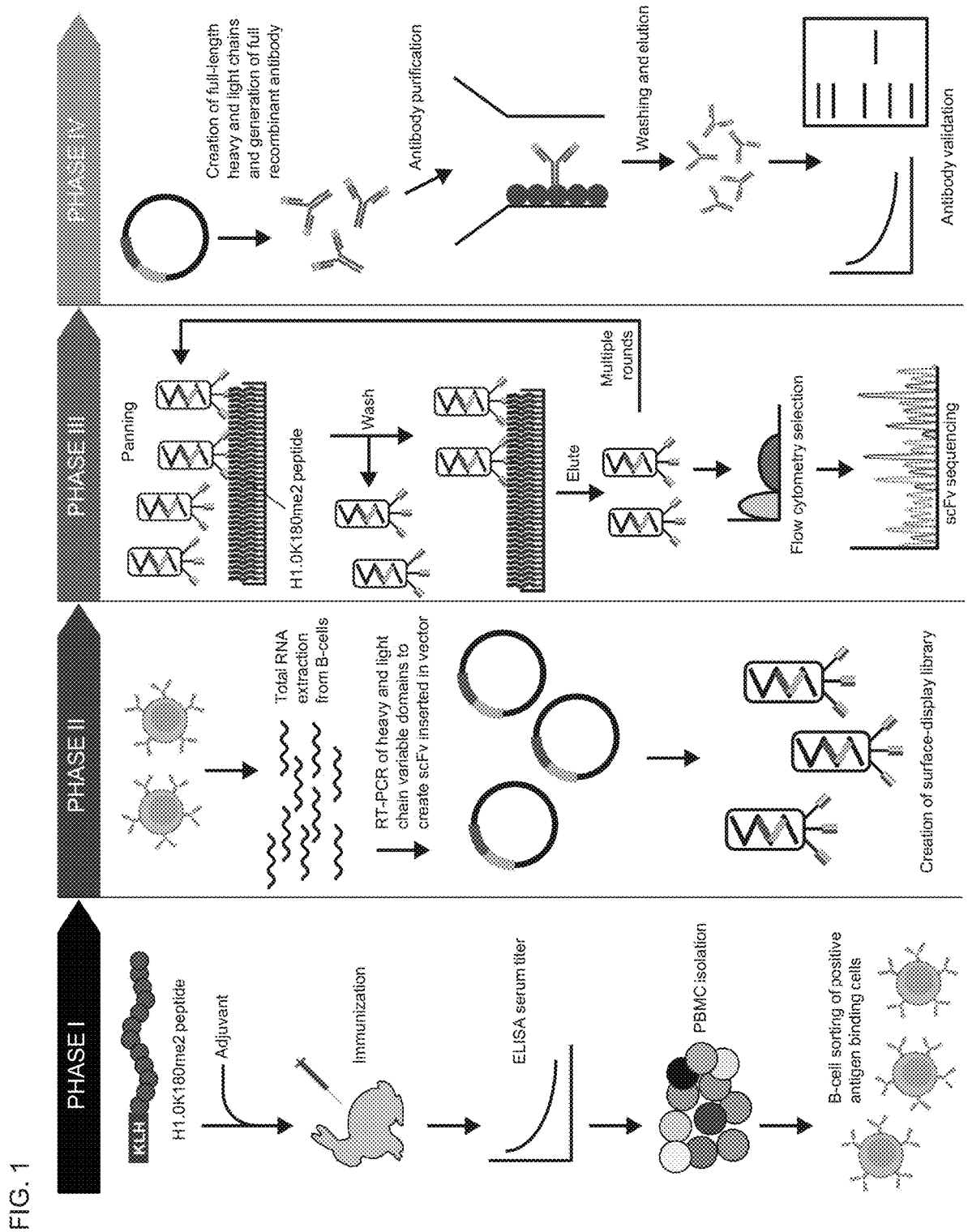
FIG. 1 diagrams an exemplary process of generating monoclonal antibodies.

Provided herein are H1.0K180me2 antibodies. These antibodies are useful for therapeutic and diagnostic uses. These H1.0K180me2 antibodies may be used in the treatment of methylated H1.0-related diseases or conditions in an individual. These H1.0K180me2 antibodies may also be used for detecting replicative senescence, DNA damage, genotoxic stress, radiation exposure, Alzheimer's disease, for monitoring therapeutic regimens, patient stratification, drug screening, and may serve as a marker of biological aging in a system. These compositions and methods are described in detail below.

WO 2017/184895 describes compositions and methods related to H1.0 dimethylated proteins; and WO 2017/184873 describes compositions and methods related to the methylation of H1.0 protein. The contents of these publications are incorporated herein by reference in their entirety.

I. H1.0Me2 Antibodies that Bind to Histone H1.0K180Me2 Proteins and Peptides

A. H1.0K180me2 Antibodies

Provided herein are antibodies that specifically bind a dimethylated histone H1.0 antigen, wherein the dimethylated histone H1.0 antigen is a histone H1.0 protein or peptide thereof, comprising a dimethylated lysine residue, wherein the lysine residue corresponds to K180 of the full length human histone H1.0 protein (SEQ ID NO: 1), and wherein the dimethylated K180 residue is required for binding. The K180 is represented by K* in SEQ ID NO: 1 of Table 1 below.

TABLE 1

SEQ ID NO: 1 Full length H1.0 Protein Amino
Acid Sequence
```
  1 MTENSTSAPA AKPKRAKASK KSTDHPKYSD MIVAAIQAEK
    NRAGSSRQSI QKYIKSHYKV
 61 GENADSQIKL SIKRLVTTGV LKQTKGVGAS GSFRLAKSDE
    PKKSVAFKKT KKEIKKVATP
121 KKASKPKKAA SKAPTKKPKA TPVKKAKKKL AATPKKAKKP
    KTVKAKPVKA SKPKKAKPVK*
181 PKAKSSAKRA GKKK (SEQ ID NO: 1)
```

SEQ ID NO: 2 Histone H1.0 Protein Amino Acid
Sequence with exemplary points of methylation
indicated
MTENSTSAPAAKPKRAKASKKSTDHPKYSDMIVAAIQAEKNRAGSSRQSI
QKYIKSHYKVGENADSQIKLSIKRLVTTGVLKQTKGVGASGSFRLAKSDE
PKKSVAFKKTKKEIKKVATPKKASKPKKAASKAPTKKPKATPVKKAKKKL
AATPK(me1/2/3)KAKKPKTVKPVK(me1/2/3)ASK(me1/2/3)PKK
(me1/2/3)AKPVK(me1/2/3)PKAKSSAKRAGKKK The dimethylated H1.0 antigen is interchangeably referred to as the H1.0K180me2 antigen or H1.0K180me2 epitope throughout. The H1.0K180me2-containing proteins and peptides are referred to as "H1.0K180me2 proteins" and "H1.0K180me2 peptides" throughout. The terms "anti-H1.0K180me2" or "H1.0K180me2 antibody" or "anti-H1.0K180me2 antibody" interchangeably refer to these antibodies.

As above, use of the term "K180" herein refers to the residue corresponding to K180 of the human H1.0 protein (SEQ ID NO: 1). Similarly, the term "K172", refers to the residue corresponding to K172 of the human H1.0 protein, the term "K190" refers to the residue corresponding to K190 of the human H1.0 protein, etc.

The H1.0K180me2 antibodies of the present disclosure bind to human and non-human mammalian H1.0K180me2 antigens.

The term "antibody" as used herein throughout is in the broadest sense and includes a monoclonal antibody, human antibody, humanized antibody, non-human antibody, chimeric antibody, bispecific antibody, an antigen-binding fragment (e.g. Fab fragment, a Fab'2 fragment, a CDR or a ScFv), and other antibody fragments that retain specificity for the H1.0K180me2 antigen. In some embodiments, the antibody is a single chain antibody that retains the specificity for the H1.0K180me2 antigen. In one exemplary embodiment, the antibodies are chimeric human×mouse antibodies. In one exemplary embodiment, the antibodies are chimeric human×rabbit antibodies. In one exemplary embodiment, the antibodies are humanized mouse antibodies. In one exemplary embodiment, the antibodies are humanized rabbit antibodies.

In some embodiments, the H1.0K180me2 antibodies provided herein are diagnostic antibodies. In some embodiments, the H1.0K180me2 antibodies provided herein are therapeutic antibodies.

In some embodiments, the H1.0K180me2 antibody is an affinity-purified antibody.

In some embodiments, the H1.0K180me2 antibody is an isolated antibody.

The H1.0K180me2 antibodies provided herein may be conjugated to an agent for a variety of purposes including, but not limited to, detection, diagnostics, visualization, quantification, sorting, therapeutics, and for use in biological assays.

In some embodiments, the H1.0K180me2 antibodies are conjugated to a label, for example a detectable label, a spin label, a colorimetric label, a radioactive label, an enzymatic label, a fluorescent label, or a magnetic label.

In some embodiments, the H1.0K180me2 antibodies are attached to a solid surface, for example a bead (e.g. a magnetic, glass or plastic bead), column, resin or a microplate. In some embodiments, an antibody is coated onto the microplate. In some embodiments, the antibodies attached to a solid surface are conjugated to a label; in some embodiments the antibodies attached to as solid surface are antigen-binding fragments.

In some embodiments, an antibody is conjugated to an effector molecule including, but not limited to, a radionuclide, a cytotoxin, a chemotherapeutic agent, a drug, a pro-drug, a toxin, an enzyme, an immunomodulator, a pro-apoptotic agent, a cytokine, a hormone, an oligonucleotide, an antisense molecule, a siRNA, and a second antibody.

The H1.0K180me2 antibodies provided herein can bind extracellular H1.0K180me2 and/or intracellular H1.0K180me2.

The antibodies provided herein may be of any immunoglobulin type such as IgG, IgA, IgE, IgD, or IgM. In some embodiments, the antibody is of the IgG subtype and may be an IgG1 antibody, an IgG2 antibody, an IgG3 antibody, or an IgG4 antibody.

Provided herein are antibodies specific for the H1.0K180me2 antigen from any species. In some embodiments, the H1.0K180me2 antibody is specific for human H1.0K180me2. In some embodiments, the H1.0K180me2 antibody is cross reactive with H1.0K180me2 from other species.

The H1.0K180me2 antibodies provided herein are selective for the H1.0K180me2 antigen, e.g. the H1.0K180me2 antibody is selective for dimethylation at residue K180.

The H1.0K180me2 antibodies provided herein are specific for the H1.0K180me2 antigen, e.g. the H1.0K180me2 antibody is specific for dimethylation at residue K180, and exhibits little or no binding of an H1.0K180 epitope (unmethylated at K180), H1.0K180me1 epitope (mono-methylated at K180), or an H1.0K180me3 epitope (trimethylated at K180). In some embodiments, the H1.0K180me2 antibody does not bind, or only minimally binds, an antigen that comprises an unmethylated K180 residue (FIG. 4D).

The antibodies provided herein specifically bind an H1.0K180me2-containing antigen. In some embodiments, the H1.0K180me2-containing antigen does not comprise any lysine residues that are methylated.

In some embodiments, the H1.0K180me2 antibody does not bind, or only minimally binds if the target H1.0K180me2 antigen comprises additional methylated lysine residues, e.g. where the lysine residues correspond to K166, K172, K174, K175, and/or K177 of a human histone H1.0 protein.

In some embodiments, the H1.0K180me2 antibody does not bind, or only minimally binds, an antigen that comprises one or more of the following residues: K172me1, K172me2, K172me3, K174me1, K174me2, K174me3, K175me1, K175me2, K175me3, K177me1, K177me2, K177me3, K166me1, K166me2, K166me3, K180me1, and/or K180me3.

In some embodiments, the H1.0K180me2 antibody does not bind, or only minimally binds, an antigen that comprises a dimethylated K180 residue, but also comprises one or more of the following residues: K172me1, K172me2, K172me3, K174me1, K174me2, K174me3, K175me1, K175me2, K175me3, K177me1, K177me2, K177me3, K166me1, K166me2, K166me3, K180me1, and/or K180me3.

In some embodiments, the H1.0K180me2 antibody does not bind, or only minimally binds, an antigen when the H1.0K180me2 antibody displays at least 1.5-fold, 2-fold, 2.5-fold, 2.7-fold, 5-fold, or even 10-fold less specificity (binding preference, affinity) for the antigen than for H1.0K180me2-containing antigen that does not comprise any other lysine residues that are methylated.

The H1.0K180me2 antibodies of the present disclosure may bind the H1.0K180me2 epitope in any medium.

In some embodiments, the H1.0K180me2 antibody displays at least 1.5-fold, 2-fold, 2.5-fold, 2.7-fold, 5-fold, or even 10-fold more specificity (binding preference, affinity) for the dimethylated antigen at K180 (H1.0K180me2 antigen), than an unmethylated antigen at K180 (H1.0K180 antigen). (FIG. 2A-2B) In some embodiments the specificity for an H1.0K180me2 antigen is generally at least about 2-fold, about 5-fold, or at least about 10-, 20-, 50-, 10^2-, 10^3-, 10^4, 10^5, or 10^6-fold over a non-specific target molecule (e.g. a randomly generated molecule lacking the specifically recognized site(s)), over an unmethylated K180 residue, over a trimethylated K180 residue, or over an H1.0 protein methylated at any other residue.

In some embodiments, the H1.0K180me2 antibody displays at least 1.5-fold, 2-fold, 2.5-fold, 2.7-fold, 5-fold, or even 10-fold more specificity (binding preference, affinity) for the dimethylated antigen at K180 (H1.0K180me2 antigen), than a monomethylated antigen at K180 (H1.0K180me1 antigen). (FIG. 3) In some embodiments the specificity for an H1.0K180me2 antigen is generally at least about 2-fold, about 5-fold, or at least about 10-, 20-, 50-, 10^2-, 10^3-, 10^4, 10^5, or 10^6-fold over a non-specific target molecule (e.g. a randomly generated molecule lacking the specifically recognized site(s)), over a monomethylated K180 residue, over a trimethylated K180 residue, or over an H1.0 protein methylated at any other residue.

In certain embodiments, the H1.0K180me2 antibodies provided herein has a dissociation constant (Kd) of range of 0.0001 nM to 1 μM. For example, Kd of the antibody may be about 1 μM, about 100 nM, about 50 nM, about 10 nM, about 5 nM, about 1 nM, about 0.5 nM, about 0.1 nM, about 0.05 nM, about 0.01 nM, about 0.005 nM, about 0.001 nM, about 0.0005 nM, or even about 0.0001 nM.

Figure 6:
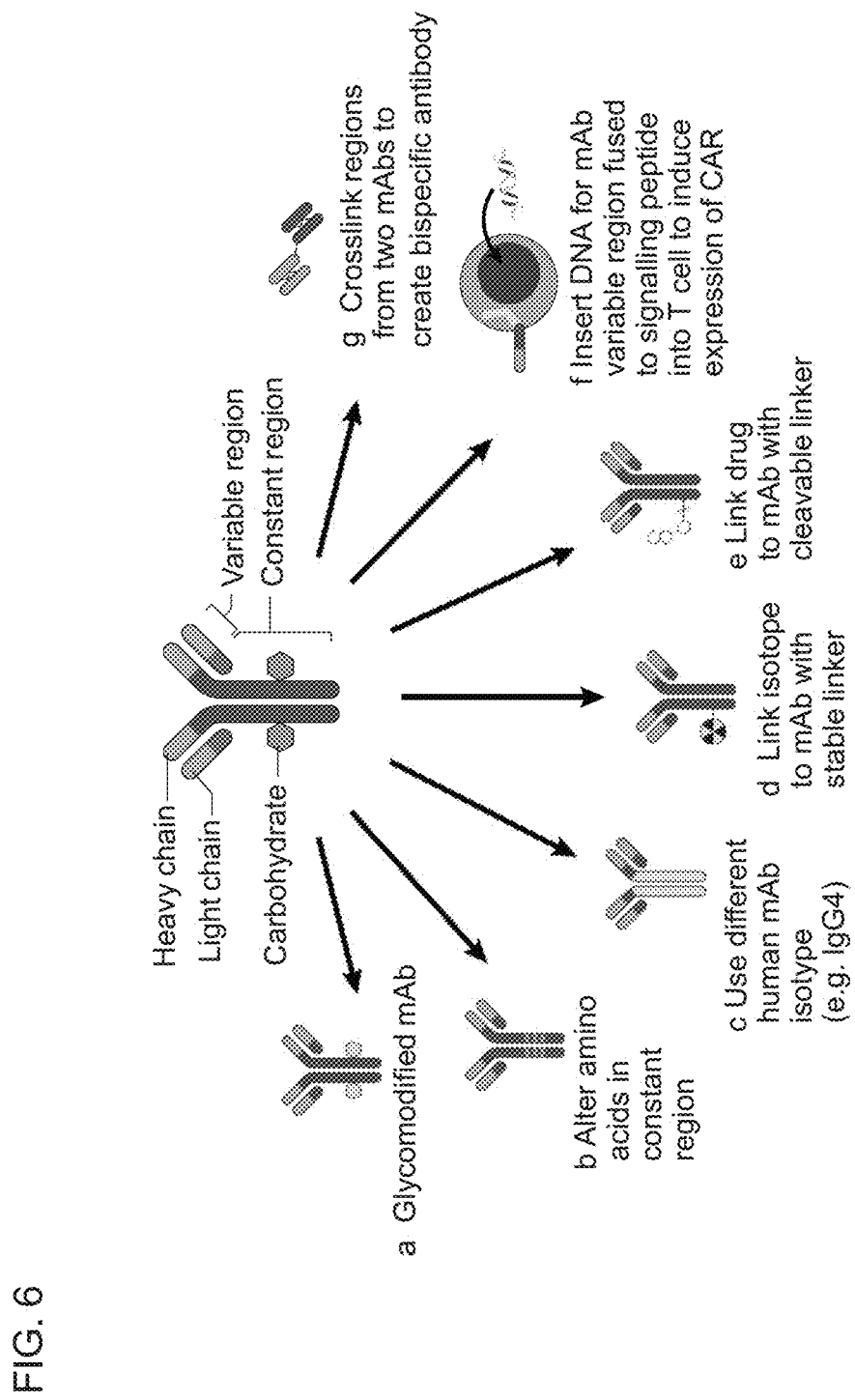
FIG. 6 illustrates various possible modifications to an antibody that can enhance function.

The structure of H1.0K180me2 antibodies (e.g. monoclonal H1.0K180me2 antibodies, mAb) may be modified to function in desired contexts, exemplary embodiments shown in FIG. 6.

FIG. 6, Part a. shows a glycomodified afucosylated mAb that exhibits enhanced binding to IgG Fc receptors (FcγR) as well as increased ADCC. Expression of mAbs in cell lines lacking fucosylation enzymes can be used to produce afucosylated mAbs. Any of the H1.0K180me2 antibodies described herein can be modified in this manner.

FIG. 6, Part b. The amino acid sequence of a mAb can be modified in the constant region. Such modification can increase binding of the mAb to FcγR and also increase ADCC. Any of the H1.0K180me2 antibodies described herein can be modified in this manner.

FIG. 6, Part c. When ADCC is not the desired mechanism, a different isotype can be substituted. IgG4 does not induce ADCC to the same degree that IgG1 does. Any of the H1.0K180me2 antibodies described herein can be modified in this manner.

FIG. 6, Part d. Radio-immunoconjugates can be produced by conjugating a radioactive isotope to a mAb linker. Use of a stable linker will prevent leakage of free radioactive isotope. Any of the H1.0K180me2 antibodies described herein can be modified in this manner.

FIG. 6, Part e. Antibody drug conjugates can be made by conjugating a drug to a mAb with a linker. A cleavable linker or pH-sensitive linker can be used to allow the drug to act separately from the mAb. Such conjugation can targeting of the drug to cell or tissue specified by the antibody and limits toxicity by not circulating freely. Any of the H1.0K180me2 antibodies described herein can be modified in this manner.

FIG. 6, Part f. The specificity of mAbs can utilized in the generation of Chimeric Antigen Receptor T cells (CAR-T cells). These can be generate by fusing the DNA that codes for a mAb variable region to the DNA sequence of the internal signaling portion of the T-cell receptor. This chimeric receptor is useful for introducing into T cells for use in adoptive therapy. The antigen binding domains of any the H1.0K180me2 antibodies described herein can be used to generated CAR-T cells.

FIG. 6, Part g. Bispecific antibodies are created by removing the constant region from an antibody and crosslinking the remaining variable region to the isolated variable region of another antibody. Removal of the constant region can result in reduced half-life and requires continuous transfusion of such a crosslinked antibody to achieve desired levels of exposure. Any of the H1.0K180me2 antibodies described herein can be modified in this manner.

In some embodiments the H1.0K180me2 antibody comprises the variable domain, complementary binding region, framework regions of Clone A (discussed below). In some embodiments, the H1.0K180me2 antibody is a monoclonal humanized antibody, or antigen-binding fragment thereof, that comprises the CDRs of Clone A (discussed below). In some embodiments the H1.0K180me2 antibody comprises the variable domain, complementary binding region, framework regions of Clone B (discussed below). In some embodiments, the H1.0K180me2 antibody is a monoclonal humanized antibody, or antigen-binding fragment thereof, that comprises the CDRs of Clone B (discussed below).

B. Generation of H1.0K180me2 Antibodies

A variety of immunoassay formats may be used to select antibodies specifically immunoreactive with H1.0K180me2. For example, solid-phase ELISA immunoassays may be used to select monoclonal antibodies specific to H1.0K180me2 (see, e.g., Harlow and Lane (1988) Antibodies, A Laboratory Manual, Cold Spring Harbor Publications, New York, for a description of immunoassay formats and conditions that may be used to determine specific immunoreactivity).

Production of the antibodies provided herein may be by any method known to those with skill in the art. For example, in some embodiments, the antibodies are produced by recombinant cells engineered to express the desired variable heavy (VH) and variable light (VL) and constant domains of the desired antibody (e.g. FIG. 5D). In some embodiments the antibodies are produced by hybridomas.

In some embodiments, any peptide comprising the H1.0K180me2 antigen, optionally linked to the immunogenic carrier, is used for immunization using standard protocols. In an exemplary embodiment, a peptide comprising CAKPVKASKPKKAKPVK(me2)PK (SEQ ID NO: 3), optionally linked to an immunogenic carrier, is used for immunization using standard protocols (FIG. 1). The quality and titer of generated antibodies may be assessed using techniques known to those in the art.

An exemplary method for developing a monoclonal antibody is illustrated in FIG. 1 as four distinct phases. As the figure describes, Phase I involves immunizing rabbits against a H1.0K180me2 peptide conjugated to a Keyhole Limpet Hemocyanin (KLH). The titer of the immunization is compared between pre-immunization and post-immunization bleeds. Peripheral Blood Mononuclear Cells (PBMCs) are isolated and were then sorted for positive antigen binding cells by flow cytometry. In Phase II, total RNA is extracted from cells isolated in Phase 1. RT-PCR of the heavy chain and light chain variable domains of the antibodies is performed and the scFv amplicon is inserted into vectors. These scFv vectors are then used to generate a cell surface-display library. In Phase III, the cell surface-display library is panned for at least one round with H1.0K180me2 peptide. This step further selects against unmethylated H1.0K peptide binding. Clones that bind H1.0K180me2 are further selected by flow cytometry and can be subsequently sequenced. In Phase IV, full length heavy chains and light chains are created to generate full recombinant antibodies. These antibodies can be expressed and purified. The binding of these antibodies to H1.0K180me2 protein can be then validated by ELISA, slot blot, and western blot. This is explained in further detail in Examples 2-4. Exemplary amino acid sequences for unmethylated as well as methylated H1.0 protein are provided in FIG. 4B as well as Table 1 above. (methylated lysine residues are denoted as (me1/2/3 indicating mono, di, and tri methylation possibilities).

The inventive compositions described herein also include nucleic acids encoding any of the antibodies disclosed herein, vectors comprising any of the nucleic acids encoding the antibodies, and host cells comprising any such vectors. Table 2 provides exemplary nucleic acid sequences for the antigen-binding fragments of the antibodies provided herein. Also provided herein are cells that contain the nucleotides and vectors encoding the antibodies. In some embodiments the antibodies are secreted.

TABLE 2

Exemplary H1.0K180me2 Antibody Nucleic Acid Sequences

SEQ ID NO: 4: Clone A heavy chain variable domain (VH)
cagtcggtggaggagtccgggggtcgcctggtcacgcctgggacacccct
gacactcacctgcacggtctctggattctccctcaataactatgtgatga
tgtgggtccgccaggctccaggggagggctggaatggatcgctgccatt
actactggcggtaccacatactacgcgaactgggcgaaaggccgattcac
catctccaaaacctcgaccacggtggatctgaaaatcatcagtccgacaa
ccgaggacacggccacctatttctgcgccagagatctttatggtgatact
agtgatgatatttgggatgcttttgatccctggggcccaggcaccctggt
caccgtctcctcag SEQ ID NO: 5: Clone A light chain variable domain (VL)
Gaccctgtgctgacccagactccatcgtccgtgtctgcagctgtgggagg
cacagtcaccatcagttgccagtccagtgagagtgtttataagaataaca
acttagcctggtatcagcagaaaccagggcagcctcccaagctcctgatc
tattctgcatccactctggcatctggggtcccatcgcggttcaaaggcag
tggatctgggacacagtcactctcaccatcagtggcgtgcagtgtgacga
tgctgccacttactactgtctaggagtatatagtgatattttgctttc Those of skill in the art understand that antibodies can also be prepared by any of a number of commercial services, e.g. upon provision of the sequences.

Tables 3-9 provides amino acid sequences for the antigen-binding fragments of some exemplary H1.0K180me2 antibodies.

Table 3 provides exemplary heavy chain variable (VH) and heavy chain light (VL) sequences. Also provided herein are VH and VL sequences that have at least 85%

TABLE 3

Exemplary H1.0K180me2 antibody VH and VL sequences

SEQ ID NO: 6: Amino Acid Sequence of the Heavy Chain Variable (VH) Domain of an H1.0K180me2 antibody (Clone A)
QSVEESGGRLVTPGTPLTLTCTVSGFSLNNYVMMWVRQAPGEGLEWIAAI
TTGGTTYYANWAKGRFTISKTSTTVDLKIISPTTEDTATYFCARDLYGDT
SDDIWDAFDPWGPGTLVTVSS SEQ ID NO: 7: Amino Acid Sequence of the Heavy Chain Variable Domain of an H1.0K180me2 antibody (Clone B)
QSLEESGGRLVTPGTPLTLTCTASGFSLSDYYTTWVRQAPGQGLEYIGYI
SGTGTPYYATWAKGRFTISRTSTTVGLKMTSLTTEDTATYFCARSYPGID
ANN SEQ ID NO: 8: Amino Acid Sequence of the Light Chain Variable (VL) Domain of an H1.0K180me2 antibody (Clone A)
DPVLTQTPSSVSAAVGGTVTISCQSSESVYKNNNLAWYQQKPGQPPKLLI
YSASTLASGVPSRFKGSGSGTQFTLTISGVQCDDAATYYCLGVYSDIFAF SEQ ID NO: 9: Amino Acid Sequence of the Light Chain Variable Domain of an H1.0K180me2 antibody (Clone B)
AQVLTQTPSSVSAAVGGTVTISCQSSQSVYNNNYLGWYQQKPGQPPKLLI
YLASTLASGVPSRFKGSGSGTQFTLTISDLECDDAATYYCGGDYDVYIAA
F Tables 4-9 provide exemplary complementary determining region (CDR) sequences (regions 1, 2, and 3) of the antigen-binding domain of the light chain (CDR-L) and the antigen-binding domain of the heavy chain (CDR-H). As referred to below, a VL CDR1 region is referred to as CDR-L1; a VL CDR2 region is referred to as CDR-L2; a VL CDR3 region is referred to as CDR-L3; a VH CDR1 region is referred to as CDR-H1; a VH CDR2 region is referred to as CDR-H2; and a VH CDR3 region is referred to as CDR-H3.

TABLE 4

Exemplary H1.0K180me2 antibody CDR-L1 sequences

SEQ ID NO: 10: Amino Acid Sequence of CDR-L1
QSSESVYKNNNLA

SEQ ID NO: 11: Amino Acid Sequence of CDR-L1
YKNNNLAWY

SEQ ID NO: 12: Amino Acid Sequence of CDR-L1
QSSQSVYNNNYLG

SEQ ID NO: 13: Amino Acid Sequence of CDR-L1
YNNNYLGWY

TABLE 5

Exemplary H1.0K180me2 antibody CDR-L2 sequences

SEQ ID NO: 14: Amino Acid Sequence of CDR-L2
SASTLAS

SEQ ID NO: 15: Amino Acid Sequence of CDR-L2
LLIYSASTLA

SEQ ID NO: 16: Amino Acid Sequence of CDR-L2
LASTLAS

TABLE 5-continued

Exemplary H1.0K180me2 antibody CDR-L2 sequences

SEQ ID NO: 17: Amino Acid Sequence of CDR-L2
LLIYLASTLA

Table 6

Exemplary H1.0K180me2 antibody CDR-L3 sequences

SEQ ID NO: 18: Amino Acid Sequence of CDR-L3
LGVYSDIFAF

SEQ ID NO: 19: Amino Acid Sequence of CDR-L3
GGDYDVYIAA

TABLE 7

Exemplary H1.0K180me2 antibody CDR-H1 sequences

SEQ ID NO: 20: Amino Acid Sequence of CDR-H1
GFSLNNY

SEQ ID NO: 21: Amino Acid Sequence of CDR-H1
GFSLNNYVMM

SEQ ID NO: 22: Amino Acid Sequence of CDR-H1
NYVMM

SEQ ID NO: 23: Amino Acid Sequence of CDR-H1
NNYVMM

SEQ ID NO: 24: Amino Acid Sequence of CDR-H1
GFSLSDY

SEQ ID NO: 25: Amino Acid Sequence of CDR-H1
GFSLSDYYTT

SEQ ID NO: 26: Amino Acid Sequence of CDR-H1
DYYTT

SEQ ID NO: 27: Amino Acid Sequence of CDR-H1
SDYYTT

TABLE 8

Exemplary H1.0K180me2 antibody CDR-H2 sequences

SEQ ID NO: 28: Amino Acid Sequence of CDR-H2
TTGGT

SEQ ID NO: 29: Amino Acid Sequence of CDR-H2
AITTGGTTY

SEQ ID NO: 30: Amino Acid Sequence of CDR-H2
AITTGGTTYYANWAKG

SEQ ID NO: 31: Amino Acid Sequence of CDR-H2
WIAAITTGGTTY

SEQ ID NO: 32: Amino Acid Sequence of CDR-H2
SGTGT

SEQ ID NO: 33: Amino Acid Sequence of CDR-H2
YISGTGTPY

SEQ ID NO: 34: Amino Acid Sequence of CDR-H2
YISGTGTPYYATWAKG

TABLE 8-continued

Exemplary H1.0K180me2 antibody CDR-H2 sequences

SEQ ID NO: 35: Amino Acid Sequence of CDR-H2
YIGYISGTGTPY

TABLE 9

Exemplary H1.0K180me2 antibody CDR-H3 sequences

SEQ ID NO: 36: Amino Acid Sequence of CDR-H3
DLYGDTSDDIWDAFDP

SEQ ID NO: 37: Amino Acid Sequence of CDR-H3
ARDLYGDTSDDIWDAFD

In some embodiments, provided herein is an H1.0K180me2 antibody, wherein the antibody comprises the heavy chain variable domain of SEQ ID NO: 6 or SEQ ID NO: 7.

In some embodiments, provided herein is an H1.0K180me2 antibody, wherein the antibody comprises the light chain variable domain of SEQ ID NO: 8 or SEQ ID NO: 9.

In some embodiments, provided herein is an H1.0K180me2 antibody, wherein the antibody comprises the heavy chain variable domain of SEQ ID NO: 6 or SEQ ID NO: 7 and the light chain variable domain of SEQ ID NO: 8 or SEQ ID NO: 9.

In some embodiments, provided herein is an H1.0K180me2 antibody, wherein the antibody comprises the heavy chain variable domain of SEQ ID NO: 6 and comprises the light chain variable domain of SEQ ID NO: 8.

In some embodiments, provided herein is a H1.0K180me2, wherein the antibody comprises the heavy chain variable domain of SEQ ID NO: 6 and comprises the light chain variable domain of SEQ ID NO: 9.

In some embodiments, provided herein is an H1.0K180me2 antibody, wherein the antibody comprises the heavy chain variable domain of SEQ ID NO: 7 and comprises the light chain variable domain of SEQ ID NO: 8.

In some embodiments, provided herein is an H1.0K180me2 antibody, wherein the antibody comprises the heavy chain variable domain of SEQ ID NO: 7 and comprises the light chain variable domain of SEQ ID NO: 9.

In some embodiments, provided herein is an H1.0K180me2 antibody, wherein the antigen-binding region of the antibody comprises:
  (a) any one of the CDR-L1 amino acid sequences of Table 4;
  (b) any one of the CDR-L2 amino acid sequences of Table 5; and
  (c) any one of the CDR-L3 amino acid sequences of Table 6.

In some embodiments, provided herein is an H1.0K180me2 antibody, wherein the antigen-binding region of the antibody comprises:
  (a) any one of the CDR-H1 amino acid sequences of Table 7;
  (b) any one of the CDR-H2 amino acid sequences of Table 8; and
  (c) any one of the CDR-H3 amino acid sequences of Table 9.

In some embodiments, provided herein is an H1.0K180me2 antibody, wherein the antigen-binding region of the antibody comprises: an H1.0K180me2 antigen or a peptide thereof, wherein the antigen-binding domain of the antibody comprises any one of the CDR-L amino acid sequences of Tables 4, 5, and 6, and comprises any one of the CDR-H amino acid sequences of Tables 7, 8, and 9.

In some embodiments, provided herein is an H1.0K180me2 antibody, wherein the light chain of the antibody comprises the CDR-L1 of SEQ ID NO: 10, SEQ ID NO: 11, SEQ ID NO.12, or SEQ ID NO: 13.

In some embodiments, provided herein is an H1.0K180me2 antibody, wherein the light chain of the antibody comprises the CDR-L2 of SEQ ID NO: 14, SEQ ID NO: 15, SEQ ID NO.16, or SEQ ID NO: 17.

In some embodiments, provided herein is an H1.0K180me2 antibody, wherein the light chain of the antibody comprises the CDR-L3 of SEQ ID NO: 18 or SEQ ID NO: 19.

In some embodiments, provided herein is an H1.0K180me2 antibody, wherein the light chain of the antibody comprises the CDR-L1 of SEQ ID NO: 10, SEQ ID NO: 11, SEQ ID NO.12, or SEQ ID NO: 13; a CDR-L2 of SEQ ID NO: 14, SEQ ID NO: 15, SEQ ID NO.16, or SEQ ID NO: 17; and a CDR-L3 of SEQ ID NO: 18 or SEQ ID NO: 19.

In some embodiments, provided herein is an H1.0K180me2 antibody, wherein the light chain of the antibody comprises the CDR-L1 of SEQ ID NO: 10 or SEQ ID NO: 11, the CDR-L2 of SEQ ID NO: 14 or SEQ ID NO: 15, or the CDR-L3 of SEQ ID NO: 18.

In some embodiments, provided herein is an H1.0K180me2 antibody, wherein the light chain of the antibody comprises the CDR-L1 of SEQ ID NO: 12 or SEQ ID NO: 13, the CDR-L2 of SEQ ID NO: 16 or SEQ ID NO: 17, or the CDR-L3 of SEQ ID NO: 19.

In some embodiments, provided herein is an H1.0K180me2 antibody, wherein the heavy chain of the antibody comprises the CDR-H1 of SEQ ID NO: 20, SEQ ID NO: 21, SEQ ID NO: 22, or SEQ ID NO: 23; the CDR-H2 of SEQ ID NO: 28, SEQ ID NO: 29, SEQ ID NO: 30, or SEQ ID NO: 31; or the CDR-H3 of SEQ ID NO: 36 or SEQ ID NO: 37.

In some embodiments, provided herein is an H1.0K180me2 antibody, wherein the light chain of the antibody comprises the CDR-L1 of SEQ ID NO: 10, CDR-L2 of SEQ ID NO: 14, and CDR-L3 of SEQ ID NO: 18.

In some embodiments, provided herein is an H1.0K180me2 antibody, wherein the light chain of the antibody comprises the CDR-L1 of SEQ ID NO: 10, CDR-L2 of SEQ ID NO: 15, and CDR-L3 of SEQ ID NO: 18.

In some embodiments, provided herein is an H1.0K180me2 antibody, wherein the light chain of the antibody comprises the CDR-L1 of SEQ ID NO: 11, CDR-L2 of SEQ ID NO: 14, and CDR-L3 of SEQ ID NO: 18.

In some embodiments, provided herein is an H1.0K180me2 antibody, wherein the light chain of the antibody comprises the CDR-L1 of SEQ ID NO: 11, CDR-L2 of SEQ ID NO: 15, and CDR-L3 of SEQ ID NO: 18.

In some embodiments, provided herein is an H1.0K180me2 antibody, wherein the light chain of the antibody comprises the CDR-L1 of SEQ ID NO: 12, CDR-L2 of SEQ ID NO: 14, and CDR-L3 of SEQ ID NO: 18.

In some embodiments, provided herein is an H1.0K180me2 antibody, wherein the light chain of the antibody comprises the CDR-L1 of SEQ ID NO: 12, CDR-L2 of SEQ ID NO: 16, and CDR-L3 of SEQ ID NO: 18.

In some embodiments, provided herein is an H1.0K180me2 antibody, wherein the light chain of the antibody comprises the CDR-L1 of SEQ ID NO: 12, CDR-L2 of SEQ ID NO: 17, and CDR-L3 of SEQ ID NO: 18.

In some embodiments, provided herein is an H1.0K180me2 antibody, wherein the light chain of the antibody comprises the CDR-L1 of SEQ ID NO: 13, CDR-L2 of SEQ ID NO: 16, and CDR-L3 of SEQ ID NO: 18.

In some embodiments, provided herein is an H1.0K180me2 antibody, wherein the light chain of the antibody comprises the CDR-L1 of SEQ ID NO: 13, CDR-L2 of SEQ ID NO: 17, and CDR-L3 of SEQ ID NO: 18.

In some embodiments, provided herein is an H1.0K180me2 antibody, wherein the heavy chain of the antibody comprises the CDR-H1 of SEQ ID NO: 20, SEQ ID NO: 21, SEQ ID NO: 22, SEQ ID NO: 23 SEQ ID NO: 24, SEQ ID NO: 25, SEQ ID NO: 26, or SEQ ID NO: 27.

In some embodiments, provided herein is an H1.0K180me2 antibody, wherein the heavy chain of the antibody comprises the CDR-H2 of SEQ ID NO: 28, SEQ ID NO: 29, SEQ ID NO: 30, SEQ ID NO: 31 SEQ ID NO: 32, SEQ ID NO: 33, SEQ ID NO: 34, or SEQ ID NO: 35.

In some embodiments, provided herein is an H1.0K180me2 antibody, wherein the heavy chain of the antibody comprises the CDR-H3 of SEQ ID NO: 36 or SEQ ID NO: 37.

In some embodiments, provided herein is an H1.0K180me2 antibody, wherein the heavy chain of antibody comprises the CDR-H1 of SEQ ID NO: 20, SEQ ID NO: 21, SEQ ID NO: 22, SEQ ID NO: 23 SEQ ID NO: 24, SEQ ID NO: 25, SEQ ID NO: 26, or SEQ ID NO: 27; comprises the CDR-H2 of SEQ ID NO: 28, SEQ ID NO: 29, SEQ ID NO: 30, SEQ ID NO: 31 SEQ ID NO: 32, SEQ ID NO: 33, SEQ ID NO: 34, or SEQ ID NO: 35; and comprises the CDR-H3 of SEQ ID NO: 36 or SEQ ID NO: 37.

In some embodiments, provided herein is an H1.0K180me2 antibody, wherein the heavy chain of the antibody comprises the CDR-H1 of SEQ ID NO: 20 and comprises the CDR-H2 of SEQ ID NO: 28 and comprises the CDR-H3 of SEQ ID NO: 36.

In some embodiments, provided herein is an H1.0K180me2 antibody, wherein the heavy chain of the antibody comprises the CDR-H1 of SEQ ID NO: 20 comprises the CDR-H2 of SEQ ID NO: 29 and comprises the CDR-H3 of SEQ ID NO: 36.

In some embodiments, provided herein is an H1.0K180me2 antibody, wherein the heavy chain of the antibody comprises the CDR-H1 of SEQ ID NO: 20, and comprises the CDR-H2 of SEQ ID NO: 30 and comprises the CDR-H3 of SEQ ID NO: 36.

In some embodiments, provided herein is an H1.0K180me2 antibody, wherein the heavy chain of the antibody comprises the CDR-H1 of SEQ ID NO: 20 and comprises the CDR-H2 of SEQ ID NO: 31 and comprises the CDR-H3 of SEQ ID NO: 36.

In some embodiments, provided herein is an H1.0K180me2 antibody, wherein the heavy chain of the antibody comprises the CDR-H1 of SEQ ID NO: 21 and comprises the CDR-H2 of SEQ ID NO: 28 and comprises the CDR-H3 of SEQ ID NO: 36.

In some embodiments, provided herein is an H1.0K180me2 antibody, wherein the heavy chain of the antibody comprises the CDR-H1 of SEQ ID NO: 21 comprises the CDR-H2 of SEQ ID NO: 29 and comprises the CDR-H3 of SEQ ID NO: 36.

In some embodiments, provided herein is an H1.0K180me2 antibody, wherein the heavy chain of the antibody comprises the CDR-H1 of SEQ ID NO: 21, and comprises the CDR-H2 of SEQ ID NO: 30 and comprises the CDR-H3 of SEQ ID NO: 36.

In some embodiments, provided herein is an H1.0K180me2 antibody, wherein the heavy chain of the antibody comprises the CDR-H1 of SEQ ID NO: 21 and comprises the CDR-H2 of SEQ ID NO: 31 and comprises the CDR-H3 of SEQ ID NO: 36.

In some embodiments, provided herein is an H1.0K180me2 antibody, wherein the heavy chain of the antibody comprises the CDR-H1 of SEQ ID NO: 22 and comprises the CDR-H2 of SEQ ID NO: 28 and comprises the CDR-H3 of SEQ ID NO: 36.

In some embodiments, provided herein is an H1.0K180me2 antibody, wherein the heavy chain of the antibody comprises the CDR-H1 of SEQ ID NO: 22 comprises the CDR-H2 of SEQ ID NO: 29 and comprises the CDR-H3 of SEQ ID NO: 36.

In some embodiments, provided herein is an H1.0K180me2 antibody, wherein the heavy chain of the antibody comprises the CDR-H1 of SEQ ID NO: 22 and comprises the CDR-H2 of SEQ ID NO: 30 and comprises the CDR-H3 of SEQ ID NO: 36.

In some embodiments, provided herein is an H1.0K180me2 antibody, wherein the heavy chain of the antibody comprises the CDR-H1 of SEQ ID NO: 22 and comprises the CDR-H2 of SEQ ID NO: 31 and comprises the CDR-H3 of SEQ ID NO: 36.

In some embodiments, provided herein is an H1.0K180me2 antibody, wherein the heavy chain of the antibody comprises the CDR-H1 of SEQ ID NO: 23 and comprises the CDR-H2 of SEQ ID NO: 28 and comprises the CDR-H3 of SEQ ID NO: 36.

In some embodiments, provided herein is an H1.0K180me2 antibody, wherein the heavy chain of the antibody comprises the CDR-H1 of SEQ ID NO: 23 comprises the CDR-H2 of SEQ ID NO: 29 and comprises the CDR-H3 of SEQ ID NO: 36.

In some embodiments, provided herein is an H1.0K180me2 antibody, wherein the heavy chain of the antibody comprises the CDR-H1 of SEQ ID NO: 23 and comprises the CDR-H2 of SEQ ID NO: 30 and comprises the CDR-H3 of SEQ ID NO: 36.

In some embodiments, provided herein is an H1.0K180me2 antibody, wherein the heavy chain of the antibody comprises the CDR-H1 of SEQ ID NO: 23 and comprises the CDR-H2 of SEQ ID NO: 31 and comprises the CDR-H3 of SEQ ID NO: 36.

In some embodiments, provided herein is an H1.0K180me2 antibody, wherein the heavy chain of the antibody comprises the CDR-H1 of SEQ ID NO: 20 and comprises the CDR-H2 of SEQ ID NO: 28 and comprises the CDR-H3 of SEQ ID NO: 37.

In some embodiments, provided herein is an H1.0K180me2 antibody, wherein the heavy chain of the antibody comprises the CDR-H1 of SEQ ID NO: 20 comprises the CDR-H2 of SEQ ID NO: 29 and comprises the CDR-H3 of SEQ ID NO: 37.

In some embodiments, provided herein is an H1.0K180me2 antibody, wherein the heavy chain of the antibody comprises the CDR-H1 of SEQ ID NO: 20, and comprises the CDR-H2 of SEQ ID NO: 30 and comprises the CDR-H3 of SEQ ID NO: 37.

In some embodiments, provided herein is an H1.0K180me2 antibody, wherein the heavy chain of the antibody comprises the CDR-H1 of SEQ ID NO: 20 and comprises the CDR-H2 of SEQ ID NO: 31 and comprises the CDR-H3 of SEQ ID NO: 37.

In some embodiments, provided herein is an H1.0K180me2 antibody, wherein the heavy chain of the antibody comprises the CDR-H1 of SEQ ID NO: 21 and comprises the CDR-H2 of SEQ ID NO: 28 and comprises the CDR-H3 of SEQ ID NO: 37.

In some embodiments, provided herein is an H1.0K180me2 antibody, wherein the heavy chain of the antibody comprises the CDR-H1 of SEQ ID NO: 21 comprises the CDR-H2 of SEQ ID NO: 29 and comprises the CDR-H3 of SEQ ID NO: 37.

In some embodiments, provided herein is an H1.0K180me2 antibody, wherein the heavy chain of the antibody comprises the CDR-H1 of SEQ ID NO: 21, and comprises the CDR-H2 of SEQ ID NO: 30 and comprises the CDR-H3 of SEQ ID NO: 37.

In some embodiments, provided herein is an H1.0K180me2 antibody, wherein the heavy chain of the antibody comprises the CDR-H1 of SEQ ID NO: 21 and comprises the CDR-H2 of SEQ ID NO: 31 and comprises the CDR-H3 of SEQ ID NO: 37.

In some embodiments, provided herein is an H1.0K180me2 antibody, wherein the heavy chain of the antibody comprises the CDR-H1 of SEQ ID NO: 22 and comprises the CDR-H2 of SEQ ID NO: 28 and comprises the CDR-H3 of SEQ ID NO: 37.

In some embodiments, provided herein is an H1.0K180me2 antibody, wherein the heavy chain of the antibody comprises the CDR-H1 of SEQ ID NO: 22 comprises the CDR-H2 of SEQ ID NO: 29 and comprises the CDR-H3 of SEQ ID NO: 37.

In some embodiments, provided herein is an H1.0K180me2 antibody, wherein the heavy chain of the antibody comprises the CDR-H1 of SEQ ID NO: 22 and comprises the CDR-H2 of SEQ ID NO: 30 and comprises the CDR-H3 of SEQ ID NO: 37.

In some embodiments, provided herein is an H1.0K180me2 antibody, wherein the heavy chain of the antibody comprises the CDR-H1 of SEQ ID NO: 22 and comprises the CDR-H2 of SEQ ID NO: 31 and comprises the CDR-H3 of SEQ ID NO: 37.

In some embodiments, provided herein is an H1.0K180me2 antibody, wherein the heavy chain of the antibody comprises the CDR-H1 of SEQ ID NO: 23 and comprises the CDR-H2 of SEQ ID NO: 28 and comprises the CDR-H3 of SEQ ID NO: 37.

In some embodiments, provided herein is an H1.0K180me2 antibody, wherein the heavy chain of the antibody comprises the CDR-H1 of SEQ ID NO: 23 comprises the CDR-H2 of SEQ ID NO: 29 and comprises the CDR-H3 of SEQ ID NO: 37.

In some embodiments, provided herein is an H1.0K180me2 antibody, wherein the heavy chain of the antibody comprises the CDR-H1 of SEQ ID NO: 23 and comprises the CDR-H2 of SEQ ID NO: 30 and comprises the CDR-H3 of SEQ ID NO: 37.

In some embodiments, provided herein is an H1.0K180me2 antibody, wherein the heavy chain of the antibody comprises the CDR-H1 of SEQ ID NO: 23 and comprises the CDR-H2 of SEQ ID NO: 31 and comprises the CDR-H3 of SEQ ID NO: 37.

In some embodiments, provided herein is an H1.0K180me2 antibody, wherein the heavy chain of the antibody comprises the CDR-H1 of SEQ ID NO: 24 and comprises the CDR-H2 of SEQ ID NO: 32.

In some embodiments, provided herein is an H1.0K180me2 antibody, wherein the heavy chain of the antibody comprises the CDR-H1 of SEQ ID NO: 24 and comprises the CDR-H2 of SEQ ID NO: 33.

In some embodiments, provided herein is an H1.0K180me2 antibody, wherein the heavy chain of the antibody comprises the CDR-H1 of SEQ ID NO: 24 and comprises the CDR-H2 of SEQ ID NO: 34.

In some embodiments, provided herein is an H1.0K180me2 antibody, wherein the heavy chain of the antibody comprises the CDR-H1 of SEQ ID NO: 24 and comprises the CDR-H2 of SEQ ID NO: 35.

In some embodiments, provided herein is an H1.0K180me2 antibody, wherein the heavy chain of the antibody comprises the CDR-H1 of SEQ ID NO: 25 and comprises the CDR-H2 of SEQ ID NO: 32.

In some embodiments, provided herein is an H1.0K180me2 antibody, wherein the heavy chain of the antibody comprises the CDR-H1 of SEQ ID NO: 25 and comprises the CDR-H2 of SEQ ID NO: 33.

In some embodiments, provided herein is an H1.0K180me2 antibody, wherein the heavy chain of the antibody comprises the CDR-H1 of SEQ ID NO: 25 and comprises the CDR-H2 of SEQ ID NO: 34.

In some embodiments, provided herein is an H1.0K180me2 antibody, wherein the heavy chain of the antibody comprises the CDR-H1 of SEQ ID NO: 25 comprises the CDR-H2 of SEQ ID NO: 35.

In some embodiments, provided herein is an H1.0K180me2 antibody, wherein the heavy chain of the antibody comprises the CDR-H1 of SEQ ID NO: 26 and comprises the CDR-H2 of SEQ ID NO: 32.

In some embodiments, provided herein is an H1.0K180me2 antibody, wherein the heavy chain of the antibody comprises the CDR-H1 of SEQ ID NO: 26 and comprises the CDR-H2 of SEQ ID NO: 33.

In some embodiments, provided herein is an H1.0K180me2 antibody, wherein the heavy chain of the antibody comprises the CDR-H1 of SEQ ID NO: 26 and comprises the CDR-H2 of SEQ ID NO: 34.

In some embodiments, provided herein is an H1.0K180me2 antibody, wherein the heavy chain of the antibody comprises the CDR-H1 of SEQ ID NO: 26 comprises the CDR-H2 of SEQ ID NO: 35.

In some embodiments, provided herein is an H1.0K180me2 antibody, wherein the heavy chain of the antibody comprises the CDR-H1 of SEQ ID NO: 27 and comprises the CDR-H2 of SEQ ID NO: 32.

In some embodiments, provided herein is an H1.0K180me2 antibody, wherein the heavy chain of the antibody comprises the CDR-H1 of SEQ ID NO: 27 and comprises the CDR-H2 of SEQ ID NO: 33.

In some embodiments, provided herein is an H1.0K180me2 antibody, wherein the heavy chain of the antibody comprises the CDR-H1 of SEQ ID NO: 27 and comprises the CDR-H2 of SEQ ID NO: 34.

In some embodiments, provided herein is an H1.0K180me2 antibody, wherein the heavy chain of the antibody comprises the CDR-H1 of SEQ ID NO: 27 comprises the CDR-H2 of SEQ ID NO: 35.

Table 10 provides exemplary antibody framework (FW) sequences. As referred to below, VL framework regions are referred to as LRF1, LRF2, and LRF3. Likewise, VH framework regions are referred to as HRF1, HRF2, HRF3, and HRF4.

TABLE 10

Exemplary H1.0K180me2 antibody framework (FW) sequences

Clone A Sequences

SEQ ID NO: 38: Amino Acid Sequence of LRF1
DPVLTQTPSSVSAAVGGTVTISC

SEQ ID NO: 39: Amino Acid Sequence of LRF1
DPVLTQTPSSVSAAVGGTVTISCQSSESV

SEQ ID NO: 40: Amino Acid Sequence of LRF2
WYQQKPGQPPKLLIY

SEQ ID NO: 41: Amino Acid Sequence of LRF2
QQKPGQPPK

SEQ ID NO: 42: Amino Acid Sequence of LRF3
GVPSRFKGSGSGTQFTLTISGVQCDDAATYYC

SEQ ID NO: 43: Amino Acid Sequence of LRF3
SGVPSRFKGSGSGTQFTLTISGVQCDDAATYYC

SEQ ID NO: 44: Amino Acid Sequence of HFR1
QSVEESGGRLVTPGTPLTLTCTVS

SEQ ID NO: 45: Amino Acid Sequence of HFR1
QSVEESGGRLVTPGTPLTLTCTVSGFSLN

SEQ ID NO: 46: Amino Acid Sequence of HFR1
QSVEESGGRLVTPGTPLTLTCTVSGFSL

SEQ ID NO: 47: Amino Acid Sequence of HFR2
VMMWVRQAPGEGLEWIAAI

SEQ ID NO: 48: Amino Acid Sequence of HFR2
WVRQAPGEGLEWIA

SEQ ID NO: 49: Amino Acid Sequence of HFR2
WVRQAPGEGLE

SEQ ID NO: 50: Amino Acid Sequence of HFR3
TYYANWAKGRFTISKTSTTVDLKIISPTTEDTATYFCAR SEQ ID NO: 51: Amino Acid Sequence of HFR3
YANWAKGRFTISKTSTTVDLKIISPTTEDTATYFCAR SEQ ID NO: 52: Amino Acid Sequence of HFR3
RFTISKTSTTVDLKIISPTTEDTATYFCAR SEQ ID NO: 53: Amino Acid Sequence of HFR3
YANWAKGRFTISKTSTTVDLKIISPTTEDTATYFC SEQ ID NO: 54: Amino Acid Sequence of HFR4
WGPGTLVTVSS SEQ ID NO: 55: Amino Acid Sequence of HFR4
PWGPGTLVTVSS Clone B Sequences SEQ ID NO: 56: Amino Acid Sequence of LRF1
AQVLTQTPSSVSAAVGGTVTISC SEQ ID NO: 57: Amino Acid Sequence of LRF1
AQVLTQTPSSVSAAVGGTVTISCQSSQSV SEQ ID NO: 58: Amino Acid Sequence of LRF2
WYQQKPGQPPKLLIY SEQ ID NO: 59: Amino Acid Sequence of LRF2
QQKPGQPPK SEQ ID NO: 60: Amino Acid Sequence of LRF3
GVPSRFKGSGSGTQFTLTISDLECDDAATYYC SEQ ID NO: 61: Amino Acid Sequence of LRF3
SGVPSRFKGSGSGTQFTLTISDLECDDAATYYC TABLE 10-continued Exemplary H1.0K180me2 antibody
framework (FW) sequences SEQ ID NO: 62: Amino Acid Sequence of HFR1
QSLEESGGRLVTPGTPLTLTCTAS SEQ ID NO: 63: Amino Acid Sequence of HFR1
QSLEESGGRLVTPGTPLTLTCTASGFSLS SEQ ID NO: 64: Amino Acid Sequence of HFR1
QSLEESGGRLVTPGTPLTLTCTASGFSL SEQ ID NO: 65: Amino Acid Sequence of HFR2
YTTWVRQAPGQGLEYIGYI SEQ ID NO: 66: Amino Acid Sequence of HFR2
WVRQAPGQGLEYIG SEQ ID NO: 67: Amino Acid Sequence of HFR2
WVRQAPGQGLE SEQ ID NO: 68: Amino Acid Sequence of HFR3
PYYATWAKGRFTISRTSTTVGLKMTSLTTEDTATYFCAR SEQ ID NO: 69: Amino Acid Sequence of HFR3
YATWAKGRFTISRTSTTVGLKMTSLTTEDTATYFCAR SEQ ID NO: 70: Amino Acid Sequence of HFR3
RFTISRTSTTVGLKMTSLTTEDTATYFCAR SEQ ID NO: 71: Amino Acid Sequence of HFR3
YATWAKGRFTISRTSTTVGLKMTSLTTEDTATYFC

II. Therapeutic Uses of H1.0K180Me2 Antibody

A. Treatment of Methylated H1.0-Related Diseases and Conditions

Provided herein are therapeutic H1.0K180me2 antibodies for the treatment of a methylated H1.0-related disease or condition.

As used herein, a "methylated H1.0-related disease or condition" is one where there is an increase in the levels of H1.0K180me2, an increase in the endogenous dimethylation of a H1.0 protein/peptide substrate at K180, an increase in the release of H1.0K180me2 from the chromatin, an increase in the release of H1.0K180me2 from the nucleus into the cytoplasm, an increase in the cytoplasmic deposition of H1.0K180me2, an increase in the levels of H1.0K180me2 in the extracellular space, an increase in the circulating levels of H1.0K180me2 in a bodily fluid (e.g. serum, urine, saliva, cerebrospinal fluid, etc.), and/or an increase in the level of autoantibodies specific for H1.0K180me2.

Methylated H1.0-related diseases and conditions include, but are not limited to, age-related pathologies associated with increase of senescent cells, Alzheimer's disease, radiation exposure, exposure to a genotoxic stressor, conditions that comprise the accumulation of senescent cells associated with external and internal stressors, and autoimmune group of diseases and conditions associated with high level of autoantibodies to H1.0K180me2.

Provided herein are methods of treating a methylated H1.0-related disease or condition in an individual by binding and clearing H1.0K180me2 comprising administering to the individual a therapeutically effective amount of a therapeutic H1.0K180me2 antibody.

As used herein, an individual refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Individuals may be male or female.

The individual can be of any age. In some embodiments of the methods described herein, e.g. for the treatment of Alzheimer's disease, the individual is greater than 50 years old. In some embodiments of the method described herein, the individual is less than 50 years old. In some embodiments, of the methods described herein, the individual is at least 50 years old, is at least 55 years old, is at least 60 years old, is at least 65 years old, is at least 70 years old, is at least 75 years old, or is at least 80 years old. In an exemplary embodiment, the individual is at least 60 years old.

Turning to the methylated H1.0-related diseases and conditions more specifically, exemplary indications are presented below.

Alzheimer's Disease

Figure 9C:
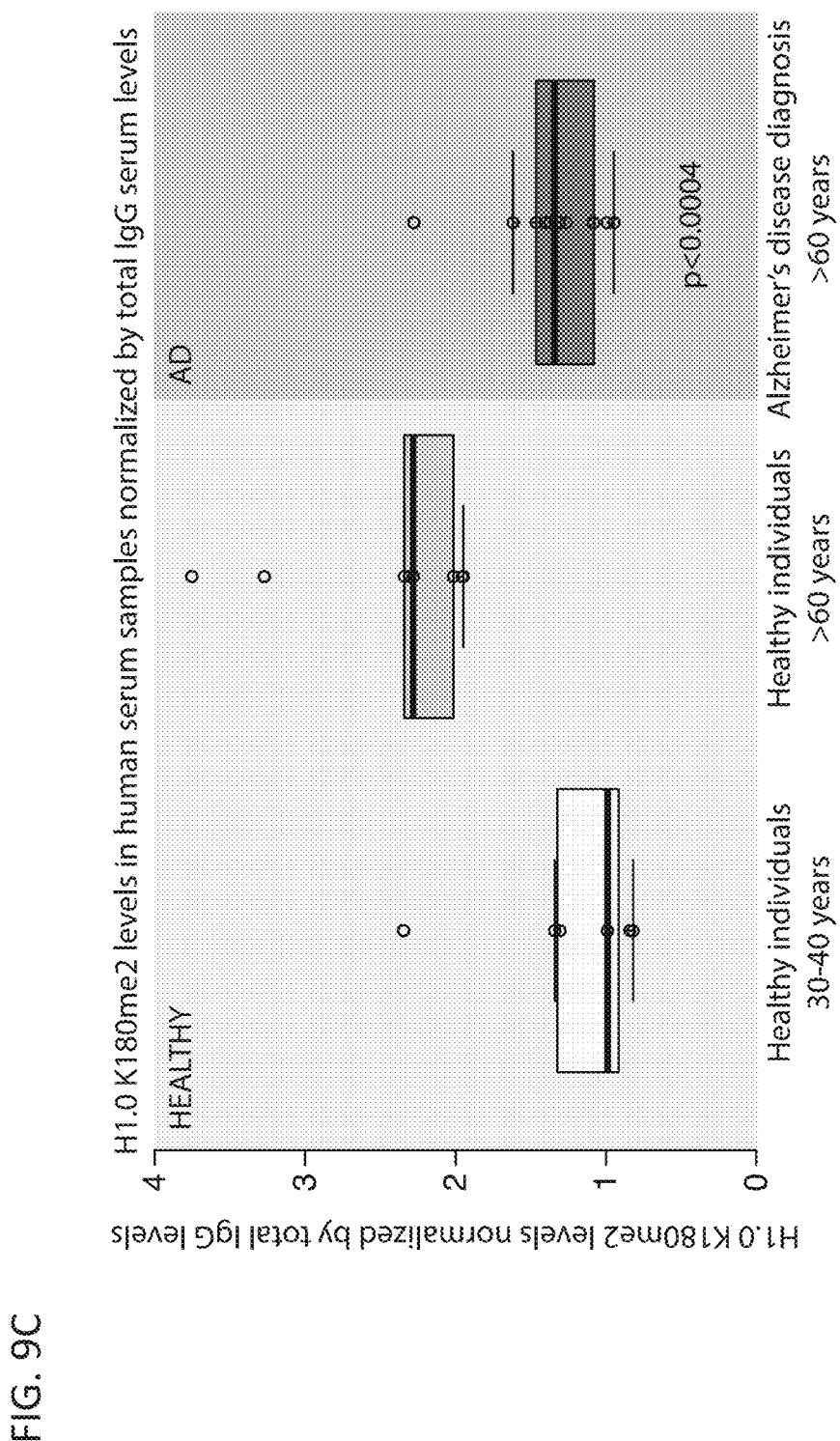

During aging, there is increased accumulation of cytoplasmic H1.0K180me2 in the brain tissue of humans, FIG. 9B. These observations are correlated with an age-related increase of circulating H1.0 K180me2 antigen observed in serological tests (FIG. 9C). Additionally, when whole cell lysates of mouse brain samples from 1 month (young) and 24 month (old) mice were compared by western blot analysis with anti-H1.0K180me2, anti-H1.0, anti-γH2A.X and anti-β-Actin antibodies, H1.0K180me2 levels increased in the 24 month mouse, correlating with increased levels of γH2A.X (FIG. 9A).

Figure 10A:
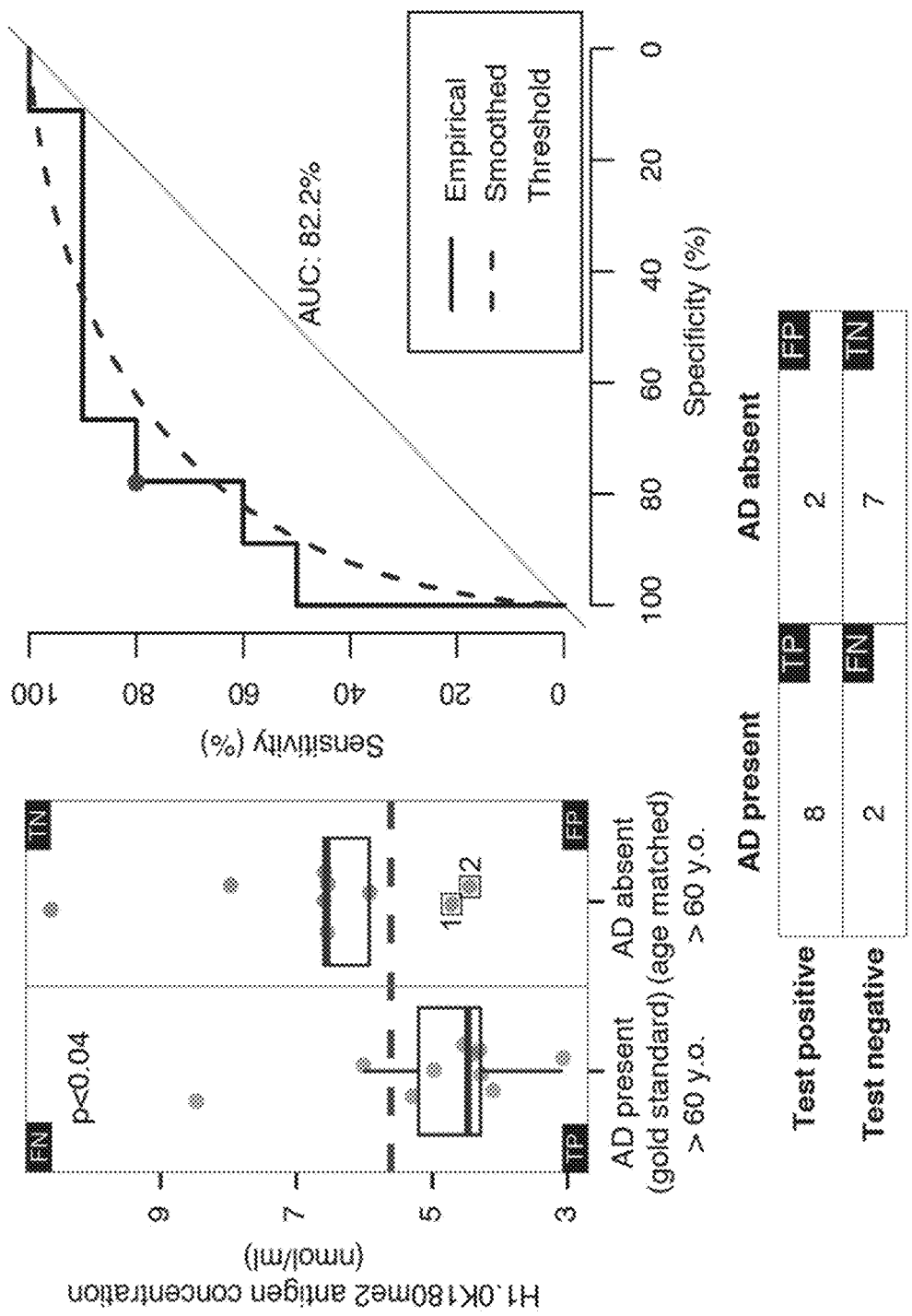
FIGS. 10A-10C demonstrate the utility of measurements of serum H1.0K180me2 as biomarkers of Alzheimer's disease.
Figure 10B:
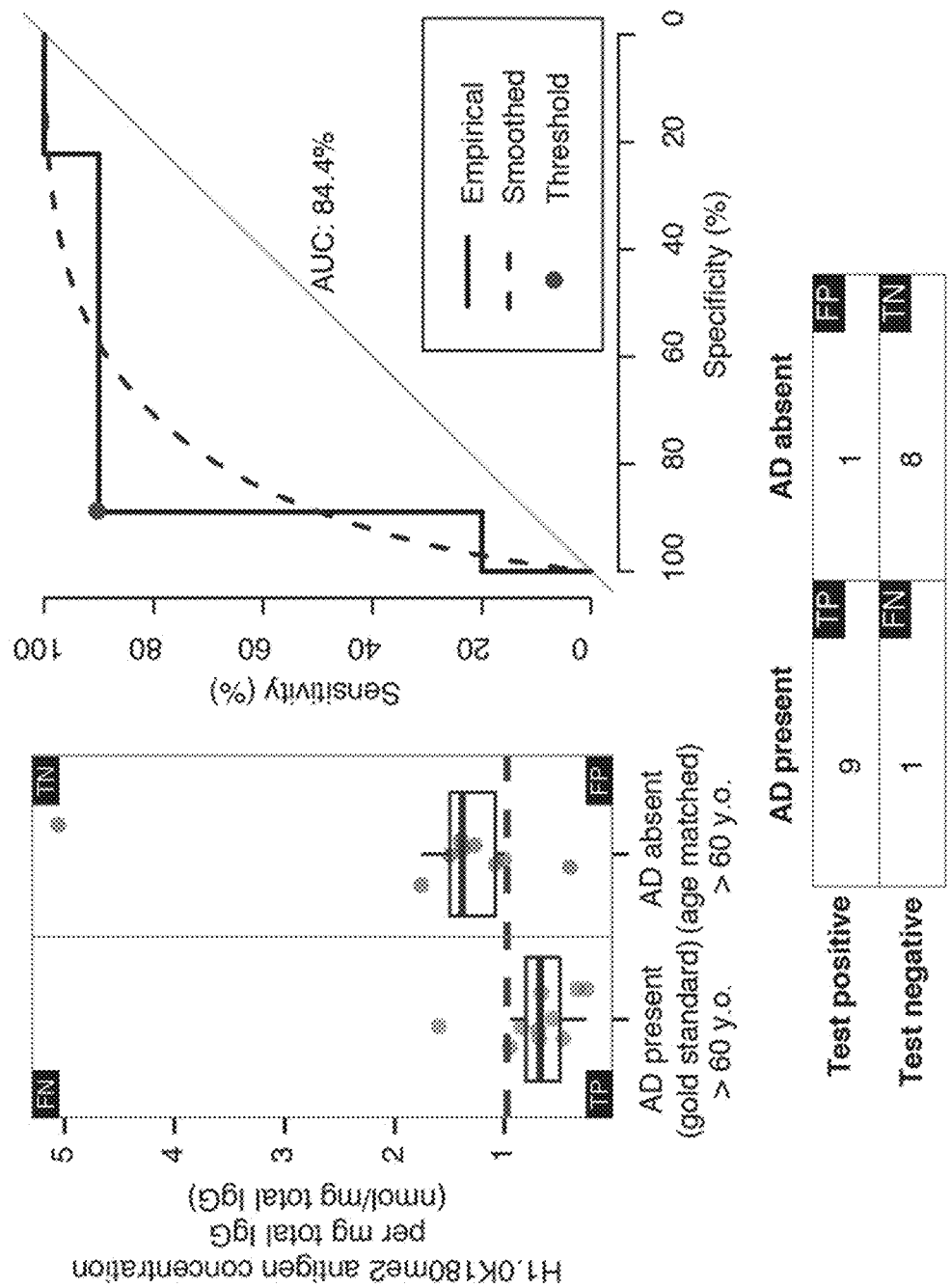
Figure 10C:
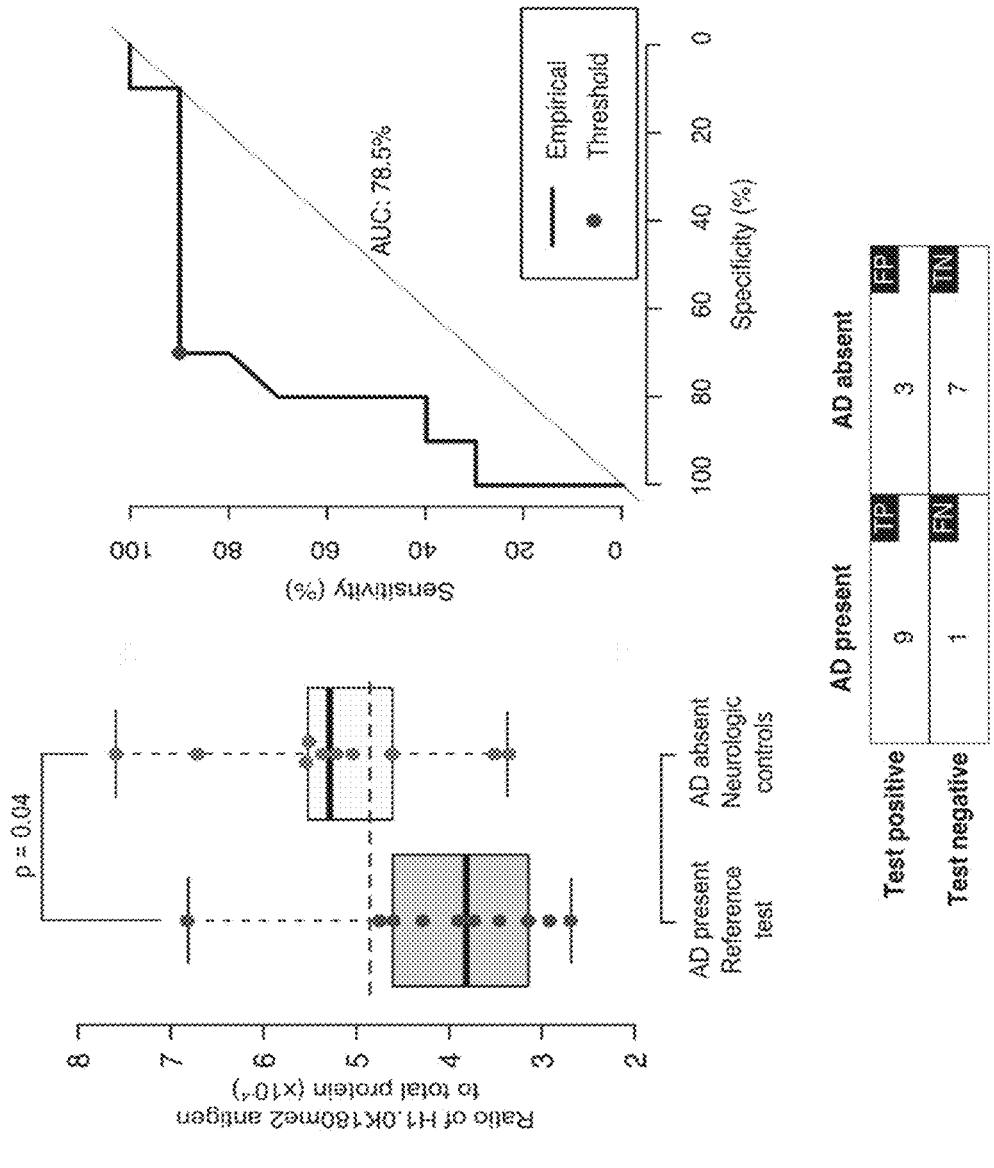

However in individuals diagnosed with Alzheimer's disease, there is a drop in the circulating levels of the H1.0K180me2 antigen observed serological ELISA tests when comparing a control population (no Alzheimer's disease pathology) with a reference control (diagnosed Alzheimer's disease patients) (FIGS. 10A-10C). FIG. 10A shows the quantification of H1.0K180me2 levels determined by slot blot analysis in Alzheimer's disease patients and age-matched controls. Quantification of H1.0K180me2 levels was determined by slot blot analysis in Alzheimer's disease patients and age-matched controls. FIG. 10B shows H1.0K180me2 levels in human serum normalized by total IgG serum levels. FIG. 10C shows H1.0K180me2 levels in human serum normalized by total protein levels. Although serum concentrations of H1.0K180me2 are sufficient for identification of Alzheimer's disease patients, the use of serum sample normalization by total IgG (FIG. 10B) or total protein (FIG. 10C) allows for direct comparisons between individuals regardless of variables which may alter overall serum concentration, such as protocol used to obtain serum, operator variability, hydration state of patient and activity state of patient.

Thus in the context of Alzheimer's disease, treatment with a therapeutically effective amount of an H1.0K180me2 antibody (e.g. a cell penetrating antibody or a cell clearing antibody) is provided.

DNA Damage and Genotoxic Stress

Figure 11A:
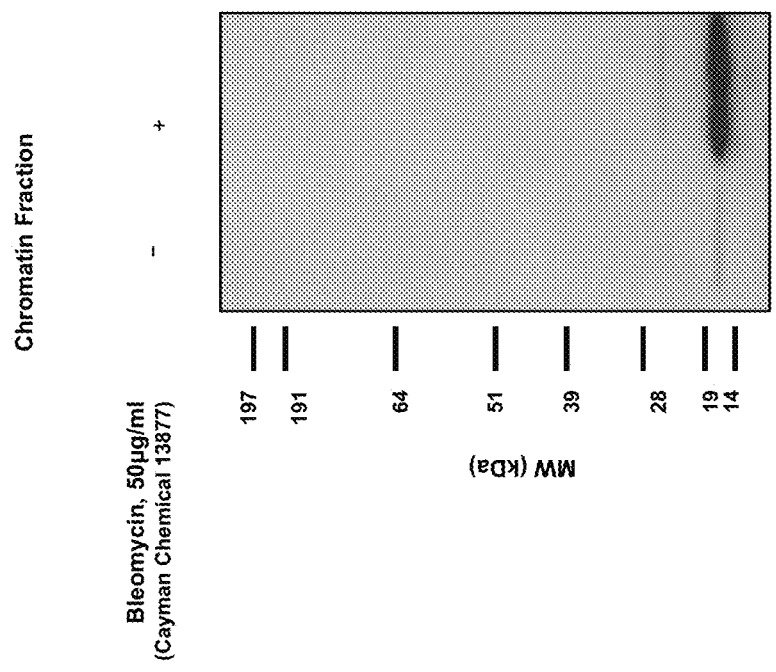
FIG. 11A shows the dimethylation of H1.0K180 (H1.0K180me2) on chromatin immediately after DNA damage, by western blot analysis.

In the context of DNA damaging agents, dimethylation of H1.0K180 (H1.0K180me2) is observed on chromatin following acute DNA damage with bleomycin, a chemotherapeutic agent (FIG. 11A). To assess the relationship between H1.0K180 methylation and DNA damage, SR hADSCs (self-renewing human adipose derived stem cells) and hADSCs treated with DNA damaging agent bleomycin for 2 hours were lysed and fractionated to obtain the chromatin bound fraction. Western blot analysis with an H1.0K180me2 antibody shows methylation of H1.0K180 on the chromatin upon DNA damage (FIG. 11A). Upon treatment of SR hADSCs with bleomycin to induce DNA double-strand breaks, H1.0K180me2 localized to the cytoplasm.

Figure 11B:
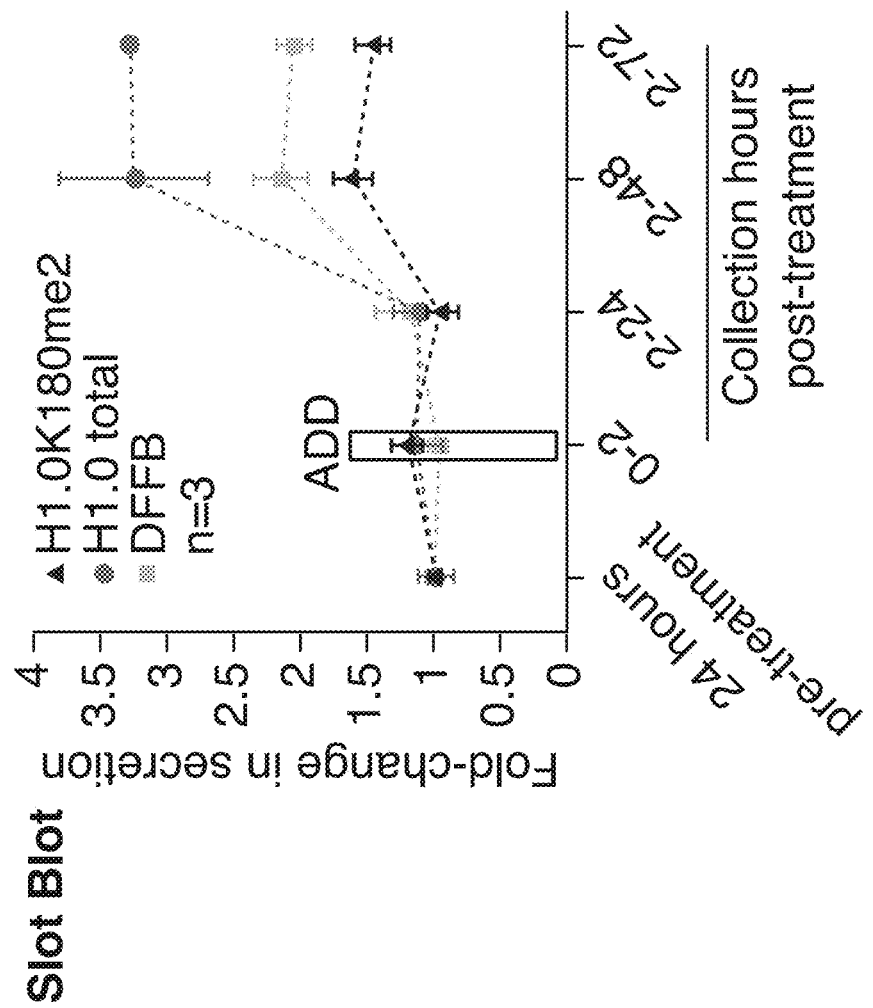
FIG. 11B shows secretion of H1.0K180me2 from after DNA damage.

By slot blot immunoassay, it was found that the presence of H1.0K180me2 was detected in the conditioned medium of hADSCs in a time course dependent manner after genotoxic insult imposed by bleomycin, with maximal H1.0K180me2 secretion detected within 48 hours (FIG. 11B). This signifies secretion out of the cells. An increase in DNA fragmentation factor (DFFB/DFF40/CAD) secretion upon GSI-SEN was seen, in a similar manner, with H1.0K180me2 starting 48 hours after treatment (FIG. 11B). None of the protein is secreted in measurable quantities upon onset of acute DNA damage (ADD).

Figure 12A:
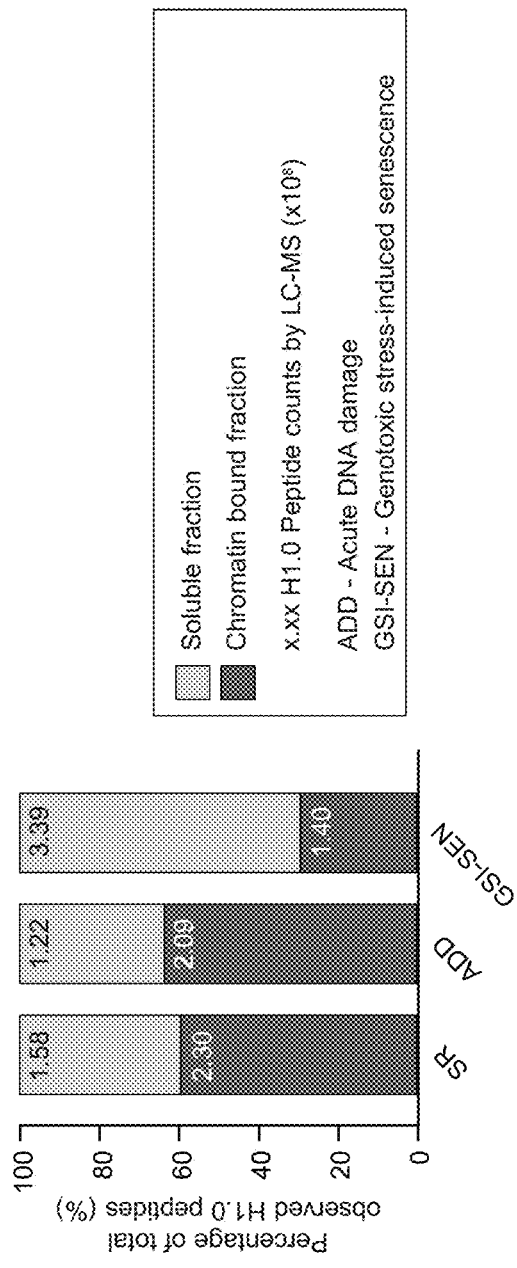
FIGS. 12A and 12B show LC-MS/MS analysis (FIG. 12A) and slot blot analysis (FIG. 12B) on hADSCs of SR, acute DNA damage, and genotoxic stress induced senescence, revealing that dimethylated H1.0K180 (H1.0K180me2) is released from chromatin upon genotoxic stress induced senescence (FIG. 12A) and is secreted out of the cells into the extracellular matrix/cellular media (FIG. 12B).
Figure 12B:

In the context of genotoxic stress, H1.0K180me2 is released from the chromatin upon genotoxic stress induced senescence (days after treatment with a DNA damaging agent) (FIG. 12A) and is secreted out of the cells into the extracellular space (FIG. 12B). As shown in FIG. 12A, Chromatin bound H1.0 decreased from ~60% of total in SR and acute DNA damage, to ~30% of total upon genotoxic stress induced senescence. Culture media from SR hADSCs treated with bleomycin was collected for slot blot analysis with α-H1.0 and α-H1.0K180me2 antibodies to assess secretion of H1.0 to the extracellular matrix (ECM). Secreted H1.0 was detectable in the cell culture media, and after 24 hours of bleomycin treatment, secreted H1.0K180me2 was also readily detected (FIG. 12B). These results confirmed that methylated H1.0K180 is released from chromatin upon genotoxic stress induced senescence and is secreted into the ECM.

Thus in the context of DNA damage and genotoxic stress, treatment with a therapeutically effective amount of an H1.0K180me2 antibody (e.g. a cell penetrating antibody, or a cell-clearing antibody) is provided.

Radiation Exposure

Figure 13A:
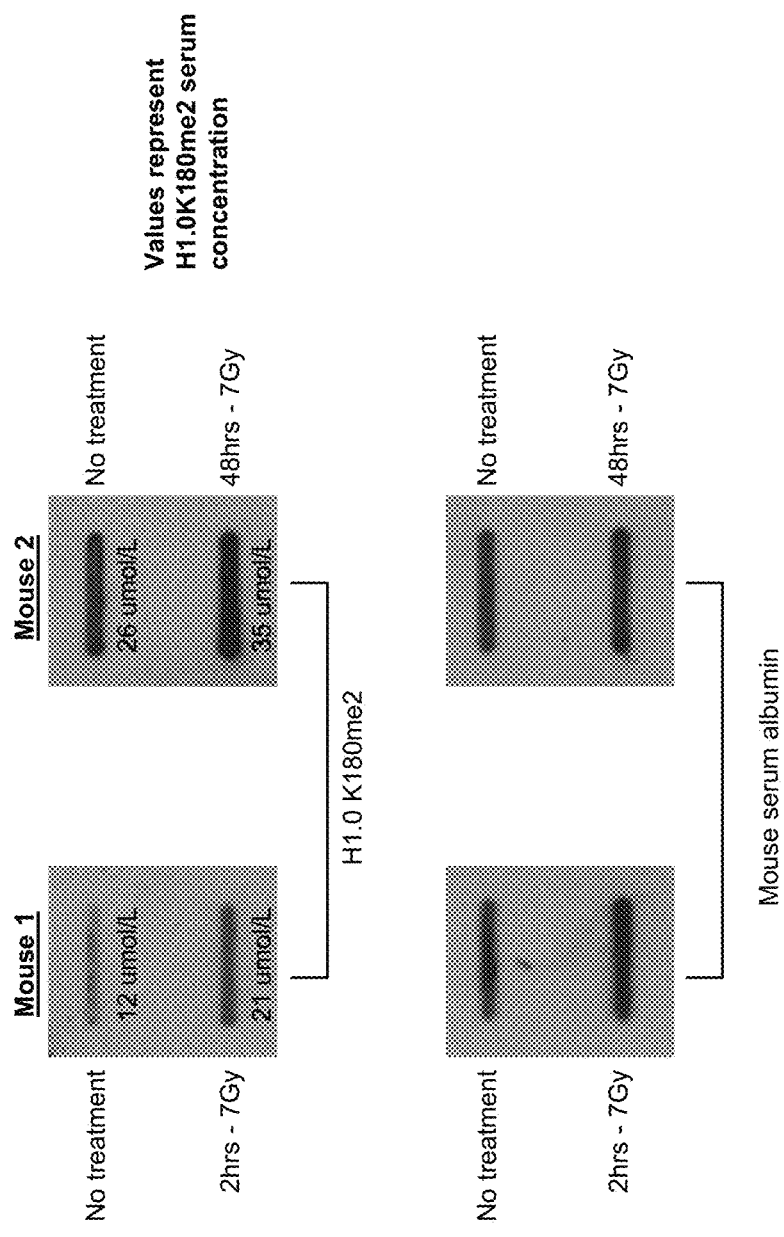
FIGS. 13A-13C show the effect of ionizing radiation on H1.0K180me2 levels.
Figure 13C:
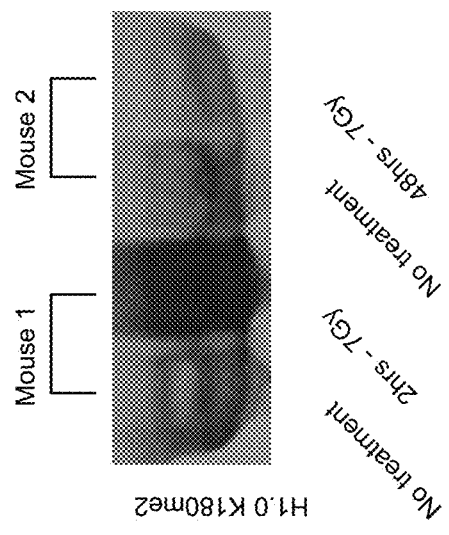
Figure 13B:
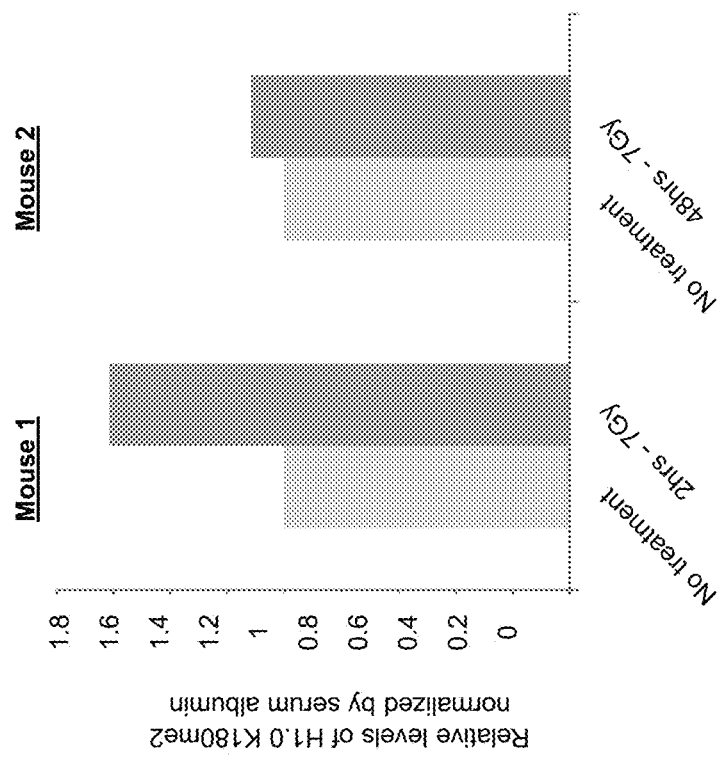

In the context of radiation exposure, exposure to ionizing radiation induces increased levels of circulating H1.0 K180me2 in serum (FIG. 13A and FIG. 13B. The effect of ionizing radiation on H1.0K180me2 levels in serum was examined. Serum was collected from wild-type mice before and either 2 hours or 48 hours after exposure to 7 Gy of ionizing radiation. H1.0K180me2 serum levels 2 hours (mouse 1) or 48 hours (mouse 2) after irradiation were compared to initial levels before treatment using slot blot and immunoblotting with α-H1.0K180me2 antibody (FIG. 13A). The concentration of H1.0K180me2 in each serum sample was calculated using a standard curve of H1.0K180me2 peptide included in each analysis. Mouse serum albumin was used as a loading control. H1.0K180me2 dot blot bands were quantified and normalized by serum albumin. Relative increases in H1.0K180me2 after irradiation are shown (FIG. 13B). Western blot analysis of equal volumes of mouse serum with α-H1.0K180me2 antibody also showed increased H1.0K180me2 after irradiation (FIG. 13C).

Thus in the context of radiation exposure, treatment with a therapeutically effective amount of an H1.0K180me2 antibody (e.g. a cell penetrating antibody or a cell clearing antibody) is provided.

B. Therapeutic H1.0K180Me2 Antibodies

As discussed in the above Section (I)(A), provided herein are antibodies that recognize and selectively and/or specifically bind to the H1.0K180me2 epitope, and may be used for therapeutics.

In some embodiments, the therapeutic antibody is a neutralizing antibody, and the antibody neutralizes one or more biological activities of H1.0K180me2. For example, the antibody may bind extracellular H1.0K180me2 and neutralize any binding or signaling activity it may possess. In some embodiments, the antibody may clear or block H1.0K180me2 in a cell, or a sample. In some embodiments, the antibody may clear the cells comprising H1.0K180me2.

In some embodiments, the therapeutic antibody may clear senescent cells. In some embodiments, the antibody may clear cells/tissue or protein products that give rise to the symptom of Alzheimer's disease. In some embodiments, the antibody may clear cells damaged by radiation damage, DNA damaging agents, and other genotoxins. In some embodiments, the antibody is a cell-penetrating antibody. In other embodiments, the affected cells' membranes are comprised and allow for entry of the therapeutic H1.0K180me2 antibodies provided herein.

In some embodiments, the therapeutic antibody provided herein has antibody-dependent cellular cytotoxicity (ADCC) activity. Effector cells bearing Fc gamma receptors (FcγR or FCGR) on their cell surface, including cytotoxic T-cells, natural killer (NK) cells, macrophages, neutrophils, eosinophils, dendritic cells, or monocytes, recognize and bind the Fc region of antibodies bound to the target-cells. Such binding may trigger the activation of intracellular signaling pathways leading to cell death.

In some embodiments, the therapeutic antibody has complement-dependent cytotoxicity (CDC) activity. Antibody-induced CDC is mediated through the proteins of the classical complement cascade and is triggered by binding of the complement protein Clq to the antibody. Antibody Fc region binding to Clq may induce activation of the complement cascade.

In some embodiments, the therapeutic antibody has antibody-dependent cellular phagocytosis (ADCP) activity. Phagocytic cells bearing Fc receptors on their cell surface, including monocytes and macrophages, recognize and bind the Fc region of antibodies bound to target-cells. Upon binding of the Fc receptor to the antibody-bound target cell, phagocytosis of the target cell may be initiated.

In some embodiments, the therapeutic antibodies may form an immune complex. For example, an immune complex may be a cell expressing or extruding H1.0K180me2 antigen, covered by antibodies.

C. Combination Therapies

The administration of any of the therapeutic H1.0K180me2 antibodies provided herein may be administered in combination with other known drugs/treatments for the diseases which manifest in H1.0 methylation.

In the context of Alzheimer's disease prevention, any of the therapeutic H1.0K180me2 antibodies may be administered in combination with the administration of an Alzheimer's disease preventive drug or regimen which include, but are not limited to, APP synthesis Inhibitors, beta-secretase inhibitors, gamma-secretase inhibitors and modulators, AB aggregation inhibitors, AB immunotherapy, Cholesterol-lowering drugs, Anti-tau drugs, cholinesterase inhibitors, N-methyl D-aspartate (NMDA) antagonists, atypical antipsychotics, blockers of protein S-nitrosylation, glucagon-like peptide-1 receptor agonists, rapamycin, rapalogues, endocannabinoids, cannabinoids, neuroprotectors, molecules controlling calcium influx, antioxidants, anti-inflammatory drugs, drugs controlling control of glutamate homeostasis, autophagy inducers, hormones, hormonal regulators, statins, insulin, insulin carriers, multifunctional nanocarriers, vitamins, nutritional supplements, small RNA molecules, peptides, and ultrasound therapy.

E. Administration of the Therapeutic H1.0K180Me2 Antibodies

In vivo administration of the therapeutic H1.0K180me2 antibodies described herein may be carried out intravenously, intramuscularly, subcutaneously, topically, orally, transdermally, intraperitoneally, intraorbitally, by implantation, by inhalation, intrathecally, intraventricularly, or intranasally. An effective amount of the therapeutic may be administered for the treatment of the disease or condition manifesting in H1.0 methylation. The appropriate dosage of the therapeutic may be determined based on the type of disease or disorder to be treated, the type of the therapeutic antibody, the severity and course of the disease or condition, the clinical condition of the individual, the individual's clinical history and response to the treatment, and the discretion of the attending physician. In an exemplary embodiment, any one of the H1.0K180me2 antibodies provided herein is administered intravenously.

For in vivo administration of the therapeutic H1.0K180me2 antibodies described herein, normal dosage amounts may vary from about 1 ng/kg up to about 1000 mg/kg of an individual's body weight or more per day, depending upon the route of administration. For repeated administrations over several days or longer, depending on the severity of the methylated H1.0-related disease or condition to be treated, the treatment may be sustained until a desired suppression of symptoms is achieved. Dosage regimens may be useful, depending on the pattern of pharmacokinetic decay that the physician wishes to achieve. For example, dosing an individual from one to twenty-one times a week is provided herein. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is may be monitored by conventional techniques and assays. The dosing regimen may vary over time independently of the dose used.

E. Pharmaceutical Compositions

The present application provides compositions comprising therapeutic H1.0K180me2 antibodies including pharmaceutical compositions comprising any one or more of the therapeutic antibodies described herein. The pharmaceutical compositions may further comprise one or more pharmaceutically acceptable excipients. In some embodiments the composition is sterile.

F. Therapeutic Kits and Articles of Manufacture

The present application provides kits comprising therapeutic H1.0K180me2 antibody compositions described herein. In some embodiments, the kits further contain a component selected from any of secondary antibodies, reagents for immunohistochemistry analysis, pharmaceutically acceptable excipient and instruction manual and any combination thereof. In some embodiments, the kit comprises any one or more of the therapeutic compositions described herein, with one or more pharmaceutically acceptable excipients.

The present application also provides articles of manufacture comprising any one of the therapeutic compositions or kits described herein. Examples of an article of manufacture include vials (e.g. sealed vials).

III. Diagnostic Uses of H1.0K180Me2 Antibody

A. Detection of the H1.0K180me2 antigen

Provided herein are antibodies that specifically bind the H1.0K180me2 antigen, useful for diagnostics. The H1.0K180me2 antibodies provided herein require dimethylation of the K180 residue for binding. H1.0K180me2 antibodies are discussed in more detail in the preceding Section I(A).

Figure 8:
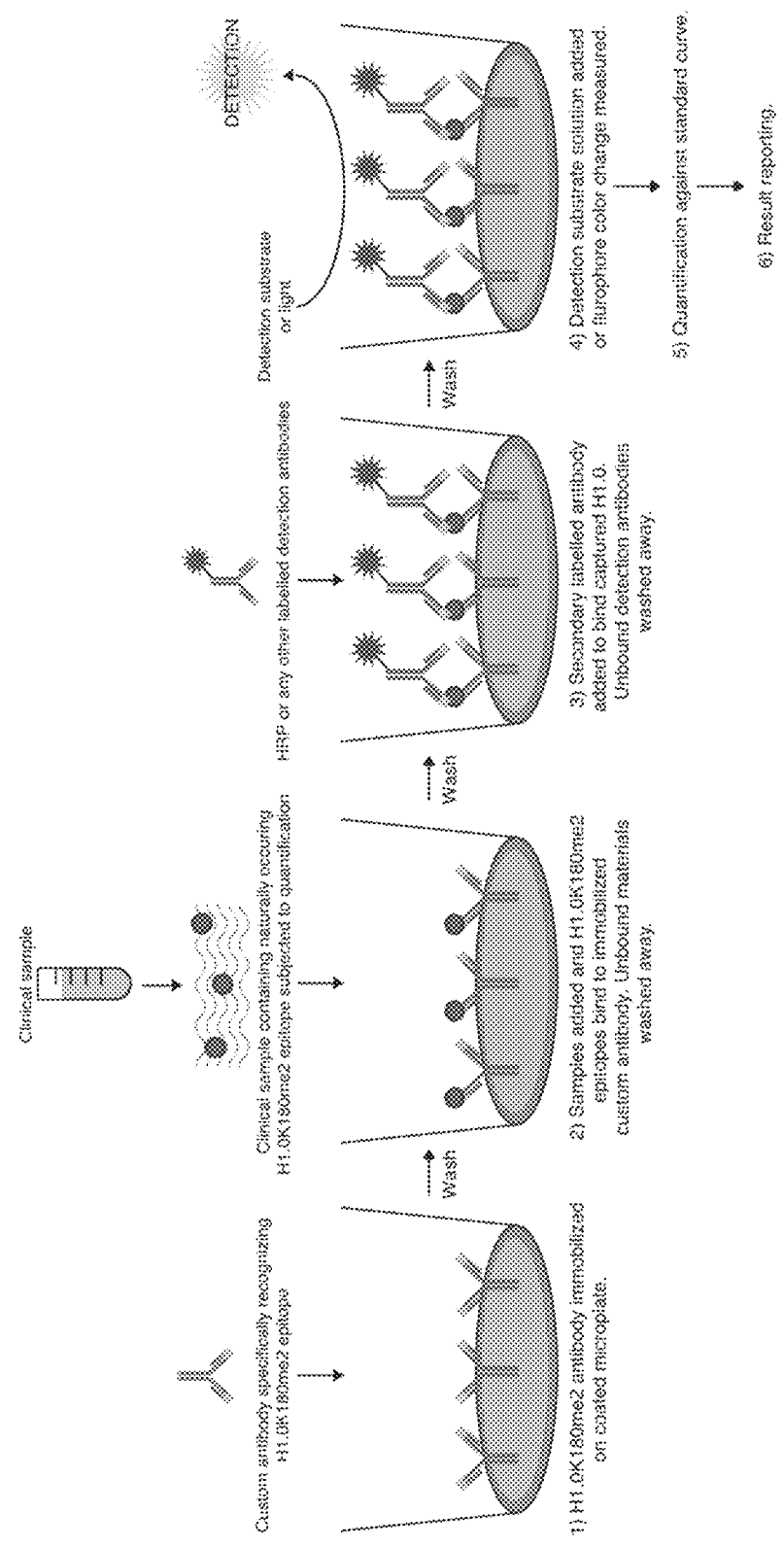
FIG. 8 shows an exemplary use of an ELISA for the direct detection of H1.0K180me2 epitope in samples of bodily fluids.

FIG. 8 depicts the exemplary use of an ELISA for the direct detection of H1.0K180me2 epitope in samples of bodily fluids. In this exemplary scheme, an antibody specific to an H1.0K180me2 epitope is provided, and is immobilized (coated) on a microplate. A clinical sample containing an H1.0K180me2 epitope for quantification is provided. The sample is added to the microplate, and the H1.0K180me2 epitope binds to the immobilized antibodies. Unbound materials are washed away. Detection antibodies are then added, for example an HRP or any other labelled antibodies. These detection antibodies bind the capture epitope. Unbound detection antibodies are washed away. A detection substrate solution is added, and a fluorophore or color change is measured. This is then quantified against a standard curve to report levels of H1.0K180me2 epitope in the clinical sample.

Provided herein are assays for the detection and quantification of the concentration of H1.0K180me2. Such quantification may be useful for detecting replicative senescence, DNA damage, genotoxic stress, radiation exposure, Alzheimer's disease, and biological aging. The quantification may also useful for monitoring therapeutic regimens, drug screening, and stratification of patients as responders or non-responders to drug treatments aimed to restore cell viability, prevent DNA damage, increase cellular metabolism and autophagy, inhibit cellular senescence and block insoluble protein waste accumulation in cellular cytoplasm. Depending on the application, H1.0K180me2 may be detected and quantified in vivo, in vitro, ex vivo, in situ, or in a cell-free system. For instance, quantification may involve contacting a biological sample in vitro with an antibody as disclosed herein, and determining the concentration and/or subcellular localization of a protein comprising an H1.0K180me2 antigen or a peptide thereof in the sample that binds the antibody.

H1.0K180me2 may be detected by any number of methods well known to those of skill in the art. The H1.0K180me2 antibodies provided herein are readily used in a variety of immunoassays. These immunoassays include, but are not limited to enzyme-linked immunosorbent assay (ELISA), Western blot, radioimmunoassay (MA), flow cytometry, lateral flow immunoassay, slot blot, magnetic immunoassay, a radioimmunoassay, indirect immunofluorescence assay, direct immunofluorescence assay, surround Optical Fiber Immunoassay (SOFIA), spectrophotometry, radiography, electrophoresis, immunoelectrophoresis, capillary electrophoresis, high performance liquid chromatography (HPLC), thin layer chromatography (TLC), hyperdiffusion chromatography, fluid or gel precipitation reactions, immunodiffusion, spectrometry, mass spectrometry, quantitative mass-spectrometry, any type of multiplex assay, and any type of microfluidic assay.

The H1.0K180me2 antibodies provided herein may be conjugated to a label (e.g. conjugated to a label) for example a detectable label, a spin label, a colorimetric label, a radioactive label, an enzymatic label, a fluorescent label, or a magnetic label.

The H1.0K180me2 antibodies provided herein may be conjugated to a detectable label. The detectable group may be any material having a detectable physical or chemical property, for example detectable by spectroscopic, photochemical, biochemical, immunochemical, fluorescent, electrical, optical or chemical methods. Useful labels in the present disclosure include, but are not limited to, magnetic beads (e.g. DYNABEADS®), fluorescent dyes (e.g., fluorescein isothiocyanate, red, rhodamine, and the like), radio-labels (e.g., 3H, 125I, 35S, 14C, or 32P), enzymes (e.g., LacZ, CAT, horseradish peroxidase, alkaline phosphatase and others, commonly used as detectable enzymes, either as marker gene products or in an ELISA), biotin, avidin, or streptavidin and colorimetric labels such as colloidal gold colored glass or plastic (e.g. polystyrene, polypropylene, latex, etc.) beads, and nanoparticles. In an exemplary embodiment, biotin is the label.

The labels provided herein may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions. Labels are often attached by indirect methods. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands may be used. Where a ligand has a natural anti-ligand, for example, biotin, it may be used in conjunction with the labeled, naturally occurring anti-ligands. Alternatively, any haptenic or antigenic compound may be used in combination with an antibody. Components can also be conjugated directly to signal-generating compounds, e.g., by conjugation with an enzyme or fluorophore. Enzymes of interest as labels include, but are not limited to, hydrolases, phosphatases, esterases, glycosidases, or oxitranscription factoreductases, and peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol.

Methods of detecting labels are well known to those of skill in the art. Thus, for example, where the label is a radioactive label, methods for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Upon detection, the concentration of H1.0K180me2 in a particular fraction may be quantified, for example quantification of H1.0K180me2 in an intra-cellular fraction, in a soluble and chromatin bound fraction, or in a cytoplasmic fraction. For example, an increase in the concentration of H1.0K180me2 in a cytoplasm fraction is indicative of a senescent state of the cells. In some embodiments intact cells, cells in culture, or cells in slice culture are imaged to visualize the localization of an H1.0K180me2. For example, an increase in a non-nuclear sub-localization of H1.0K180me2 is indicative of a senescent state. In some embodiments release of H1.0K180me2 into the cytosol or extracellular matrix is indicative of a senescent state.

Detection may be carried out on any biological sample. Biological samples include, but are not limited to whole blood, plasma, serum, saliva, urine, feces, synovial fluid, cerebrospinal fluid, bronchial lavage, ascites fluid, bone marrow aspirate, pleural effusion, tissue, cells, a biopsy, interstitial fluid, lymphatic fluid, or fractions thereof derived from the individual. In some embodiments, the biological sample comprises cells and the cells are in culture, in a suspension, on a slide, in intact tissue, or in preparation ready for a FACs analysis.

Biological samples are obtained from individuals. As used herein, an individual refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Individuals may be male or female. In some embodiments, the individual is a female. In some embodiments, the individual is a male.

In the diagnostic methods provided herein, the individual may be of any age. In some embodiments where detection of Alzheimer's disease is carried, the individual can be greater than 50 years old. In some embodiments of the method described herein, the individual is less than 50 years old. In some embodiments, of the methods described herein, the individual is at least 50 years old, is at least 55 years old, is at least 60 years old, is at least 65 years old, is at least 70 years old, is at least 75 years old, or is at least 80 years old. In an exemplary embodiment, the individual is at least 60 years old.

Biological samples are obtained according to standard methods well known to those of skill in the art. The sample is optionally pretreated as necessary by dilution in an appropriate buffer solution or concentrated, if desired. Any of a number of standard aqueous buffer solutions, employing one of a variety of buffers, such as phosphate, Tris, or the like, at physiological pH may be used.

The direct detection methods described herein may be used to quantify the concentration of H1.0K180me2 in the biological sample. In some embodiments, an H1.0K180me2 protein or peptide may be used in tandem, for example, as a positive control or as competitor in a competitive immunoassay, and may be labeled or not, depending on the format of the assay to be carried out.

One of skill will appreciate that in some embodiments, it may be necessary to compare the determined concentrations of the H1.0K180me2 antigen to a control (i.e. reference control). The relative comparison may allow, for example, for the determination of whether an individual has, or is at risk of developing a disease (e.g. Alzheimer's disease) or whether the individual is responsive, or may be responsive to a particular treatment (e.g. an Alzheimer's disease treatment; or a treatment with a rapalogue). Controls may be age-matched controls; sex-matched controls; age- and sex-matched controls; healthy controls; unmanipulated controls; or a reference standard representing a compilation of reference standards. The comparisons can also be made to a sample from the same individual prior to a treatment (e.g. with an Alzheimer's disease treatment or rapalogue treatment) or prior to an exposure to a genotoxin, DNA-damaging agent, or radiation, for example. The comparisons can also be made to a sample from the same individual from an unaffected area, for example from an unaffected tissue.

One of skill will appreciate that it is often desirable to reduce non-specific binding in immunoassays and during analyte detection. Where the assay involves H1.0K180me2 antibodies immobilized on a solid substrate, it may be desirable to minimize the amount of non-specific binding to the substrate. Methods of reducing such non-specific binding are known to those of skill in the art. Typically, this involves coating the substrate with a proteinaceous composition. In some embodiments, protein compositions such as bovine serum albumin (BSA), nonfat powdered milk, and gelatin may be utilized.

The sensitivity, specificity, positive and negative predictive values (PPV and NPV) as well as positive and negative likelihood ratios (PLR and NLR)) can be calculated for each diagnostic test design. The statistical methods help to predict the presence or absence of disease in the patients.

Sensitivity is generally the probability that the test result will be positive when disease is present (true positive rate).

Specificity is generally the probability that a test result will be negative when the disease is not present (true negative rate).

The positive predictive value (PPV) generally is the probability that the disease is present when the test is positive, accounting for the pre-test prevalence of the disease (e.g. pre-test prevalence for Alzheimer's disease is 10%).

The negative predictive value (NPV) is generally the probability that the disease is not present when the test is negative, accounting for the pre-test prevalence of AD as 10% (Prince, M. J., Am J Epidemiol, 1996).

The positive likelihood ratio (LR+ or PLR) is generally the probability of a person who has the disease testing positive divided by the probability of a person who does not have the disease testing positive. Positive likelihood ratios (PLR) generally indicate how much to increase the probability of the disease, if the test is positive. A PLR>1 indicates an increase probability that the target disorder is present, a PLR<1 indicates a decreased probability that the target disorder is present, and a PLR=1 means that test does not change the probability of the disease.

The negative likelihood ratio (LR− or NLR) is generally the probability of a person who has the disease testing negative divided by the probability of a person who does not have the disease testing negative. Negative likelihood ratios (NLR) generally indicate how much to decrease the probability of the disease, if the test is negative.

In some embodiments, the comparison will be made to a threshold level established by a Receiver Operating Characteristic curve analysis for optimal specificity and sensitivity. The ROC curve, thresholds and areas under the curve (AUC) are shown for each of the test's designs provided herein.

In some embodiments, the diagnostic methods provided herein may be used for confirmatory tests, e.g. to definitively confirm that an individual has a disease, e.g. Alzheimer's disease.

In other embodiments, the diagnostic methods provided herein may be used for their predictive value (for testing, screening), e.g. to determine the likelihood that an individual will develop a disease, e.g. Alzheimer's disease. In such embodiments, the diagnostics may involve computation of likelihood ratios.

In other embodiments, the diagnostic methods provided herein may be used as a companion diagnostic. In such embodiments, the diagnostics may involve computation of positive predictive values (PPV) and negative predictive values (NPV).

In some embodiments, the diagnostic methods provided herein may be used to establish a diagnostic odds ratio (OR). In such embodiments, the diagnostic may involved computation of sensitivity and specificity and is a measure of the effectiveness of a diagnostic test.

The H1.0K180me2 antibodies provided herein are useful for a variety of diagnostic purposes, discussed below.

B. Detection of Alzheimer's Disease

Provided herein are H1.0K180me2 antibodies (to determine H1.0K180me2 levels), for use in the screening of individuals for Alzheimer's disease, for use in identifying whether individuals are at risk for developing Alzheimer's disease, for use in estimating the likelihood of whether individuals will develop Alzheimer's disease, for use in the diagnosis of Alzheimer's disease, for use in the early detection of Alzheimer's disease, for use in the prognosis of Alzheimer's disease, for selecting individuals who may respond to an Alzheimer's disease treatment with an Alzheimer's disease drug or regimen for use in treatment selection/determining treatment options for those diagnosed with Alzheimer's disease, for use in monitoring the treatment of those diagnosed with Alzheimer's disease and receiving ongoing treatment with an Alzheimer's disease drug or regimen, or for use in screening for Alzheimer's disease drugs and regimens.

Alzheimer's disease patients displayed lower concentrations of H1.0K180me2 than healthy age-matched healthy controls, indicating that H1.0K180me2 concentrations may effectively segregate patients with Alzheimer's disease from healthy individuals (FIG. 10A). Although serum concentrations of H1.0K180me2 were sufficient for identification of Alzheimer's disease patients, the use of a serum sample normalization by total IgG (FIG. 10B) or total protein (FIG. 10C) allowed for direct comparisons between individuals regardless of variables which may alter overall serum concentration, such as protocol used to obtain serum, operator variability, hydration state of patient and activity state of patient. For example, it was observed that H1.0K180me2 serum levels were elevated in healthy aged individuals relative to healthy younger individuals, while patients with Alzheimer's disease exhibited significantly lower normalized serum levels of H1.0K180me2 relative to healthy aged, individuals (>60 years) (FIG. 10B, 10C).

Exemplary Methods, H1.0K180Me2 Levels:

More specifically, in some embodiments, provided herein are methods using an H1.0K180me2 antibody, to determine H1.0K180me2 levels, for screening an individual for Alzheimer's disease, for identifying an individual is at risk for developing Alzheimer's disease, estimating the likelihood of whether an individual will develop Alzheimer's disease, for determining whether an individual has Alzheimer's disease, for detecting the early signs of Alzheimer's disease in an individual, and for use in the prognosis of Alzheimer's disease in an individual, the method comprising: (a) contacting a biological sample from the individual with an H1.0K180me2 antibody; and (b) determining the concentration of H1.0K180me2 in the sample that binds the antibody, wherein a decrease in the concentration relative to a control indicates that the individual has Alzheimer's disease, is at risk of developing Alzheimer's disease, or has a greater likelihood of developing Alzheimer's disease, and wherein an increase or no change in the concentration relative to a control may indicate that the individual does not have Alzheimer's disease, is not at risk of developing Alzheimer's disease, or does not have a greater likelihood of developing Alzheimer's disease. A control includes, but is not limited to, a healthy control (e.g. age-matched, sex-matched), a reference standard representing a compilation of healthy controls, or a control sample from the same individual isolated earlier in time. In some embodiments, the concentration of circulating H1.0K180me2 is determined. In some embodiments, the change in the concentration is relative to a threshold established by a Receiver Operating Characteristic curve analysis for optimal specificity and sensitivity. In some embodiments, the method further comprises treating the individual with an Alzheimer's disease drug or regimen if it is determined that the individual has, or is at risk of developing, Alzheimer's disease.

In related embodiments, the methods provided herein are used in observational studies. Examples of observational studies include, but are not limited to: (a) Cross-sectional design (single time point design, or delayed cross-sectional)—testing of one or few specimens/samples per patient that are collected at a single time-point; (b) Longitudinal design—testing of multiple specimens/samples per patient that are collected over an extended period of time (e.g. weeks, months, years); (c) Retrospective design—testing of previously collected specimens for which the analyte status and the patient's clinical status is known (characterized specimens) prior to the commencement of the study; (d) Prospective design—testing of specimens collected before or during the study but for which both the analyte status and the patient's clinical status are established during the study; and (e) Prospective-retrospective design—testing of previously collected specimens for which the clinical status is known but the analyte status is unknown and will be established during the study.

In related embodiments, the methods provided herein are intended for the diagnosis of Alzheimer's disease, wherein the methods may be used to determine, verify or confirm a patient's clinical condition as a sole determinant. In these embodiments, this type of testing also includes sole confirmatory assays (to verify results of previous testing) and sole exclusion assays (to rule out a particular condition).

In related embodiments, the methods provided herein are intended to provide an "aid-to-diagnostic" of Alzheimer's disease, wherein the methods may be used to provide additional information to assist in the determination or verification of a patient's clinical status. The test is not necessarily the sole determinant but may be used to evaluate a patient's current state.

In related embodiments, the methods provided herein are intended for the screening of Alzheimer's disease, wherein the methods may be used to determine the status of a disease, disorder or other physiological state in an asymptomatic individual. Depending on the nature of the condition and the targeted patient population, the screening methods may be used routinely or may be restricted to "at risk" patients. In this context the methods described herein used to evaluate a patient's current state.

In related embodiments, the methods provided herein are intended to determine the predisposition to Alzheimer's disease, wherein the methods described herein may be used to determine the likelihood of disease onset (e.g. assessing the risk of developing the disease in future) in pre-symptomatic patients, where for patients at sufficient risk (as determined by test results), preventive interventions may be taken.

In related embodiments, the methods provided herein are intended for the prognosis of Alzheimer's disease, wherein the methods described herein may be used to measure factors linked to a clinical outcome, irrespective of treatment. The methods described herein may be used to estimate the natural progression of a disease (e.g. outcome in the absence of treatment), or to the methods described herein are designed to evaluate a patient's future state.

In related embodiments, the methods provided herein are intended for determination of physiological status of aging population ("aging clock") wherein the methods described herein may be used to evaluate the physiological state of an individual for the purpose of identifying a human condition or characteristic of aging or risk of Alzheimer's disease with aging.

In related embodiments, the quantification of H1.0K180me2 antigen and/or quantification of H1.0K180me2 autoantibodies may be used to increase confidence in the Alzheimer's disease screening, diagnosis, or detection.

In related embodiments, the quantification of H1.0K180me2 antigen and/or quantification of H1.0K180me2 autoantibodies may be used in conjunction with other Cerebrospinal Fluids (CSF) tests including but not limited to the measurement of $A\beta_{42}$, T-tau, p-tau, $A\beta_{42}$/T-tau ratio, and $A\beta42$/p-tau.

In related embodiments, the quantification of H1.0K180me2 antigen and/or quantification of H1.0K180me2 autoantibodies may be used in conjunction with assessment of cognitive status tests, for example the MMSE (mini-mental state examination), GDS (global deterioration rate), and CDR (clinical, Dementia rating) tests.

In related embodiments, the quantification of H1.0K180me2 antigen and/or quantification of H1.0K180me2 autoantibodies may be used in conjunction with neuroimaging.

In some embodiments of the methods described herein, the levels of H1.0K180me2 may be normalized against total IgG in the biological sample or normalized against total protein in the biological sample. In some embodiments of the methods described herein, the concentration of H1.0K180me2 may be determined as a relative ratio to non-methylated, labeled, synthetic H1.0 peptide.

In embodiments of the methods described herein, the individual is greater than 50 years old. In some embodiments of the method described herein, the individual is less than 50 years old. In some embodiments, of the methods described herein, the individual is at least 50 years old, is at least 55 years old, is at least 60 years old, is at least 65 years old, is at least 70 years old, is at least 75 years old, or is at least 80 years old. In an exemplary embodiment, the individual is at least 60 years old.

C. Companion Diagnostics for Alzheimer's Disease

Also provided herein are H1.0K180me2 antibodies (to determine H1.0K180me2 levels), for use in methods for selecting individuals who may respond to an Alzheimer's disease treatment with an Alzheimer's disease drug or regimen, for use in treatment selection/determining treatment options for those diagnosed with Alzheimer's disease, for use in monitoring the treatment of those diagnosed with Alzheimer's disease and receiving ongoing treatment with an Alzheimer's disease drug or regimen, or for use in screening for Alzheimer's disease drugs and regimens.

In these embodiments, these Alzheimer's disease drugs and regimens/treatments include, but are not limited to, treatment with APP synthesis Inhibitors, beta-secretase inhibitors, gamma-secretase inhibitors and modulators, AB aggregation inhibitors, AB immunotherapy, Cholesterol-lowering drugs, Anti-tau drugs, cholinesterase inhibitors, N-methyl D-aspartate (NMDA) antagonists, atypical antipsychotics, blockers of protein S-nitrosylation, glucagon-like peptide-1 receptor agonists, rapamycin, rapalogues, endocannabinoids, cannabionoids, neuroprotectors, molecules controlling calcium influx, antioxidants, anti-inflammatory drugs, drugs controlling control of glutamate homeostasis, autophagy inducers, hormones, hormonal regulators, statins, insulin, insulin carriers, multifunctional nanocarriers, vitamins, nutritional supplements, small RNA molecules, peptides, or ultrasound therapy. More specifically, APP synthesis inhibitors (+phenserine), beta-secretase inhibitors (MK-8931, E2609, LY2811376, LY2886721, PF-05297909, gamma-secretase inhibitors and modulators (semegacestat LY450139, avagacestat BMS-708163, PF-3084014, ELND006, tarenflurbil, CHF5074), AB aggregation inhibitors (tramiprosate (3APS), clioquinol (PBT1), PBT2, ELND005 (scyllo-inositol), PQ912), AB immunotherapy (GSK933776, AN1802+QS21, ACC-001, Alzheimer's disease-106, Bapineuzumab, Solanezumab, Gantenerumab (RO4909832), Ponezumab (PF-04360365), MABT5102A (crenezumab), BAN2401, Intravenous immunoglobulin, gantenerumab (R1450 or RO4909832)), anti-tau drugs (lithium, Tideglusib (NP031112), LMTX (methylene blue)), cholinesterase inhibitors (Razadyne® (galantamine), Exelon® (rivastigmine), and Aricept® (donepezil)), an N-methyl D-aspartate (NMDA) antagonists (Aricept® and Namzaric®, a combination of Namenda® and donepezil), atypical antipsychotics (olanzapine, quetiapine, risperidone), blockers of protein S-nitrosylation, agonist at the glucagon-like peptide-1 receptor, rapamycin and rapalogues, endocannabinoid and cannabionoids, neuroprotectors, molecules controlling calcium influx, antioxidants (Vitamin E, vitamin C, α-lipoic acid, coenzyme Q), anti-inflammatory molecules and drugs, drugs controlling control of glutamate homeostasis, autophagic inducers, hormones and hormonal regulators, statins, insulin and insulin carriers including intranasal insulin, long acting insulin and thalidomide), Ramipril, resveratrol, multifunctional nanocarriers, vitamins and nutritional supplements, small RNA molecules, peptides, and ultrasound therapy. In some embodiments, the Alzheimer's disease drugs and regimens are pending FDA-approval, selected from a list of FDA-registered clinical trials for drug approval, which may be obtained on the world wide web address of the U.S. Food and Drug Administration.

Exemplary Methods, H1.0K180me2 Levels:

In some embodiments, provided herein is a method using an H1.0K180me2 antibody for determining whether an individual diagnosed with Alzheimer's disease receiving ongoing treatment, will benefit or continue to benefit from the ongoing treatment, comprising: (a) providing a biological sample from the individual who is receiving ongoing treatment; (b) contacting the biological sample with an H1.0K180me2 antibody; (c) determining the concentration of H1.0K180me2 in the sample that binds the antibody; and (d) selecting an individual who will benefit or continue benefit from treatment, wherein an increase in the concentration relative to a control indicates that the individual will benefit or continue to benefit from treatment, and wherein a decrease or no change in the concentration relative to a control may indicate that the individual will not likely benefit or not continue to benefit from or be responsive to the treatment. A control includes, but is not limited to, samples from individuals with Alzheimer's disease not receiving a treatment, or a control sample from the same individual isolated earlier in time prior to the start of treatment. In some embodiments, the concentration of circulating H1.0K180me2 is determined. In some embodiments, the change in the concentration is relative to a threshold established by a Receiver Operating Characteristic curve analysis for optimal specificity and sensitivity.

Also provided herein is a method using an H1.0K180me2 antibody for use in treatment selection for an individual diagnosed with Alzheimer's disease, for determining treatment options for an individual diagnosed with Alzheimer's disease, and for determining whether who may benefit from a particular treatment. In some embodiments, the method comprises: (a) providing a biological sample from the individual, before the individual is treated for Alzheimer's disease; (b) contacting the biological sample with a candidate treatment; (c) contacting the biological sample with an H1.0K180me2 antibody; (d) determining the concentration and/or subcellular localization of H1.0K180me2 in the sample that binds the antibody; and (e) selecting an individual who may benefit from the treatment, wherein an increase in the concentration relative to a control or a decrease in cytoplasmic subcellular localization indicates that the individual may benefit from a treatment and wherein an decrease or no change in the concentration relative to a control or an increase or no change in cytoplasmic subcellular localization may indicate that the individual will not benefit from a treatment. In another embodiment, the method comprises: (a) administering to the individual the candidate treatment; (b) providing a biological sample from the individual, after administration of the treatment; (c) contacting the biological sample with an H1.0K180me2 antibody; (d) determining the concentration and/or subcellular localization of H1.0K180me2 in the sample that binds the antibody; and (e) selecting an individual who may benefit from the treatment, wherein an increase in the concentration relative to a control or a decrease in cytoplasmic subcellular localization indicates that the individual may benefit from a treatment and wherein an decrease or no change in the concentration relative to a control or an increase or no change in cytoplasmic subcellular localization may indicate that the individual will not benefit from a treatment. A control can include, but is not limited to, samples from healthy individuals, or contacting the biological sample with a placebo treatment. In some embodiments, the concentration of circulating H1.0K180me2 is determined. In some embodiments, the change in the concentration is relative to a threshold established by a Receiver Operating Characteristic curve analysis for optimal specificity and sensitivity.

In related embodiments, the methods provided herein are useful for ensuring that the H1.0K180me2 levels remain within physiological levels or within an established therapeutic drug range.

In related embodiments, the methods provided herein are useful for the monitoring of Alzheimer's disease, wherein the methods described may be used to measure the H1.0K180me2 levels for the purpose of adjusting treatments/interventions as required. In related embodiments, the methods provided herein are useful for monitoring the effects of an Alzheimer's disease drug or nutritional regiment or life style adjustment in an individual receiving such treatment.

In related embodiments, the methods provided herein are useful for monitoring the clinical performance in any observational or interventional clinical study for Alzheimer's disease, wherein (a) an observational study refers is a study in which test results obtained during the study are not used for patient management and do not impact treatment decisions; and (b) an interventional study is a study in which test results obtained during the study may influence patient management decisions and may be used to guide treatments.

In related embodiments, the methods provided herein are useful for serial measurement, whereby multiple determinations are taken over time. These types of monitoring methods may be used for the detection/assessment of disease progression/regression, disease recurrence, minimum residual disease, response/resistance to treatment, and/or adverse effects due to treatment. These types of monitoring methods may be designed to evaluate changes in an individual's state.

In related embodiments, the methods provided herein are useful for prediction of Alzheimer's disease treatment response or reaction, wherein the methods described herein may be used to measure factors that determine the likelihood of patient responses or adverse reactions to a specific therapy. Described herein are predictive methods designed specifically for use as companion diagnostics.

In some embodiments of the methods described herein, the levels of H1.0K180me2 may be normalized against total IgG in the biological sample or normalized against total protein in the biological sample. In some embodiments of the methods described herein, the concentration of H1.0K180me2 may be determined as a relative ratio to non-methylated, labeled, synthetic H1.0 peptide.

In embodiments of the methods described herein, the individual is greater than 50 years old. In some embodiments of the method described herein, the individual is less than 50 years old. In some embodiments, of the methods described herein, the individual is at least 50 years old, is at least 55 years old, is at least 60 years old, is at least 65 years old, is at least 70 years old, is at least 75 years old, or is at least 80 years old. In an exemplary embodiment, the individual is at least 60 years old.

In related embodiments, the methods may be used for screening for new Alzheimer's disease drugs and regimens.

D. Detection of Senescence

Provided herein are H1.0K180me2 antibodies, for use in detecting senescence. As provided herein, senescence is associated with replicative senescence (REP-SEN), genotoxic stress-induced senescence and radiation-induced senescence.

Generally the method for the detection of senescence involves the direct detection of H1.0K180me2. For direct detection of H1.0K180me2, the method generally comprises (a) contacting a biological sample from the individual with an H1.0K180me2 antibody; and (b) determining the concentration of the H1.0K180me2 antigen in the sample that binds the antibody, wherein an increase in the concentration relative to a control indicates that the biological sample comprises senescent cells. In some embodiments, the change in the concentration is relative to a threshold established by a Receiver Operating Characteristic curve analysis for optimal specificity and sensitivity.

In some embodiments, the methods may be used for identifying individuals that have undergone senescence induced by a genotoxin. In some embodiments the genotoxic stress-induced senescence is a result of exposure of the individual to a DNA damaging agent, drug or toxin, for example radiation, UV-light, bleomycin and any other genotoxic drugs including but not limited to Trazodone, Etotifen, Cephalexin, Nisoldipme, CGS 15943, Clotrimazole, 5-Nonyltryptamine, Doxepin, Pergolide, Paroxetine, Resveratrol, Quercetin, Honokiol, 7-nitroindazole, Megestrol, Fluvoxamine, Etoposide, Veliparib, Rucaparib, Olaparib, Camptothecin, or Terbinafine and chemotherapeutic drugs in general.

In some embodiments, the methods are useful for identifying senescence in individuals undergoing chemotherapy treatments to ensure that the chemotherapy is effective. The chemotherapeutic agent in these embodiments may be selected from the group consisting of Alemtuzumab (Campath), Alitretinoin (Panretin), Allopurinol (Zyloprim), Altretamine, (Hexalen), Amifostine (Ethyol), Anastrozole (Arimidex), Arsenic Trioxide (Trisenox), Asparaginase (Elspar), BCG Live (TICE BCG), Bexarotene (Targretin), Bleomycin (Blenoxane), Busulfan Intravenous (Busulfex), Busulfan Oral (Myleran), Calusterone (Methosarb), Capecitabine (Xeloda), Streptozocin (Zanosar), Talc (Sclerosol), Tamoxifen (Nolvadex), Temozolomide (Temodar), Teniposide, VM-26 (Vumon), Testolactone (Teslac), Thioguanine, 6-TG (Thioguanine), Thiotepa (Thioplex), and Topotecan (Hycamtin).

E. Detection of DNA Damage

Provided herein are H1.0K180me2 antibodies, for use in detecting DNA damage, for example acute DNA damage.

As described above, in the context of DNA damaging agents, dimethylation of H1.0K180 (H1.0K180me2) is observed on chromatin following acute DNA damage with bleomycin, a chemotherapeutic agent (FIG. 11A). Also as described above, in the context of genotoxic stress, H1.0K180me2 is released from the chromatin upon genotoxic stress induced senescence (days after treatment with a DNA damaging agent) (FIG. 12A) and is secreted out of the cells into the extracellular space (FIG. 12B).

Generally the method for the detection DNA damage involves the direct detection of H1.0K180me2. For direct detection of H1.0K180me2, the method generally comprises (a) contacting a biological sample from the individual with an H1.0K180me2 antibody; and (b) determining the concentration of the H1.0K180me2 antigen in the sample that binds the antibody, wherein an increase in the concentration relative to a control indicates that the biological sample has undergone DNA damage. In some embodiments, the change in the concentration is relative to a threshold established by a Receiver Operating Characteristic curve analysis for optimal specificity and sensitivity.

In some embodiments the DNA damage is a result of exposure of the cells or an individual to a DNA damaging agent, drug or toxin, for example radiation, bleomycin or other DNA-damaging agents (e.g. chemotherapeutic drugs discussed above).

In some embodiments, the method is useful for determining DNA damage within 5 minutes, 10 minutes, 15 minutes, 20 minutes, 25 minutes, 30 minutes, 45 minutes, 60 minutes, 75 minutes, 90 minutes, 2 hours, 3 hours, 4 hours, 5 hours, 24 hours, 48 hours, 3 days, 4 days, or up to 5 days of such exposure to a genotoxin or DNA damaging agent.

In some embodiments, provided herein is a portable unit for the detection of DNA damage. The unit can comprise a sample collection unit, a reader, and an assay module comprising an H1.0K180me2 antibody.

F. Detection of Radiation Exposure

Provided herein are H1.0K180me2 antibodies, for use in detecting radiation exposure.

In the context of radiation exposure, exposure to ionizing radiation induces increased levels of circulating H1.0 K180me2 in serum (FIG. 13A and FIG. 13B. The effect of ionizing radiation on H1.0K180me2 levels in serum was examined. Serum was collected from wild-type mice before and either 2 hours or 48 hours after exposure to 7 Gy of ionizing radiation. H1.0K180me2 serum levels 2 hours (mouse 1) or 48 hours (mouse 2) after irradiation were compared to initial levels before treatment using slot blot and immunoblotting with α-H1.0K180me2 antibody (FIG. 13A). The concentration of H1.0K180me2 in each serum sample was calculated using a standard curve of H1.0K180me2 peptide included in each analysis. Mouse serum albumin was used as a loading control. H1.0K180me2 dot blot bands were quantified and normalized by serum albumin. Relative increases in H1.0K180me2 after irradiation are shown (FIG. 13B). Western blot analysis of equal volumes of mouse serum with α-H1.0K180me2 antibody also showed increased H1.0K180me2 after irradiation (FIG. 13C).

Generally the method for the detection of radiation exposure involves the direct detection of H1.0K180me2. For direct detection of H1.0K180me2, the method generally comprises (a) contacting a biological sample from the individual with an H1.0K180me2 antibody; and (b) determining the concentration of the H1.0K180me2 antigen in the sample that binds the antibody, wherein an increase in the concentration relative to a control indicates that radiation exposure has occurred. In some embodiments, the change in the concentration is relative to a threshold established by a Receiver Operating Characteristic curve analysis for optimal specificity and sensitivity. In one exemplary embodiment, the change in the concentration of the H1.0 K170me2 antigen after 2 hrs after 7Gy X-ray exposure is from 12 umol/L to 21 umol/L, and from 26 umol/L to 35 umol/L after 48 hrs.

In some embodiments, the method is useful for determining radiation exposure within 5 minutes, 10 minutes, 15 minutes, 20 minutes, 25 minutes, 30 minutes, 45 minutes, 60 minutes, 75 minutes, 90 minutes, 2 hours, 3 hours, 4 hours, 5 hours, 24 hrs, 48 hrs, 3 days, 4 days, or up to 5 days of such exposure.

In some embodiments, the method is useful determining such exposure in a field situation, for example in a combat zone, with military personnel.

In some embodiments, provided herein is a portable unit for the detection of radiation damage. The unit can comprise a sample collection unit, a reader, and an assay module comprising an H1.0K180me2 antibody.

G. H1.0K180me2 and Rapalogues

The mammalian target of rapamycin (mTOR) has emerged as a promising therapeutic target. Rapamycin and some rapamycin derivatives, rapamycin analogs, and other mTOR inhibitors are FDA-approved drugs for treatment of certain disease states.

Figure 14:
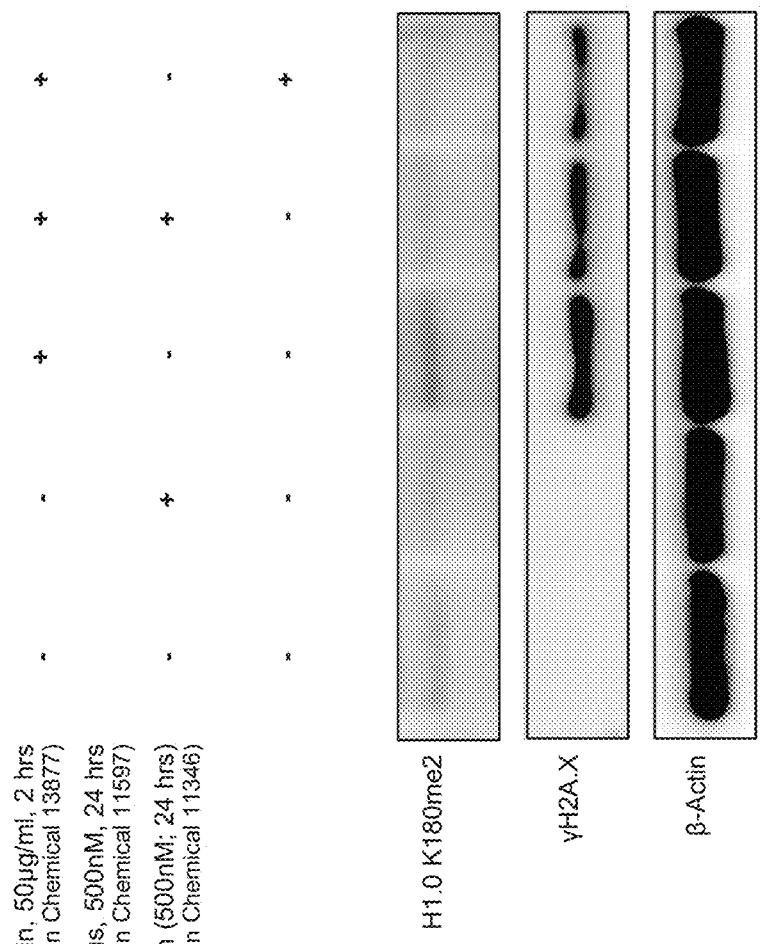
FIG. 14 shows a western blot analysis of H1.0K180me2 in SR hADSCs (self renewing human adipose derived stem cells) after bleomycin treatment, revealing that everolimus, a derivative of rapamycin, can act to block H1.0K180me2 appearance upon DNA damage.

The inventors have found that the detection of H1.0K180me2 may be useful for the screening of an individual's responsiveness to rapamycin, rapamycin derivatives, rapamycin analogs, and other mTOR inhibitors, referred to collectively as "rapalogues," and may be useful for monitoring rapalogue-based therapeutic regimens. The inventors have also found that the detection of H1.0K180me2 may be useful for drug screening purposes, for the screening of additional rapalogues. Specifically, it is shown here that a rapamycin derivative and immunosuppressant, everolimus, blocks the appearance of H1.0K180me2 upon DNA damage (FIG. 14). It has also been observed that treatment with a rapalogue, prior to, or in parallel with a genotoxic stress exposure, may reduce the effect of the genotoxic stressor, as evidenced by a change in the concentration and/or subcellular localization of H1.0K180me2.

As used herein, rapalogues include FDA-approved rapalogues, and those rapalogues presently undergoing clinical trials. FDA-approved rapalogues include Rapamycin, Sirolimus, Rapamune, Everolimus, RAD001, Afinitor, Zortress, Temsirolimus, CCI-779, Torisel, Ridaforolimus, AP23573, MK-8669, Deforolimus, Zotarolimus, and ABT-578. Other Rapalogues AZD8055, AZD2014, OSI-027, MLN0128, WYE-132, Torin1, PI-103, P7170, PF-04691502, PF-05212384, PKI-587, GNE477, PKI-180, WJD008, XL765, SAR245409, NVP-BEZ235, BGT226, SF1126, GSK2126458, Ku-0063794, WYE-354, NVP-BEZ235, PF-05212384, XL765, Torin 2, WYE-125132, and OSI-027.

Generally provided herein is a method for monitoring the effects of a rapalogue-based treatment ongoing in an individual diagnosed with cancer, an immunodeficiency, diabetes, arthritis, Alzheimer's disease and other neurodegenerative diseases, cardiovascular disease, an autoimmune disease, and other age related pathologies.

Thus, in some embodiments, provided herein is a method of determining whether an individual receiving treatment with a rapalogue is responsive to such treatment, comprising: (a) contacting a biological sample from the individual with an H1.0K180me2 antibody; (b) determining the concentration and/or localization of H1.0K180me2 in the sample that binds the antibody; and (c) determining whether the individual is responsive to treatment, wherein a decrease in the concentration established or a change in the localization relative to a control indicates that the individual is responsive to the rapalogue. In some embodiments, it is determined that the rapalogue treatment is not effective, or needs to be modified if there is an increase in the extracellular concentration of the H1.0K180me2 relative to a control. In some embodiments it is determined that the rapalogue treatment is not effective, or needs to be modified if there is an increase in the cytoplasmic localization of the H1.0K180me2 relative to a control. In some embodiments, the decrease is relative to an age-matched control that is not diagnosed with the relevant disease for which the rapalogue is being administered. In some embodiments it is determined that the treatment is effective, and should be continued if there is a decrease in the extracellular or cytoplasmic concentration of the H1.0K180me2 protein relative to a control. In some embodiments, the method further comprises using the information to modify the treatment type, course, duration, and/or dosage. In some embodiments, the concentration of circulating H1.0K180me2 is determined. In some embodiments, the change in the concentration is relative to a threshold established by a Receiver Operating Characteristic curve analysis for optimal specificity and sensitivity.

In some embodiments, provided herein is a method for selecting an individual, diagnosed with or suspected of having cancer, an immunodeficiency, diabetes, Alzheimer's disease or other neurodegenerative diseases, cardiovascular disease, an autoimmune disease, arthritis, and other age related pathologies, who may benefit from rapalogue treatment, or to determine whether an individual may respond to treatment with a rapalogue. In some embodiments, this method comprises providing a biological sample from the individual; treating the sample with a rapalogue in vitro, ex vivo, in slice culture, or in tissue culture; and determining the concentration and/or subcellular localization of H1.0K180me2 in the sample. In some embodiments, the concentration of the H1.0K180me2 is determined, by measuring the concentration of H1.0K180me2 in the sample using an H1.0K180me2 antibody. In some embodiments it is determined that the rapalogue treatment may not be effective, if there is an increase in the cytoplasmic or extracellular concentration of the H1.0K180me2 relative to a control. In some embodiments it is determined that the rapalogue treatment may not be effective, if there is an increase in the cytoplasmic localization of the H1.0K180me2 relative to a control. In some embodiments, the decrease is relative to an age-matched control that is not diagnosed disease for which the individual may receive a rapalogue treatment. In some embodiments it is determined that the treatment may be effective, if there is a decrease in the cytoplasmic or extracellular concentration of the H1.0K180me2 protein relative to a control. In some embodiments, the change in the concentration is relative to a threshold established by a Receiver Operating Characteristic curve analysis for optimal specificity and sensitivity.

In some embodiments, the methods provided herein further comprises using the information to modify the treatment type, course, duration, and/or dosage.

In other embodiments, provided herein is the use of the detection of H1.0K180me2 to monitor for the ability for new rapalogues to be identified (drug screening applications).

H. Detection of Biological Aging

Provided herein are H1.0K180me2 antibodies, for use in detecting biological aging. As provided herein, biological aging markers or biomarkers of aging are expected to find many uses in biological research since age is a fundamental characteristic of most organisms.

There can be differences between chronological and biological age. Some individuals age more rapidly, while others, due to good habits, genes and/or lack of environmental stressors, age more slowly making them healthier and "younger looking" longer. Being able to track one's biological age may help to modify life style (similar to tracking body mass index) or help to deploy antiaging procedures.

Accurate measures of biological age by aging markers are useful for testing the age-related diseases theories of biological aging, such as (i) diagnosing various age related diseases and for defining cancer subtypes, (ii) predicting/prognosticating the onset of various diseases, and serving as (iii) surrogate markers for evaluating therapeutic interventions including rejuvenation approaches.

Generally the method for the detection of biological aging involves the direct detection of H1.0K180me2. For direct detection of H1.0K180me2, the method generally comprises (a) contacting a biological sample from the individual with an H1.0K180me2 antibody; and (b) determining the concentration of the H1.0K180me2 antigen in the sample that binds the antibody, wherein an increase in the concentration relative to a control indicates that the biological sample is from an individual that has experienced biological aging. In some embodiments, the change in the concentration is relative to a threshold established by a Receiver Operating Characteristic curve analysis for optimal specificity and sensitivity.

I. Diagnostic Kits and Articles of Manufacture

Provided herein are kits useful for the detection of H1.0K180me2. In some embodiments, the kit comprises one or more H1.0K180me2 antibodies as described herein. In certain embodiments, the antibodies. In addition, the kits can optionally include instructional materials for carrying out any of the methods described herein. While the instructional materials typically comprise written or printed materials, they are not limited to such. Any medium capable of storing such instructions and communicating them to an end user is contemplated herein. Such media include, but are not limited to, electronic storage media (e.g., magnetic discs, tapes, cartridges, chips), optical media (e.g., CD ROM), and the like. Such media can include addresses to internet sites that provide such instructional materials.

The kits may also include additional components to facilitate the particular application for which the kit is designed. Thus, for example, where a kit contains an anti-H1.0K180me2 that is labeled, the kit may additionally contain reagents for detecting the label (e.g., enzyme substrates for enzymatic labels, filter sets to detect fluorescent labels, appropriate secondary labels, and the like). The kits may additionally include buffers and other reagents routinely used for the practice of a particular method.

An exemplary kit useful in an immunoassay to detect H1.0K180me2 may include an H1.0K180me2 protein or peptide. This peptide may be employed, for example, as a positive control or as competitor in a competitive immunoassay, and may be labeled or not, depending on the format of the assay to be carried out.

Another exemplary kit useful in an immunoassay to detect H1.0K180me2, in addition to an anti-H1.0K180me2 peptide, may include an H1.0K180me2 antibody. This antibody may be employed, for example, as a positive control or as competitor in a competitive immunoassay, and may be labeled or not, depending on the format of the assay to be carried out.

Also provided herein are transdermal patches for measuring a concentration of a hypodermal target H1.0K180me2 proteins and peptides, comprising: a substrate comprising an H1.0K180me2 antibody; and a plurality of microneedles. In some embodiments, the patches are transdermal microneedle array patches. In some embodiments, the substrate of the patches is elastically stretchable. In some embodiments, provided herein are kits comprising patches which comprise the antibodies or peptides provided herein, and optionally, instructions for use. In some embodiments, the patch is useful for detecting and measuring the concentration of H1.0K180me2 in a biological sample, for the purpose of detecting replicative senescence, DNA damage, genotoxic stress, radiation exposure, and Alzheimer's disease, useful for monitoring therapeutic regimens, and useful for drug screening.

Also provided herein is a portable unit, for detection, for example for the detection of DNA damage or radiation exposure. The unit may comprise a sample collection unit, a reader, and an assay module comprising an H1.0K180me2 antibody.

Also provided herein are lateral flow strips or test strips suitable for a lateral flow assay of an analyte, comprising a sample receiving zone, wherein the sample receiving zone comprises either an H1.0K180me2 antibody. In some embodiments, antibody is conjugated to a label.

ENUMERATED EMBODIMENTS

The invention may be defined by reference to the following enumerated, illustrative embodiments.

Embodiment 1

An antibody that specifically binds a protein comprising an H1.0K180me2 antigen or a peptide thereof, wherein the antigen-binding domain of the antibody comprises:
  any one of the CDR-L1 amino acid sequences of Table 4;
  any one of the CDR-L2 amino acid sequences of Table 5; and
  any one of the CDR-L3 amino acid sequences of Table 6.

Embodiment 2

An antibody that specifically binds a protein comprising an H1.0K180me2 antigen or a peptide thereof, wherein the antigen-binding domain of the antibody comprises:
  any one of the CDR-H1 amino acid sequences of Table 7;
  any one of the CDR-H2 amino acid sequences of Table 8; and
  any one of the CDR-H3 amino acid sequences of Table 9.

Embodiment 3

An antibody that specifically binds a protein comprising an H1.0K180me2 antigen or a peptide thereof, wherein the antigen-binding domain of the antibody comprises any one of the CDR-L amino acid sequences of Tables 4, 5, and 6, and comprises any one of the CDR-H amino acid sequences of Tables 7, 8, and 9.

Embodiment 4

The antibody of embodiment 1, wherein the antigen-binding domain of the antibody comprises
a CDR-L1 comprising the amino acid sequence of SEQ ID NO: 10 or SEQ ID NO: 11;
a CDR-L2 comprising the amino acid sequence of SEQ ID NO: 14 or SEQ ID NO: 15; and
a CDR-L3 comprising the amino acid sequence of SEQ ID NO: 18.

Embodiment 5

The antibody of embodiment 1, wherein the antigen-binding domain of the antibody comprises
a CDR-H1 comprising the amino acid sequence of SEQ ID NO: 20, SEQ ID NO: 21, SEQ ID NO: 22 or SEQ ID NO: 23;
a CDR-H2 comprising the amino acid sequence of SEQ ID NO: 28, SEQ ID NO: 29, SEQ ID NO: 30 or SEQ ID NO: 31; and
a CDR-H3 comprising the amino acid sequence of SEQ ID NO: 36 or SEQ ID NO: 37.

Embodiment 6

An antibody that specifically binds a protein comprising an H1.0K180me2 antigen or a peptide thereof, wherein the light chain variable domain of the antibody comprises the amino acid sequence of SEQ ID NO: 8 or SEQ ID NO: 9.

Embodiment 7

An antibody that specifically binds a protein comprising an H1.0K180me2 antigen or a peptide thereof, wherein the heavy chain variable domain of the antibody comprises the amino acid sequence of SEQ ID NO: 6 or SEQ ID NO: 7.

Embodiment 8

An antibody that specifically binds a protein comprising an H1.0K180me2 antigen or a peptide thereof, wherein the heavy chain variable domain of the antibody comprises the amino acid sequence of SEQ ID NO: 6 or SEQ ID NO: 7 and the light chain variable domain of the antibody comprises the amino acid sequence of SEQ ID NO: 8 or SEQ ID NO: 9.

Embodiment 9

The antibody of embodiment 8, wherein the heavy chain variable domain of the antibody comprises the amino acid sequence of SEQ ID NO: 6 and the light chain variable domain of the antibody comprises the amino acid sequence of SEQ ID NO: 8.

Embodiment 10

The antibody of embodiment 8, wherein the heavy chain variable domain of the antibody comprises the amino acid sequence of SEQ ID NO: 7 and the light chain variable domain of the antibody comprises the amino acid sequence of SEQ ID NO: 9.

Embodiment 11

The antibody of any one of embodiments 1 to 10, wherein the antibody is chimeric or humanized.

Embodiment 12

The antibody of any one of embodiments 1 to 10, wherein the antibody is a monoclonal antibody.

Embodiment 13

The antibody of any one of embodiments 1 to 10, wherein the antibody is an antigen-binding fragment.

Embodiment 14

The antibody of any one of embodiments 1 to 13, wherein the antibody exhibits reduced binding to the H1.0K180me2 protein or peptide, if the protein or peptide comprises residues other than K180 that are methylated.

Embodiment 15

The antibody of any one of embodiments 1 to 14, wherein the antibody does not bind, or only minimally binds, if the H1.0K180me2 protein or peptide comprises methylated lysine residues at lysine residues corresponding to K166, K172, K174, K175, and/or K177 of a human histone H1.0 protein.

Embodiment 16

The antibody of any one of any one of embodiments 1 to 15, wherein the antibody is conjugated to a label.

Embodiment 17

The antibody of any one of embodiment 16, wherein the antibody is attached to solid surface.

Embodiment 18

The antibody of embodiment 17, wherein the antibody attached a bead, column, resin, or a microplate.

Embodiment 19

The antibody of any one of any one of embodiments 1 to 15, wherein the antibody is conjugated to an agent.

Embodiment 20

The antibody of embodiment 19, wherein the agent is selected from the group consisting of a radionuclide, a cytotoxin, a chemotherapeutic agent, a drug, a pro-drug, a toxin, an enzyme, an immunomodulator, a pro-apoptotic agent, a cytokine, a hormone, an oligonucleotide, an antisense molecule, a siRNA, and a second antibody.

Embodiment 21

A method of determining whether an individual has, or is at risk of, developing, Alzheimer's disease, comprising:
contacting a biological sample from the individual with the antibody of any one of embodiments 1 to 18; and
determining the concentration of the protein comprising an H1.0K180me2 antigen or a peptide thereof in the sample that binds the antibody, wherein a decrease in the concentration relative to a control indicates that the individual has, or is at risk of developing, Alzheimer's disease.

Embodiment 22

The method of embodiment 21, further comprising treating the individual with an Alzheimer's disease drug or regimen if it is determined that the individual has, or is at risk of developing, Alzheimer's disease.

Embodiment 23

A method of determining whether an individual diagnosed with Alzheimer's disease and receiving treatment for the Alzheimer's disease, will benefit from the treatment or will continue to benefit from the treatment, the method comprising:
  contacting a biological sample from the individual with the antibody of any one of embodiments 1 to 18; and
  determining the concentration of the protein comprising an H1.0K180me2 antigen or a peptide thereof in the sample that binds the antibody; and
  determining that the individual will benefit from the treatment or will continue to benefit from the treatment if there is an increase in the concentration, relative to a control.

Embodiment 24

The method of embodiment 23, further comprising treating the individual with an Alzheimer's disease drug or regimen if it is determined that the individual will benefit or continue to benefit from the treatment.

Embodiment 25

A method of determining whether an individual diagnosed with Alzheimer's disease will benefit from a candidate treatment, wherein the individual has not yet started the treatment, the method comprising:
  administering to the individual a candidate treatment;
  contacting a biological sample from the individual after administration of the candidate treatment with the antibody of any one of embodiments 1 to 18; and
  determining the concentration and/or subcellular localization of the protein comprising an H1.0K180me2 antigen or a peptide thereof in the sample that binds the antibody; and
  determining that the individual will benefit from the candidate treatment if there is an increase in the concentration or an decrease in cytoplasmic subcellular localization, relative to a control.

Embodiment 26

A method of determining whether an individual diagnosed with Alzheimer's disease will benefit from a candidate treatment, wherein the individual has not yet started the treatment, the method comprising:
  contacting a biological sample from the individual with a candidate treatment;
  contacting a biological sample from the individual with the antibody of any one of embodiments 1 to 18;
  determining the concentration and/or subcellular localization of the protein comprising an H1.0K180me2 antigen or a peptide thereof in the sample that binds the antibody; and
  determining that the individual will benefit from the candidate treatment if there is an increase in the concentration relative to a control or an decrease in cytoplasmic subcellular localization, relative to a control.

Embodiment 27

The method of any one of embodiments 25-26, wherein the treatment is selected from the group consisting of APP synthesis Inhibitors, beta-secretase inhibitors, gamma-secretase inhibitors and modulators, AB aggregation inhibitors, AB immunotherapy, Cholesterol-lowering drugs, Anti-tau drugs, cholinesterase inhibitors, N-methyl D-aspartate (NMDA) antagonists, atypical antipsychotics, blockers of protein S-nitrosylation, glucagon-like peptide-1 receptor agonists, rapamycin, rapalogues, endocannabinoids, cannabionoids, neuroprotectors, molecules controlling calcium influx, antioxidants, anti-inflammatory drugs, drugs controlling control of glutamate homeostasis, autophagy inducers, hormones, hormonal regulators, statins, insulin, insulin carriers, multifunctional nanocarriers, vitamins, nutritional supplements, small RNA molecules, peptides, and ultrasound therapy.

Embodiment 28

A method of determining whether an individual has been exposed to a DNA damaging agent, comprising:
  contacting a biological sample from the individual with the antibody of any one of embodiments 1 to 18; and
  determining the concentration of the protein comprising an H1.0K180me2 antigen or a peptide thereof in the sample that binds the antibody, wherein an increase in the concentration relative to a control indicates that the individual has been exposed to a DNA damaging agent.

Embodiment 29

The method of embodiment 28, wherein the DNA damaging agent is radiation.

Embodiment 30

A method of determining whether an individual receiving treatment with a rapalogue is responsive to such treatment, comprising:
  contacting a biological sample from the individual with the antibody of any one of embodiments 1 to 18;
  determining the concentration of the protein comprising an H1.0K180me2 antigen or a peptide thereof in the sample that binds the antibody; and
  determining whether the individual is responsive to treatment, wherein a decrease in the concentration relative to a control indicates that the individual is responsive.

Embodiment 31

The method of embodiment 30, wherein the decrease is below a threshold established by a Receiver Operating Characteristic curve analysis for optimal specificity and sensitivity.

Embodiment 32

The method of embodiment 30, wherein the rapalogue is selected from the group consisting of Rapamycin, Sirolimus, Rapamune, Everolimus, RA 001, Afinitor, Zortress, Temsirolimus, CCI-779, Torisel, Ridaforolimus, AP23573, MK-8669, Deforolimus, Zotarolimus, ABT-578, AZD8055, AZD2014, OSI-027, MLN0128, WYE-132, Torin1, PI-103, P7170, PF-04691502, PF-05212384, PKI-587, GNE477, PKI-180, WJD008, XL765, SAR245409, NVP-BEZ235, BGT226, SF1126, GSK2126458, Ku-0063794, WYE-354, NVP-BEZ235, PF-05212384, XL765, Torin 2, WYE-125132, and OSI-027.

Embodiment 33

The method of any one of embodiments 21 to 32, wherein the increase or decrease in the concentration is above or below a threshold established by a Receiver Operating Characteristic curve analysis for optimal specificity and sensitivity.

Embodiment 34

The method of any one of embodiments 21 to 33, wherein the biological sample is selected from the group consisting of whole blood, plasma, serum, saliva, urine, synovial fluid, cerebrospinal fluid, bronchial lavage, ascites fluid, bone marrow aspirate, pleural effusion, tissue, cells, a biopsy, interstitial fluid, and lymphatic fluid.

Embodiment 35

A transdermal patch for measuring a concentration of a hypodermal target molecule, comprising:
a substrate comprising the antibody of any one of embodiments 1 to 18; and
a plurality of microneedles.

Embodiment 36

The patch of embodiment 35, wherein the patch is a transdermal microneedle array patch.

Embodiment 37

The patch of embodiment 35, wherein the substrate is elastically stretchable.

Embodiment 38

A portable unit for determining whether an individual has been exposed to radiation or a DNA-damaging agent, comprising:
a sample collection unit;
a reader;
an assay module comprising the antibody of any one of embodiments 1 to 18; and
a plurality of microneedles.

Embodiment 39

A test strip suitable for a lateral flow assay of an analyte, comprising a sample receiving zone, wherein the sample receiving zone comprises the antibody of any one of embodiments 1 to 18.

Embodiment 40

A method of treating a methylated H1.0-related disease or condition in an individual comprising administering to the individual a therapeutically effective amount of the antibody of any one of embodiments 1 to 20.

Embodiment 41

The method of embodiment 40, wherein the disease or condition is selected from the group consisting of Alzheimer's disease, radiation exposure, exposure to a genotoxic stressor, a disease or condition comprising the accumulation of senescent cells, and a disease or condition accompanied by elevated levels of H1.0K180me2 proteins or peptides.

Embodiment 42

A method of clearing H1.0K180me2 in an individual comprising administering to the individual a therapeutically effective amount of the antibody of any one of embodiments 1 to 20.

Embodiment 43

The method of embodiment 42, wherein the individual suffers from a disease or condition selected from the group consisting of Alzheimer's disease, radiation exposure, exposure to a genotoxin, exposure to a DNA damaging agent, and a condition comprising the accumulation of senescent cells.

Embodiment 44

A pharmaceutical composition comprising the antibody of any one of embodiments 1 to 20, and a pharmaceutically acceptable excipient.

Embodiment 45

A kit comprising any one of therapeutically effective amount of the antibody of any one of embodiments 1 to 18.

Embodiment 46

An article of manufacture comprising any one of the compositions of embodiments of embodiments 1 to 20, and 35 to 45.

Embodiment 47

A vector encoding an antibody that specifically binds a protein comprising an H1.0K180me2 antigen or a peptide thereof, comprising the nucleic acid of SEQ ID NO: 4.

Embodiment 48

A vector encoding an antibody that specifically binds a protein comprising an H1.0K180me2 antigen or a peptide thereof, comprising the nucleic acid of SEQ ID NO: 5.

Embodiment 49

A cell comprising the vector of any one of embodiments 47 to 48.

The following examples are included for illustrative purposes and are not intend to limit the scope of the invention.

EXAMPLES

Example 1: Recombinant Antibody Development Pipeline

The antibody development pipeline shown in FIG. 1 was split into four phases (Phase I-IV). In phase I, two New Zealand rabbits were immunized for antibody production. Injections were administered subcutaneously (SQ) as emulsions of Keyhole Limpet Hemocyanin (KLH)-conjugated H1.0K180me2 peptide (KLH-CAKPVKASKPKKAKPVK(me2)PK (SEQ ID NO: 72)) in Complete Freund's Adjuvant (CFA) or Incomplete Freund's Adjuvant (IFA). Initial immunization was performed with 0.5 mg of antigen ((KLH)-conjugated H1.0K180me2 peptide) in CFA at 10 SQ sites. 6 subsequent booster immunizations were performed at routine intervals over a 10-11 week period. Boosters consisted of 0.25 mg antigen in IFA at 4 SQ sites. Rabbits were bled at week 6 and at week 8. The titer of the immunization was assessed using ELISA by comparing pre- and post-immunization bleeds. Once an appropriate ELISA positive titer was recorded toward the immunizing antigen, peripheral blood mononuclear cells (PBMCs) were collected from one or both rabbits. B-cells were subsequently isolated by flow cytometry sorting using a dual-screening protocol which ensured only rabbit IgG and antigen-specific B-cells were isolated.

During phase II, total RNA was isolated from the sorted, antigen-positive B-cells. This was followed by creation of a single-chain variable fragment (scFv) surface-display library by reverse transcription-polymerase chain reaction (RT-PCR). This scFv library represents all the variable domain regions of the rabbit IgG antibodies capable of binding the H1.0K180me2 antigen.

Phase III consisted of multiple rounds of library screening to increase the specificity of the library towards H1.0K180me2. This was done by panning and flow cytometry to isolate scFv domains exhibiting the highest specificity to biotin-conjugated H1.0K180me2 peptide (Biotin-CAKPVKASKPKKAKPVK(me2)PK (SEQ ID NO: 73)), whilst selecting against scFv domains exhibiting specificity towards unmethylated H1.0 peptide (Biotin-CAK-PVKASKPKKAKPVKPK (SEQ ID NO: 74)).

The scFv domains with the highest specificity for H1.0K180me2 were sequenced by Sanger sequencing, before being moved on to phase IV. During phase IV, full-length IgG heavy-chain and light-chain clones were generated incorporating the scFv domains, followed by expression of compete, full-length recombinant rabbit monoclonal IgG antibodies. These antibodies were then validated for specificity to H1.0K180me2 using ELISA, slot blot immunoassay, and western blot. In total, 5 distinct antibody clones were created, sorted below A through E in order of their specificity for H1.0K180me2:

(a) Clone A (RW24)
(b) Clone B (RW6)
(c) Clone C (RW37)
(d) Clone D (RW28)
(e) Clone E (RW36)

Phases I-IV are summarized in the Table 11 below.

TABLE 11

H1.0K180me2 Monoclonal Antibody - Exemplary Development Pipeline

| Development Stage | Description |
| --- | --- |
| Phase I | Immunization of rabbits with KLH conjugated peptide. Isolation of rabbit peripheral blood mononuclear cells (PBMCs) from the animal(s) with the highest ELISA-positive titer, with subsequent screening and sorting of antigen-positive, and IgG-positive B cells |
| Phase II | Total RNA isolation from sorted, antigen-positive B cells, and preparation of surface-display library. |
| Phase III | Multi-round screening of display-library by flow cytometry and panning. |
| Phase IV | Generation of candidate full-length Heavy-chain and Light-chain clones, expression of full-length and complete recombinant rabbit monoclonal antibodies, and validation. |

Example 2: Analysis of Antibody Titer for Rabbit Antibody Clones by ELISA

The specificity of the recombinant rabbit anti-H1.0K180me2 monoclonal IgG antibody clones for H1.0K180me2 peptide was determined using ELISA in FIG. 2A. Wells were coated with H1.0K180me2 peptide; 50 ul of peptide solution (5 ug/ml) was used to coat each well. 100 ul of each clone antibody was added to wells in a 2× dilution series. Curves for each peptide were generated by plotting antibody concentration against measured O.D at 450 nm. In order to directly compare the binding efficiencies of the different clones, a threshold cut-off was selected that intersected the linear range of each of the clone titration curves (horizontal dashed line at O.D. 1.5). The concentration of antibody required to meet the threshold O.D was compared for each clone, and given in the figure legend. Clone A (RW24) has the highest binding affinity for H1.0K180me2 peptide.

The non-specific binding of the antibody clones to unmodified H1.0 peptide was also determined by ELISA as above in FIG. 2B. Clones D (RW28) and E (RW36) both bound to unmodified H1.0 peptide with high affinity. At the threshold concentration calculated above, Clone A (RW24) was 20× more efficient at binding H1.0K180me2 peptide than unmodified H1.0 peptide, Clone B (RW6): 23×, Clone C (RW37): 22×, Clone D (RW28): 2×, Clone E (RW36): 5×.

FIG. 2C provides raw data for ELISA plot generation of FIGS. 2A and 2B.

Example 3: Analysis of Specificity of Rabbit Antibody Clones by Slot Blot

The specificity of the above generated recombinant rabbit anti-H1.0K180me2 monoclonal IgG antibody clones was determined using slot blot analysis as shown in FIG. 3. Histone H1.0 peptides (unmodified, K180me1, K180me2) were transferred to membranes using a vacuum-manifold slot blot in a dilution series (100 pmol, 50 pmol, 25 pmol). The membranes were then immunoblotted using the antibody clones to identify potential cross-reactivity with unmodified or mono-methylated H1.0 peptide. Clones A, B and C are highly specific for H1.0K180me2, even in low concentrations. No cross-reactivity with either unmodified or H1.0K180me1 peptides was observed for these clones. Clones D and E were both able to detect H1.0K180me1 peptide in addition to H1.0K180me2, suggesting a lack of antibody specificity for H1.0K180me2.

Example 4: Analysis of Specificity of Antibody Clones by In Vitro Methylated H1.0K180me2

FIG. 4A shows an overview of the in vitro methylation approach. The methylation reaction comprised recombinant G9A (methyltransferase), an unlabeled methyl donor (S-Adenosyl-L-Methionine), and recombinant human H1.0 protein, which were incubated at 37° C. for 1 hour. During this incubation, G9A is capable of methylating full-length H1.0 protein, including the addition of K180me2. H1.0K180me2 can subsequently be identified using an anti-H1.0K180me2 rabbit polyclonal antibody to confirm methylation.

In order to identify the precise locations of methylation by G9A on full-length H1.0 protein, the above reaction was subsequently analyzed by LC-MS, and sites of methylation were identified. FIG. 4B displays the sequence of full-length H1.0 protein, and the number of "me" circles represents the methylation state of the lysine residue (mono- or di-methylated). In the presence of recombinant, full-length H1.0, G9A specifically methylates several C-terminal lysine residues, including H1.0K180me2.

Figure 4C:
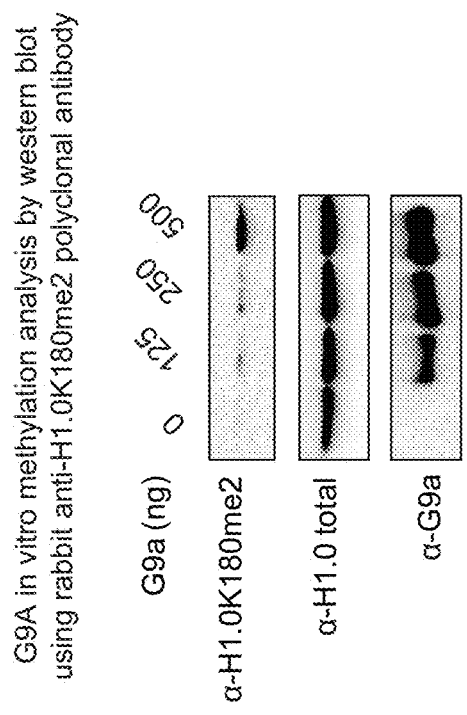
FIG. 4C shows detection of methylation of H1.0K180 by a H1.0K180me2 antibody.
Figure 4D:
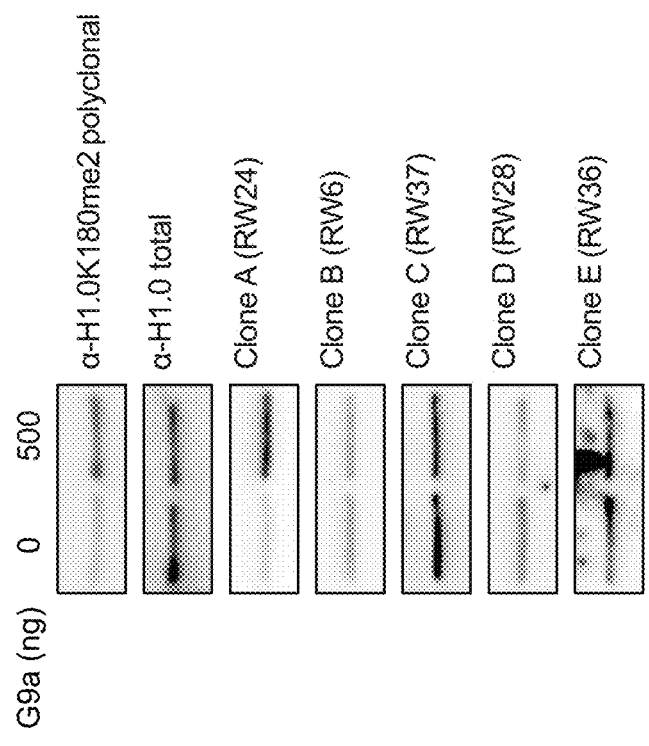
FIG. 4D is an analysis of antibody clone specificity for in vitro methylated H1.0.

FIG. 4C demonstrates an in-vitro methylation assay of recombinant full-length histone H1.0 with increasing amounts of G9A, and detection with rabbit anti-H1.0K180me2 polyclonal antibody. The top panel exhibits increased H1.0K180 methylation with increasing G9A concentration.

FIG. 4D shows an analysis of clone specificity for in vitro methylated H1.0. Clone A is capable of recognizing in vitro methylated H1.0, with minimal non-specific binding to unmethylated full length H1.0 in the absence of G9A protein. All other clones recognize unmethylated H1.0 and show no specificity for methylated full-length H1.0.

Example 5: Sequence Analysis of Clones a (RW24) and B (RW6)

Clones of interest were sequenced.

FIG. 5A is an EMBOSS NEEDLE (Li W. The EMBL-EBI bioinformatics web and programmatic tools framework. Nucleic Acids Research [6 Apr. 2015, 43(W1):W580-4)-pairwise sequence alignment of the heavy chain variable domain protein sequences of clones A and B. The heavy chain sequences share 61% identity and 70% similarity.

FIG. 5B is an EMBOSS NEEDLE pairwise sequence alignment of the light chain variable domain protein sequences of clones A and B. The light chain sequences share 83% identity and 88% similarity.

FIG. 5C provides DNA and protein sequences of the light and heavy chain variable domains for Clone A (RW24).

FIG. 5D is a schematic representation of one method of construction of full length light and heavy chain expression vectors incorporating the variable domain DNA sequences, in order to create full-length recombinant IgG antibodies.

Figure 7A:
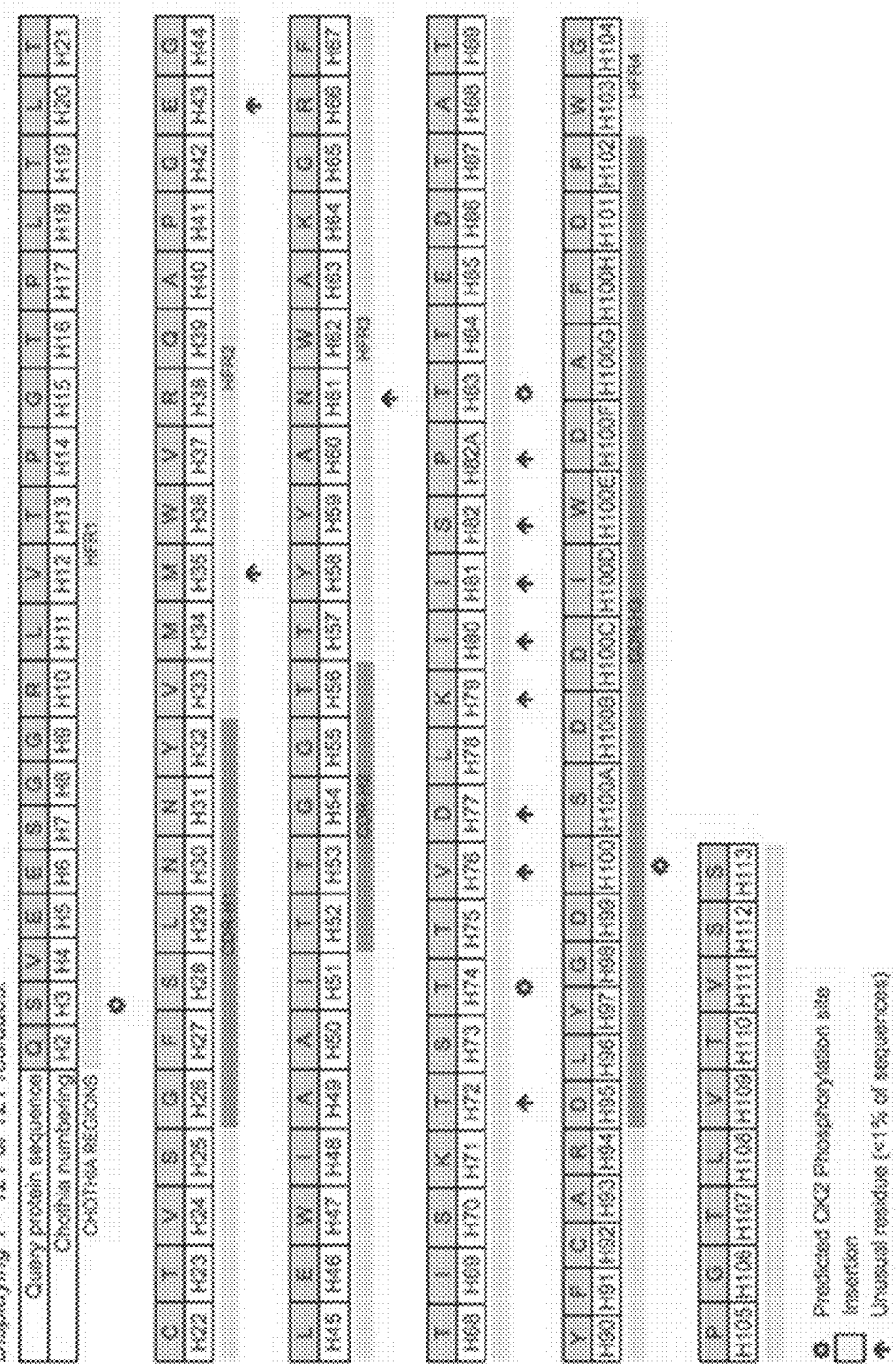
FIG. 7A depicts the sequence of antibody clone A heavy chain (SEQ ID NO: 6) and is annotated with structural information.

Example 6: Mapping Framework and CDR Regions of Clone a Heavy Chain with Chothia Predictive Software Shown in FIGS. 7A and 7B (left panel) are the analyses of clone A heavy chain and clone A light chain with Chothia, a program that predicts antibody architecture. Each residue of the heavy chain or light chain is displayed in the top box, and a residue number is assigned by Chothia in the box below each corresponding residue. Shown in light gray are predicted framework regions of the clone A heavy chain or light chain. Show in dark gray are the predicted CDRs. Stars indicated predicted CK2 phosporylation sites. Arrows indicate unusual residues for each location.

Figure 7B:
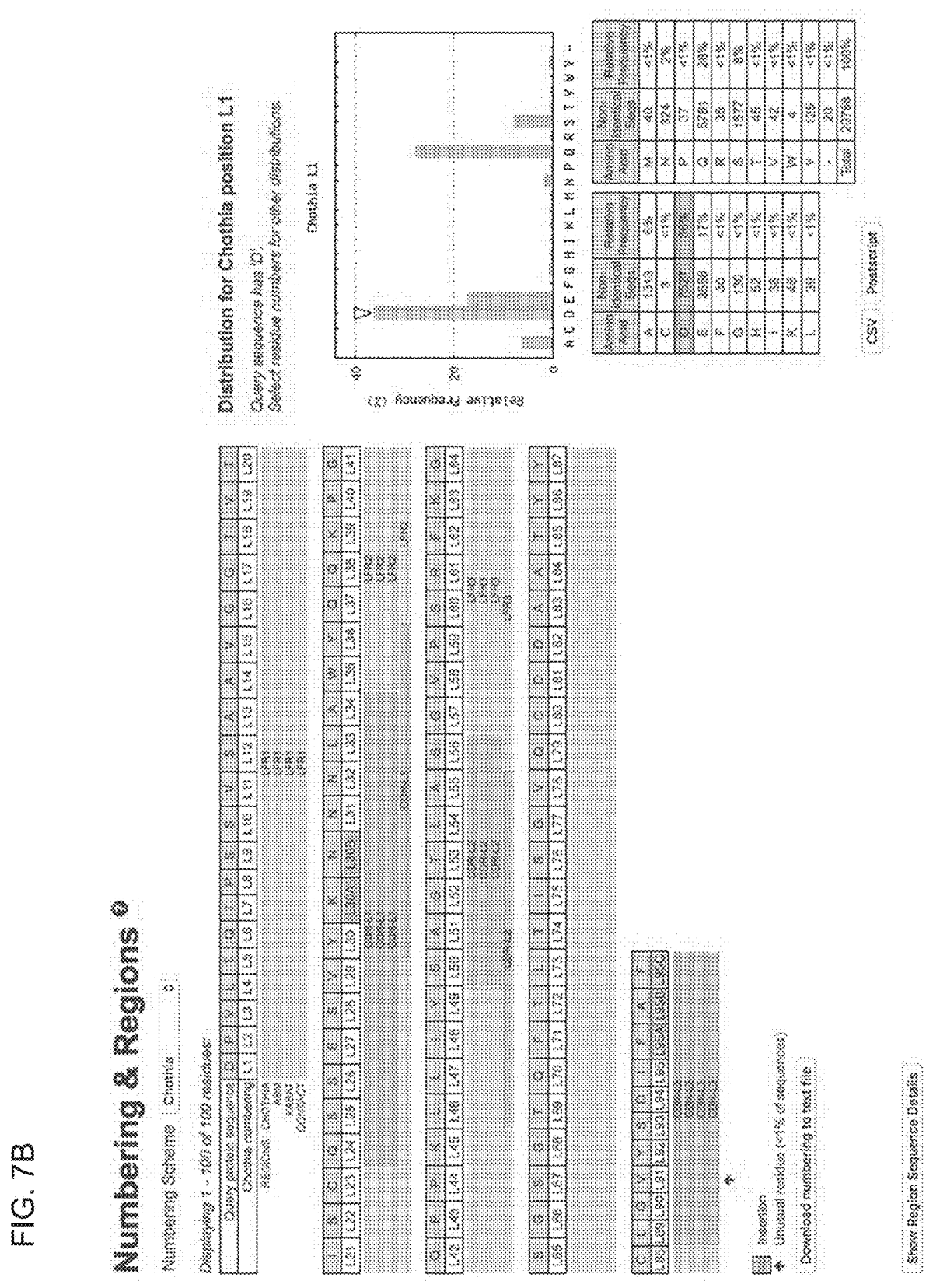

FIG. 7B (right panel) shows a distribution of residues that are predicted to be in position L1 for all Chothia predictions performed. In the example of clone A light chain, L1 position is aspartate, which has the greatest relative frequency for all amino acids predicted to be in position L1.

FIG. 7C depicts the predicted light chain complementary determining regions and framework regions for antibody Clone A, using the Chothia, AbM, Kabat, and Contact algorithms/numbering schemes.

FIG. 7D depicts the predicted heavy chain complementary determining regions and framework regions for antibody Clone A, using the Chothia, AbM, Kabat, and Contact algorithms/numbering schemes.

The invention claimed is:

1. An antibody that specifically binds a protein comprising an H1.0K180me2 antigen or a peptide thereof, wherein the antigen-binding domain of the antibody comprises:
   (a) a CDR-L1 comprising the amino acid sequence of SEQ ID NO: 10 or SEQ ID NO: 11;
   (b) a CDR-L2 comprising the amino acid sequence of SEQ ID NO: 14 or SEQ ID NO: 15;
   (c) a CDR-L3 comprising the amino acid sequence of SEQ ID NO: 18;
   (d) a CDR-H1 comprising the amino acid sequence of SEQ ID NO: 20, SEQ ID NO: 21, SEQ ID NO: 22 or SEQ ID NO: 23;
   (d) a CDR-H2 comprising the amino acid sequence of SEQ ID NO: 28, SEQ ID NO: 29, SEQ ID NO: 30 or SEQ ID NO: 31; and
   (e) a CDR-H3 comprising the amino acid sequence of SEQ ID NO: 36 or SEQ ID NO: 37.

2. The antibody of claim 1, wherein the antibody is chimeric or humanized.

3. The antibody of claim 1, wherein the antibody is a monoclonal antibody.

4. The antibody of claim 1, wherein the antibody is an antigen-binding fragment.

5. The antibody of claim 1, wherein the antibody exhibits reduced binding to the H1.0K180me2 protein or peptide, if the protein or peptide comprises residues other than K180 that are methylated.

6. The antibody of claim 1, wherein the antibody does not bind, or only minimally binds, if the H1.0K180me2 protein or peptide comprises methylated lysine residues at lysine residues corresponding to K166, K172, K174, K175, and/or K177 of a human histone H1.0 protein.

7. The antibody of claim 1, wherein the antibody is conjugated to a label.

8. The antibody of claim 1, wherein the antibody is attached to a solid surface.

9. The antibody of claim 8, wherein the antibody is attached to a bead, column, resin, or a microplate.

10. The antibody of claim 1, wherein the antibody is conjugated to an agent.

11. The antibody of claim 10, wherein the agent is selected from the group consisting of a radionuclide, a cytotoxin, a chemotherapeutic agent, a drug, a pro-drug, a toxin, an enzyme, an immunomodulator, a pro-apoptotic agent, a cytokine, a hormone, an oligonucleotide, an antisense molecule, a siRNA, and a second antibody.

12. A pharmaceutical composition comprising the antibody of claim 1, and a pharmaceutically acceptable excipient.

13. A kit comprising a therapeutically effective amount of the antibody of claim 1.

14. An article of manufacture comprising the composition of claim 1.

15. The article of manufacture of claim 14, wherein the article of manufacture is a transdermal patch or a transdermal microneedle array patch.

16. A method of determining whether an individual has been exposed to a DNA damaging agent, comprising:
    (a) contacting a biological sample from the individual with the antibody of claim 1; and
    (b) determining the concentration of the protein comprising an H1.0K180me2 antigen or a peptide thereof in the sample that binds the antibody, wherein an increase in the concentration relative to a control indicates that the individual has been exposed to a DNA damaging agent.

17. The method of claim 16, wherein the DNA damaging agent is radiation.

18. The method of claim 16, wherein the increase in the concentration is relative to a threshold established by a Receiver Operating Characteristic curve analysis for optimal specificity and sensitivity.

19. The method of claim 16, wherein the biological sample is selected from the group consisting of whole blood, plasma, serum, saliva, urine, synovial fluid, cerebrospinal fluid, bronchial lavage, ascites fluid, bone marrow aspirate, pleural effusion, tissue, cells, a biopsy, interstitial fluid, and lymphatic fluid.

20. An antibody that specifically binds a protein comprising an H1.0K180me2 antigen or a peptide thereof, wherein the heavy chain variable domain of the antibody comprises the amino acid sequence of SEQ ID NO: 6 and the light chain variable domain of the antibody comprises the amino acid sequence of SEQ ID NO: 8.

* * * * *